(12) United States Patent
Hinman et al.

(10) Patent No.: US 11,667,596 B2
(45) Date of Patent: *Jun. 6, 2023

(54) 2,3,5-TRIMETHYL-6-NONYLCYCLOHEXA-2,5-DIENE-1,4-DIONE FOR SUPPRESSING AND TREATING ALPHA-SYNUCLEINOPATHIES, TAUOPATHIES, AND OTHER DISORDERS

(71) Applicant: PTC THERAPEUTICS, INC., South Plainfield, NJ (US)

(72) Inventors: Andrew W. Hinman, San Francisco, CA (US); Charles R. Holst, Mountain View, CA (US); Angela Minnella, South Plainfield, NJ (US); Paul Mollard, Saratoga, CA (US); Sean Pintchovski, South Plainfield, NJ (US); Jeffrey K. Trimmer, San Carlos, CA (US); Eric Torrey, South Plainfield, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/523,880

(22) Filed: Nov. 10, 2021

(65) Prior Publication Data

US 2022/0106248 A1    Apr. 7, 2022

Related U.S. Application Data

(63) Continuation of application No. 17/218,042, filed on Mar. 30, 2021, now Pat. No. 11,174,212, which is a continuation of application No. PCT/US2019/056836, filed on Oct. 17, 2019.

(60) Provisional application No. 62/771,570, filed on Nov. 26, 2018, provisional application No. 62/747,080, filed on Oct. 17, 2018.

(51) Int. Cl.
    *C07C 50/04*    (2006.01)
    *A61P 25/16*    (2006.01)
    *C07C 46/10*    (2006.01)

(52) U.S. Cl.
    CPC .............. *C07C 50/04* (2013.01); *A61P 25/16* (2018.01); *C07C 46/10* (2013.01); *C07B 2200/13* (2013.01)

(58) Field of Classification Search
    None
    See application file for complete search history.

(56) References Cited

U.S. PATENT DOCUMENTS

| | | |
|---|---|---|
| 5,059,627 A | 10/1991 | Goto et al. |
| 5,801,159 A | 9/1998 | Miller et al. |
| 6,232,060 B1 | 5/2001 | Miller et al. |
| 6,271,266 B1 | 8/2001 | Miyamoto et al. |
| 6,608,196 B2 | 8/2003 | Wang et al. |
| 6,653,346 B1 | 11/2003 | Wang et al. |
| 7,432,305 B2 | 10/2008 | Miller et al. |
| 8,653,144 B2 | 2/2014 | Miller et al. |
| 9,399,612 B2 | 7/2016 | Miller |
| 11,174,212 B2 | 11/2021 | Hinman et al. |
| 2002/0143049 A1 | 10/2002 | Miller et al. |
| 2003/0176361 A1 | 9/2003 | Wand et al. |
| 2004/0105817 A1 | 6/2004 | Gilat et al. |
| 2005/0065099 A1 | 3/2005 | Walkinshaw et al. |
| 2006/0051844 A1 | 3/2006 | Heavner et al. |
| 2006/0281809 A1 | 12/2006 | Miller et al. |
| 2007/0072943 A1 | 3/2007 | Miller et al. |
| 2007/0225261 A1 | 9/2007 | Miller et al. |
| 2009/0291092 A1 | 11/2009 | Miller et al. |
| 2010/0010100 A1 | 1/2010 | Hinman et al. |
| 2010/0029706 A1 | 2/2010 | Miller et al. |
| 2010/0029784 A1 | 2/2010 | Hinman et al. |
| 2010/0056429 A1 | 3/2010 | Miller et al. |
| 2010/0063161 A1 | 3/2010 | Miller et al. |
| 2010/0105930 A1 | 4/2010 | Wesson et al. |
| 2010/0266591 A1 | 10/2010 | Bugelski et al. |
| 2010/0273892 A1 | 10/2010 | Miller et al. |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0101169 A1 | 4/2012 | Hawi |

(Continued)

FOREIGN PATENT DOCUMENTS

| WO | WO 99/61409 | 12/1999 |
|---|---|---|
| WO | WO 2007/095631 A2 | 8/2007 |

(Continued)

OTHER PUBLICATIONS

Muyderman et al., "Mitochondria dysfunction in amyotrophic lateral sclerosis a al id pharmacological target?", British Journal of Pharmacology (2014), vol. 171, pp. 2191-2205.

(Continued)

*Primary Examiner* — Joseph R Kosack

(74) *Attorney, Agent, or Firm* — Squire Patton Boggs (US)

(57) ABSTRACT

Disclosed herein are methods of treating or suppressing a disorder selected from the group consisting of α-synucleinopathies, tauopathies, ALS, traumatic brain injury, and ischemic-reperfusion related injuries.ury, comprising administering to a subject in need thereof a therapeutically effective amount of a compound of the formula: or the hydroquinone form thereof; or a solvate or hydrate thereof.

19 Claims, 38 Drawing Sheets

(56) References Cited

U.S. PATENT DOCUMENTS

| | | |
|---|---|---|
| 2012/0122934 A1 | 5/2012 | Jankowski et al. |
| 2012/0122969 A1 | 5/2012 | Miller et al. |
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0345312 A1 | 12/2013 | Jankowski et al. |
| 2014/0243424 A1 | 8/2014 | Mollard et al. |
| 2014/0249332 A1 | 9/2014 | Mollard |
| 2014/0256830 A1 | 9/2014 | Hinman et al. |
| 2014/0275045 A1 | 9/2014 | Hinman et al. |
| 2014/0275054 A1 | 9/2014 | Hinman et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2016/0024085 A1 | 1/2016 | Hinman et al. |
| 2016/0115141 A1 | 4/2016 | Hinman et al. |
| 2018/0000749 A1 | 1/2018 | Mollard et al. |
| 2018/0333389 A1 | 11/2018 | Miller |
| 2018/0362492 A1 | 12/2018 | Giannousis et al. |
| 2018/0370892 A1 | 12/2018 | Hinman et al. |
| 2019/0029975 A1 | 1/2019 | Shrader |
| 2019/0241497 A1 | 8/2019 | Hinman |
| 2019/0330159 A1 | 10/2019 | Kitano et al. |
| 2020/0121618 A1 | 4/2020 | Miller et al. |

FOREIGN PATENT DOCUMENTS

| | | |
|---|---|---|
| WO | WO 2011/113018 | 9/2011 |
| WO | WO 2012/154613 | 11/2012 |
| WO | WO 2012/170773 A1 | 12/2012 |
| WO | WO 2013/006736 | 1/2013 |
| WO | WO 2015/183963 | 12/2015 |
| WO | WO 2016/114860 | 7/2016 |
| WO | WO 2017/123823 | 7/2017 |
| WO | WO 2018/129411 | 7/2018 |
| WO | WO 2018/191732 A1 | 10/2018 |
| WO | WO 2020/081879 A1 | 4/2020 |
| WO | WO 2020/252414 A1 | 12/2020 |
| WO | WO 2021/077034 A1 | 4/2021 |

OTHER PUBLICATIONS

Alami, N. H. et al. "Axonal transport of TDP-43 mRNA granules is impaired by ALS-causing mutations", Neuron 81, 2014, pp. 536-543; doi:10.1016/j.neuron.2013.12.018.

Arai, T. et al. "TDP-43 is a Component of Ubiquitin-Positive Tau-Negative Inclusions in Frontotemporal Lobar Degeneration and amyotrophic laterial sclerosis" Biochemical and Biophysical Research Communications, 2006, 351, 602-611.

FIG. 1: Schematic representation of enantiotropic (left) and monotropic (right) phase diagram.

Foran, E et al. "Glutamate transporters and the excitotoxic path to motor neuron degeneration in amyotrophic lateral sclerosis", Antioxidants & Redox Signaling, 11(7), 2009; DOI: 10.1089=ars.2009.2444.

Giron, D., "Thelmal analysis and calorimetric methods in the characterisation, of polymorphs and solvates", Thermochimica acta 248, 1995, Elsevier Science B.V., pp. 1-59.

J. Garrido, Forma y estructura de los Cristales, Chapter V, p. 204-225—machine translation.

Gopal, P. et al. (2017). Amyotrophic lateral sclerosis-linked mutations increase the viscosity of liquid-like TDP-43 RNP granules in neurons. Proc. Natl Acad. Sci. USA 114, E2466-E2475 (2017).

Lagier-Tourenne, C. et al. "TDP-43 and FUS/TLS: emerging roles in RNA processing and neurodegeneration" Human Molecular Generics, 2010, 19, R46-R64.

Lagier-Tourenne, C. et al. "Divergent roles of ALS-linked proteins FUS/TLS and TDP-43 intersect in processing long pre-mRNAs", Nat. Neurosci, Nov. 15, 2012, (11) 1488-1497; doi:10.1038/nn.3230.

Ling, J. et. al. (2015). TDP-43 repression of nonconserved cryptic exons is compromised in ALS-FTD. Science, 349(6248):650.

Melamed, Z., et. al. (2019). Premature polyadenylation-mediated loss of stathmin-2 is a hallmark of TDP-43 dependent neurodegeneration. Nature Neuroscience, 22:180-190.

Nies and Spielberg, Principles of Therapeutics in "The Pharmacological Basis of Therapeutics" $9^{th}$ Ed Inter-American Ed, 1996, p. 47—machine translation.

Polymenidou, M. et al. (2011). Long pre-mRNA depletion and RNA missplicing contribute to neuronal vulnerability from loss of TDP-43. Nat. Neurosci. 14, 459-468 (2011).

Remington Practical Pharmacy (Remington's Pharmaceutical Sciences, 16th ed., Mack Pub. Co. Pennsylvania, 1980, pp. 180-181).

Response to Examation Report in EP Patent No. 1933821 filed Jul. 4, 2016.

Rothstein JD (1995). Excitotoxicity and neurodegeneration in amyotrophic lateral sclerosis. Clinical Neuroscience, 3(6):348-359.

Van Den Bosch, L et al (2006). The role of excitotoxicity in the pathogenesis of amyotrophic lateral sclerosis. Biochimica et Biophysica Acta, 1762(11-12):1068-1082.

International search report and written opinion of PCT/US2019/056836 dated Jun. 24, 2020.

Notification Concerning Transmittal Of International Preliminary Report On Patentability of PCT/US2019/056836 dated Apr. 14, 2021, 10 pages.

Translation of Appeal Brief in JP application No. 2015-55908 as filed Oct. 5, 2017; 20 pages.

Translation of Appeal Brief in JP application No. 2015-55909 as filed Mar. 6, 2017; 26 pages.

U.S. Appl. No. 16/989,753 Pending Claims, filed Jan. 19, 2021; 8 pages.

Chong et al., "Tau Proteins and Tauopathies in Alzheimer's Disease," Cellular and Molecular Neurobiology (2018) 38:965-980.

Shrader et al., "COQ10 Analogies Targeting Mitochondrial Impairment in Huntington's Disease," EHDN Annual Meeting: abstracts, J Neurol Neurosurg Psychiatry 2008; 79(Suppl 1); A7-A8.

Kalayci et al., "Effect of Coenzyme QIO on ischemia and neuronal damage in an experimental traumatic brain-injury model in rats," BMC Neuroscience, Jul. 29, 2011, vol. 12, No. 75, pp. 1-7.

Özalp et al., "The effect of coenzyme Q10 on venous ischemia reperfusion injury," Journal of Surgical Research, vol. 204, No. 2, May 7, 2016, pp. 304-310.

Asin-Cayuela et al., "Fine-tuning the hydrophobicity of a mitochondria-targeted antioxidant", FEBS Letters, 2004, vol. 571, pp. 9-16.

Bates et al., "Methoxymetacyclophanes from 2,6-Dimethylanisole," J. of Organic Chemistry, 1991, 56(5), pp. 1696-1699.

Fieser et al., "Alkylation of Para Quinones with Acyl Peroxides," Journal of the American Chemical Society, Sep. 1942, 64(9), pp. 2060-2065.

Hübscher et al., "Total Synthesis of Naturally Occurring α-Tocopheroi. Asymmetric Alkylation and Asymmetric Epoxidation as Means to Introduce (R)-Configuration at C(2) of the Chroman Moiety", Helvetica Chimica Acta 1990, 73(4), p. 1068.

Monte et al., "An Efficient Process for the Synthesis of $\gamma$-Arylbutanals via Copper-Mediated Grignard Coupling", Organic Process Research & Development, 2001, vol. 5, pp. 267-269.

Pelter et al., "Phenolic Oxidations with Phenyliodonium Diacetate", J. Chem. Soc., Perkin Trans. 1, 1993, vol. 16, p. 1891.

Shiraishi et al., "Novel Eicosanoid Antagonists: Synthesis and Pharmacological Evaluation" Journal of Medicinal Chemistry, 1989, 32(9), p. 2214.

Silbert et al., "Preparation of t-Butyl Peresters and Diacyl Peroxides of Aliphatic Monobasic Acids", Journal of the American Chemical Society, May 20, 1959, 81(10), p. 2364.

Sommer et al., "Stereospecific Coupling Reactions between Organolithium Reagents and Secondary Halides", J. Org. Chem., Jan. 1970, 35(1), pp. 22-25.

Thomas et al., "Repetitive Diels-Alder Reactions for the Growth of Linear Polyacenequinoid Derivatives", Journal of Organic Chemistry, 1986, 51(22), p. 4160.

(56) References Cited

OTHER PUBLICATIONS

Bieniek et al., "Tau Pathology in Frontotemporal Lobar Degeneration with C9ORF72 Hexanucleotide Repeat Expansion", Acta Neuropathol, Feb. 2013; 125(2): 289-302. doi:10.1007/s00401-012-1048-7.
He et al., "Amyotrophic Lateral Sclerosis-associated GGGGCC repeat expansion promotes Tau phosphorylation and toxicity", Neurobiology of Disease 130 (2019) 104493.
Hirano et al., Neuropathology of amyotrophic lateral sclerosis and parkinsonism-dementia complex on Guam. In: Luthy L, Bischoff A, editors. Proceedings of the Fifth International Congress of Neuropathology. Amsterdam: Excerpta Medica (1966). p. 190-4; Hirano A, et al., Arch Neurol. (1966) 15:35-51.
King et al., "Mixed tau, TDP-43 and p62 pathology in FTLD associated with a C9ORF72 repeat expansion and p.Ala239Thr MAPT(tau) variant", Acta Neuropathol, published online: Sep. 28, 2012; DOI 10.1007/s00401-012-1050-0.
Lillo et al., "Amyotrophic lateral sclerosis and frontotemporal dementia: A behavioural and cognitive continuum", Informa Healthcare, Amyotrophic Lateral Sclerosis, 2012, vol. 13, pp. 102-109; DOI: 10.3109/17482968.2011.639376.
Moszczynski et al., "Pathologic $Thr^{175}$ tau phosphorylation in CTE and CTE with ALS", Neurology® 2018;90:e380-e387; doi:10.1212/WNL.0000000000004899.
Vintilescu et al., "The neurotoxic $tau_{45-230}$ Fragment Accumulates in upper and Lower Motor neurons in Amyotrophic Lateral sclerosis subjects", Molecular Medicine, 2016, vol. 22, pp. 477-486; doi: 10.2119/molmed.2016.00095.
Yang et al., "Microtubule-associated tau protein positive neuronal and glial inclusions in ALS", Neurology, vol. 61, Dec. 2003, pp. 1766-1773; DOI 10.1212/01.WNL.0000099372.75786.F8.
Yang et al., "Tau protein aggregation in the frontal and entorhinal cortices as a function of aging", Developmental Brain Research, 2005, vol. 156, pp. 127-138.
Yang et al., "Widespread neuronal and glial hyperphosphorylated tau deposition in ALS with cognitive impairment", Amyotrophic Lateral Sclerosis, 2012, vol. 13 (2), pp. 178-193; DOI: 10.3109/17482968.2011.622405.

2,3,5-TRIMETHYL-6-NONYLCYCLOHEXA-2,5-DIENE-1,4-DIONE FOR SUPPRESSING AND TREATING ALPHA-SYNUCLEINOPATHIES, TAUOPATHIES, AND OTHER DISORDERS

This application is a continuation of U.S. patent application Ser. No. 17/218,042, filed on Mar. 30, 2021, which is a continuation of International Patent Application PCT/US19/56836, filed on Oct. 17, 2019, which claims priority to, and the benefit of, U.S. Provisional Patent Application No. 62/747,080, filed Oct. 17, 2018, entitled 2,3,5-TRIMETHYL-6-NONYLCYCLOHEXA-2,5-DIENE-1,4-DIONE FOR SUPPRESSING AND TREATING ALZHEIMER'S DISEASE AND OTHER DISORDERS, and U.S. Provisional Patent Application No. 62/771,570, filed Nov. 26, 2018, entitled 2,3,5-TRIMETHYL-6-NONYLCYCLOHEXA-2,5-DIENE-1,4-DIONE FOR SUPPRESSING AND TREATING ALZHEIMER'S DISEASE AND OTHER DISORDERS, the contents of both of which are herein incorporated by reference in their entirety for all purposes.

BACKGROUND

U.S. Publication No. 2007/0072943 describes certain quinone compounds, and methods of treating certain mitochondrial disorders. U.S. Publication No. 2010/0063161 describes the compound 2,3,5-trimethyl-6-nonylcyclohexa-2,5-diene-1,4-dione, and methods for treating pervasive developmental disorders and Attention Deficit Hyperactivity Disorder (ADHD).

What is needed are improved methods for treating or suppressing certain disorders, including α-synucleinopathies, tauopathies, ALS, traumatic brain injury, and ischemic-reperfusion related injuries. What is further needed are compounds having superior brain penetration and/or preferential partitioning into the brain versus other areas of the body (such as plasma).

In addition, what is needed is a stable polymorph of 2,3,5-trimethyl-6-nonylcyclohexa-2,5-diene-1,4-dione and particles thereof which can be used in pharmaceutical compositions; the manufacture of pharmaceutical compositions; and in methods for treating or suppressing disorders, including for treating or suppressing α-synucleinopathies, tauopathies, ALS, traumatic brain injury, and ischemic-reperfusion related injuries.

SUMMARY

In one aspect of the invention is a method of treating or suppressing a disorder selected from the group consisting of an α-synucleinpathy, a tauopathy, Amyotrophic lateral sclerosis (ALS), traumatic brain injury, and ischemic-reperfusion related injury, comprising administering to a subject in need thereof a therapeutically effective amount of a compound of the formula:

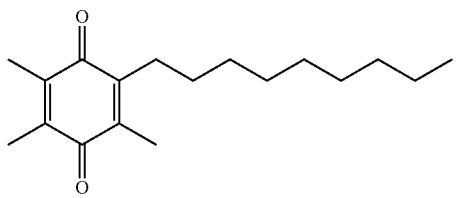 [SMILES: CCCCCCCCCC1=C(C)C(=O)C(C)=C(C)C1=O]

or the hydroquinone form thereof; or a solvate or hydrate thereof. In some embodiments, the compound is not a solvate or hydrate. In some embodiments, including any of the foregoing embodiments, the compound is in the quinone form. In some embodiments, including any of the foregoing embodiments, the compound is in the hydroquinone form. In some embodiments, including any of the foregoing embodiments, the method is for treating or suppressing an α-synucleinpathy. In some embodiments, including any of the foregoing embodiments, the α-synucleinpathy is selected from the group consisting of: Parkinson's Disease, Parkinson's Disease with dementia (PDD), multisystem atrophy (MSA), Frontotemporal Dementia, Dementia with Lewy Bodies (DLB), Gaucher's disease (GD), Neurodegeneration with Brain Iron Accumulation (NBIA), and neuroaxonal dystrophies (PLA2G6-associated neurodegeneration). In some embodiments, including any of the foregoing embodiments, the Parkinson's Disease is genetic. In some embodiments, including any of the foregoing embodiments, the Parkinson's Disease is idiopathic. In some embodiments, including any of the foregoing embodiments, the method for suppressing or treating Parkinson's Disease is that wherein the patient has a mutation in one or more of the following genes: MAPT (Microtubule-associated protein tau), PRKN (parkin), PINK1 (PINK1), LRRK2 (leucine-rich repeat kinase 2), GBA (glucocerebrosidase), SNCA (alpha synuclein), PARK7 (DJ-1), and/or UCHL1 (ubiquitin carboxyl-terminal esterase L1). In some embodiments, including any of the foregoing embodiments, the method is for treating or suppressing a tauopathy. In some embodiments, including any of the foregoing embodiments, the tauopathy is selected from the group consisting of: Alzheimer's disease, dementia pugilistica, Guam Amyotrophic lateral sclerosis-Parkinsonism-Dementia (Guam ALS/PD), Pick Disease, Argyrophilic grain dementia, Nieman-Pick type C, Subacute sclerosing panencephalitis (SSPE), Progressive supranuclear palsy (PSP), multisystem atrophy (MSA), Corticobasoganlionic degeneration, Frontotemporal dementia with parkinsonism-17 (FTDP-17), Postencephalitic Parkinsonism (PEP), and Autosomal recessive Parkinsonism. In some embodiments, including any of the foregoing embodiments, the method is for treating or suppressing Alzheimer's Disease. In some embodiments, including any of the foregoing embodiments, the method is for treating or suppressing Parkinson's Disease. In some embodiments, including any of the foregoing embodiments, the method is for treating or suppressing traumatic brain injury. In some embodiments, including any of the foregoing embodiments, the method is for treating or suppressing ischemic-reperfusion related injury. In some embodiments, including any of the foregoing embodiments, the method is for treating or suppressing stroke. In some embodiments, including any of the foregoing embodiments, the method is for treating or suppressing Amyotrophic lateral sclerosis (ALS). In some embodiments, including any of the foregoing embodiments, the method is for treating the disorder. In some embodiments, including any of the foregoing embodiments, the method is for suppressing the disorder. In some embodiments, including any of the foregoing embodiments, the compound is administered orally. In some embodiments, including any of the foregoing embodiments, the compound is administered intravenously.

In another aspect is a method of treating or suppressing a disorder selected from the group consisting of Alzheimer's Disease, Parkinson's Disease, traumatic brain injury, and ischemic-reperfusion related injuries, comprising administering to a subject in need thereof a therapeutically effective amount of a compound of the formula:

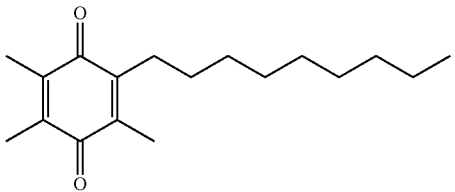

or the hydroquinone form thereof; or a solvate or hydrate thereof. In some embodiments, the compound is:

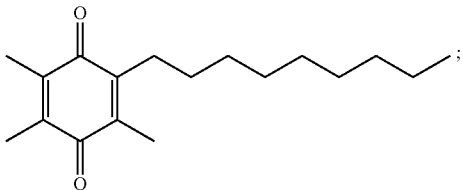 [SMILES: CCCCCCCCCC1=C(C)C(=O)C(C)=C(C)C1=O]

or the hydroquinone form thereof. In some embodiments, including any of the foregoing embodiments, the compound is in the quinone form. In some embodiments, including any of the foregoing embodiments, the compound is in the hydroquinone form. In some embodiments, the method is for suppressing or treating Alzheimer's Disease. In some embodiments, the method is for suppressing or treating Parkinson's Disease. In some embodiments, the method for suppressing or treating Parkinson's Disease includes treating or suppressing idiopathic Parkinson's Disease. In some embodiments, the method for suppressing or treating Parkinson's Disease includes treating or suppressing familial (i.e. genetic) Parkinson's Disease. In some embodiments, the method for suppressing or treating Parkinson's Disease is that wherein the patient has a mutation in one or more of the following genes: MAPT (Microtubule-associated protein tau), PRKN (parkin), PINK1 (PINK1), LRRK2 (leucine-rich repeat kinase 2), GBA (glucocerebrosidase), SNCA (alpha synuclein), PARK7 (DJ-1), and/or UCHL1 (ubiquitin carboxyl-terminal esterase L1). In some embodiments, the method is for suppressing or treating traumatic brain injury. In some embodiments, the method is for suppressing or treating an ischemic-reperfusion related injury. In some embodiments, the ischemic-reperfusion related injury is a stroke. In some embodiments, the ischemic-reperfusion related injury is ischemic reperfusion-related retinal injury. In some embodiments, including any of the foregoing embodiments, the compound is administered orally. In some embodiments, including any of the foregoing embodiments, the compound is administered by injection. In some embodiments, including any of the foregoing embodiments, the compound is administered intravenously. In some embodiments, including any of the foregoing embodiments, the method is a method of suppressing the disorder. In some embodiments, including any of the foregoing embodiments, the method is a method of treating the disorder.

In another aspect is a polymorph of an anhydrate of 2,3,5-trimethyl-6-nonylcyclohexa-2,5-diene-1,4-dione, wherein a powder X-ray diffraction pattern for the polymorph comprises characteristic peaks at least at the following angular positions, wherein the angular positions may vary by ±0.2: 4.10, 12.12, and 16.14. In some embodiments, the data are obtained with a Cu Kα1 source, a wavelength of 1.540598 Å, and a temperature of 23-25° C. In some embodiments, the polymorph comprises characteristic peaks at least at the following angular positions, wherein the angular positions may vary by ±0.2: 4.10, 11.77, 12.12, and 16.14. In some embodiments, the polymorph comprises characteristic peaks at least at the following angular positions, wherein the angular positions may vary by ±0.2: 4.10, 11.77, 12.12, 16.14, and 22.41. In some or any embodiments, a powder X-ray diffraction pattern for the polymorph comprises characteristic peaks at least at one of the following angular positions, wherein the angular positions may vary by ±0.2: 4.10, 11.77, 12.12, 16.14, and 22.41. In some or any embodiments, a powder X-ray diffraction pattern for the polymorph comprises characteristic peaks at least at two of the following angular positions, wherein the angular positions may vary by ±0.2: 4.10, 11.77, 12.12, 16.14, and 22.41. In some or any embodiments, a powder X-ray diffraction pattern for the polymorph comprises characteristic peaks at least at two of the following angular positions, wherein the angular positions may vary by ±0.2: 4.10, 11.77, 12.12, and 16.14. In some or any embodiments, a powder X-ray diffraction pattern for the polymorph comprises characteristic peaks at least at two of the following angular positions, wherein the angular positions may vary by ±0.2: 4.10, 12.12, and 16.14. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the polymorph has a powder x-ray diffraction pattern substantially as shown in any one of FIGS. 5, 11, 14, and 16. In some embodiments, including any of the foregoing embodiments, the polymorph has a differential scanning calorimetry (DSC) thermogram substantially as shown in FIG. 7. In some embodiments, including any of the foregoing embodiments, a DSC thermogram has a single endothermic peak at about 47° C. to about 53° C. In some embodiments, including any of the foregoing embodiments, a DSC thermogram has a single endothermic peak at about 49° C. to about 53° C. In some embodiments, including any of the foregoing embodiments, a DSC thermogram has a single endothermic peak at about 50° C. to about 52° C. In some embodiments, including any of the foregoing embodiments, a DSC thermogram has a single endothermic peak at about 50.5° C. In some embodiments, including any of the foregoing embodiments, the polymorph has a thermogravimetric analysis (TGA) thermogram substantially as shown in FIG. 8. In some embodiments, including any of the foregoing embodiments, the polymorph has a $^1$H NMR spectrum substantially as shown in FIG. 6. In some embodiments, including any of the foregoing embodiments, at least about 95% by mole of the 2,3,5-trimethyl-6-nonylcyclohexa-2,5-diene-1,4-dione is the polymorph, exclusive of any solvents, carriers or excipients. In some embodiments, including any of the foregoing embodiments, at least about 99% by mole of the 2,3,5-trimethyl-6-nonylcyclohexa-2,5-diene-1,4-dione is the polymorph, exclusive of any solvents, carriers or excipients. In some embodiments, including any of the foregoing embodiments, at least about 95% a/a as measured by HPLC of the composition is the 2,3,5-trimethyl-6-nonylcyclohexa-2,5-diene-1,4-dione, exclusive of any solvents, carriers or excipients. In some embodiments, including any of the foregoing embodiments, at least about 99% a/a as measured by HPLC of the composition is the 2,3,5-trimethyl-6-nonylcyclohexa-2,5-diene-1,4-dione, exclusive of any solvents, carriers or excipients. In some embodiments, including any of the foregoing embodiments, the potency of the 2,3,5-trimethyl-6-nonylcyclohexa-2,5-diene-1,4-dione is at least about 95%. In some embodiments, including any of the foregoing embodiments, the potency of the 2,3,5-trimethyl-6-nonylcyclohexa-2,5-diene-1,4-dione is at least about 99%. In some embodiments, including any of the foregoing embodiments, the polymorph is present as a plurality of particles, wherein the particles have a ratio of D90:D10 less than about 11:1. In some embodiments, including any of the foregoing embodiments, the polymorph is present as a plurality of particles, wherein the particles have a ratio of D90:D10 less than about 7:1. In some embodiments, including any of the foregoing embodiments, the polymorph was recrystallized by a solvent comprising about 75-85% IPA/water. In some embodiments, including any of the foregoing embodiments, the polymorph was recrystallized by a solvent comprising about 80-85% IPA/water. In some embodiments, including any of the foregoing embodiments, the polymorph was recrystallized by a solvent comprising about 85% IPA/water.

In another aspect of the invention is a pharmaceutical composition comprising the polymorph as described herein, or a composition as described herein, and a pharmaceutically acceptable solvent, carrier, or excipient, or a pharmaceutical composition prepared with the polymorph as described herein, or a composition as described herein, and a pharmaceutically acceptable solvent, carrier, or excipient.

In another aspect is a method of treating or suppressing an α-synucleinpathy, a tauopathy, Amyotrophic lateral sclerosis (ALS), traumatic brain injury, or ischemic-reperfusion related injury, comprising administering to an individual in need thereof a therapeutically effective amount of the polymorph described herein, or a composition as described herein.

In another aspect is a method of recrystallizing 2,3,5-trimethyl-6-nonylcyclohexa-2,5-diene-1,4-dione from a composition, comprising: a) contacting the composition with IPA and water such that the resulting ratio of IPA to water is about 75-87% isopropanol (IPA)/25-13% water (v:v), at a temperature of about 40-45° C.; b) cooling the mixture to about 32° C.; and c) filtering the 2,3,5-trimethyl-6-nonylcyclohexa-2,5-diene-1,4-dione from the mixture. In some embodiments, step (a) comprises: a1) contacting the composition with IPA; a2) warming the mixture to about 40-45° C.; and a3) adding water to the mixture such that the ratio of IPA to water is about 75-85% IPA:25-15% water (v:v). In some embodiments, including any of the foregoing embodiments, step (a) comprises stirring to dissolve the composition. In some embodiments, including any of the foregoing embodiments, the ratio of IPA:water is about 80-85% IPA:20-15% water (v:v). In some embodiments, including any of the foregoing embodiments, the ratio of IPA:water is about 85% IPA:15% water (v:v). In some embodiments, including any of the foregoing embodiments, step (a3) comprises returning the temperature of the mixture to about 40-45° C. In some embodiments, including any of the foregoing embodiments, the method comprising polish filtering the mixture after step (a). In some embodiments, including any of the foregoing embodiments, step (b) comprises cooling to about 32° C. over about 2-10 hours. In some embodiments, including any of the foregoing embodiments, step (b) comprises cooling to about 32° C. over about 6 hours. In some embodiments, including any of the foregoing embodiments, the method comprises a step (b1) after step (b), comprising holding the mixture at about 32° C. for about 2-24 hours. In some embodiments, including any of the foregoing embodiments, the method comprises a step (b1) after step (b), comprising holding the mixture at about 32° C. for about 6 hours. In some embodiments, including any of the foregoing embodiments, the method comprises a step (b2) after step (b) or (1)1), when present, comprising cooling the mixture to about 0° C. In some embodiments, including any of the foregoing embodiments, step (b2) comprises cooling the mixture to about 0° C. over about 3-24 hours. In some embodiments, including any of the foregoing embodiments, step (b2) further comprises holding the mixture at about 0° C. for about one hour.

In another aspect is a composition comprising 2,3,5-trimethyl-6-nonylcyclohexa-2,5-diene-1,4-dione as made according to a method of the immediately preceding paragraph.

In another aspect is a method of making a pharmaceutical composition, comprising converting the polymorph as described in any one of the preceding paragraphs, or the composition of any one of the preceding paragraphs, to a liquid or emulsion form. In some embodiments, the pharmaceutical composition is provided as an oral solution, a liquid-filled capsule, or an injectable solution. Pharmaceutical composition produced according to these methods are provide.

In another aspect is a metastable melted amorphous form of 2,3,5-trimethyl-6-nonylcyclohexa-2,5-diene-1,4-dione, having an XRPD plot substantially as shown in FIG. 31.

In one aspect is a method of treating or suppressing a disorder selected from the group consisting of Alzheimer's Disease, Parkinson's Disease, traumatic brain injury, and ischemic-reperfusion related injuries, comprising administering to a subject in need thereof a therapeutically effective amount of a compound of the formula:

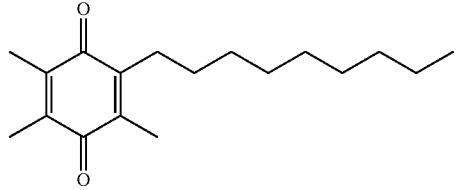 [SMILES: CCCCCCCCCC1=C(C)C(=O)C(C)=C(C)C1=O]

or the hydroquinone form thereof; or a solvate or hydrate thereof. In some embodiments, the compound is:

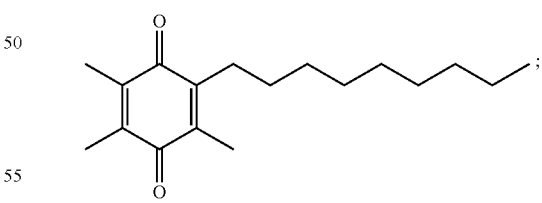

or the hydroquinone form thereof. In some embodiments, including any of the foregoing embodiments, the compound is in the quinone form. In some embodiments, including any of the foregoing embodiments, the compound is in the hydroquinone form. In some embodiments, the method is for suppressing or treating Alzheimer's Disease. In some embodiments, the method is for suppressing or treating Parkinson's Disease. In some embodiments, the method for suppressing or treating Parkinson's Disease includes treating or suppressing idiopathic Parkinson's Disease. In some embodiments, the method for suppressing or treating Parkinson's Disease includes treating or suppressing familial (i.e. genetic) Parkinson's Disease. In some embodiments, the method for suppressing or treating Parkinson's Disease is that wherein the patient has a mutation in one or more of the following genes: MAPT (Microtubule-associated protein tau), PRKN (parkin), PINK1 (PINK1), LRRK2 (leucine-rich repeat kinase 2), GBA (glucocerebrosidase), SNCA (alpha synuclein), PARK7 (DJ-1), and/or UCHL1 (ubiquitin carboxyl-terminal esterase L1). In some embodiments, the method is for suppressing or treating traumatic brain injury. In some embodiments, the method is for suppressing or treating an ischemic-reperfusion related injury. In some embodiments, the ischemic-reperfusion related injury is a stroke. In some embodiments, the ischemic-reperfusion related injury is ischemic reperfusion-related retinal injury. In some embodiments, including any of the foregoing embodiments, the compound is administered orally. In some embodiments, including any of the foregoing embodiments, the compound is administered by injection. In some embodiments, including any of the foregoing embodiments, the compound is administered intravenously. In some embodiments, including any of the foregoing embodiments, the method is a method of suppressing the disorder. In some embodiments, including any of the foregoing embodiments, the method is a method of treating the disorder.

Any one or more of the compounds described herein, including all of the foregoing compounds, can be used in a composition comprising a pharmaceutically acceptable carrier, pharmaceutically acceptable excipient, or pharmaceutically acceptable vehicle. In some embodiments, the composition is formulated for internal use. Any one or more of the compounds described herein, including all of the foregoing compounds, can be formulated into a unit dose formulation.

For all the compounds, compositions, formulations and methods described herein, any compound in the quinone form can also be used in its reduced form (hydroquinone) when desired. That is, the compounds recited herein as cyclohexadienedione compounds (oxidized quinone) form can also be used in their benzenediol (reduced hydroquinone) form as desired.

For all compounds, compositions, and formulations described herein, and all methods using a compound or composition or formulation described herein, the compounds or compositions can either comprise the listed components or steps, or can "consist essentially of" the listed components or steps, or can "consist of" the listed components or steps. That is, the transitional phrase "comprising" or "comprises" can be replaced by the transitional phrase "consisting essentially of" or "consists essentially of." Alternatively, the transitional phrase "comprising" or "comprises" can be replaced, in some or any embodiments, by the transitional phrase "consisting of" or "consists of." When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, excipients, or diluents and other such components which do not substantially affect the condition being treated.

DETAILED DESCRIPTION

Figure 1A:
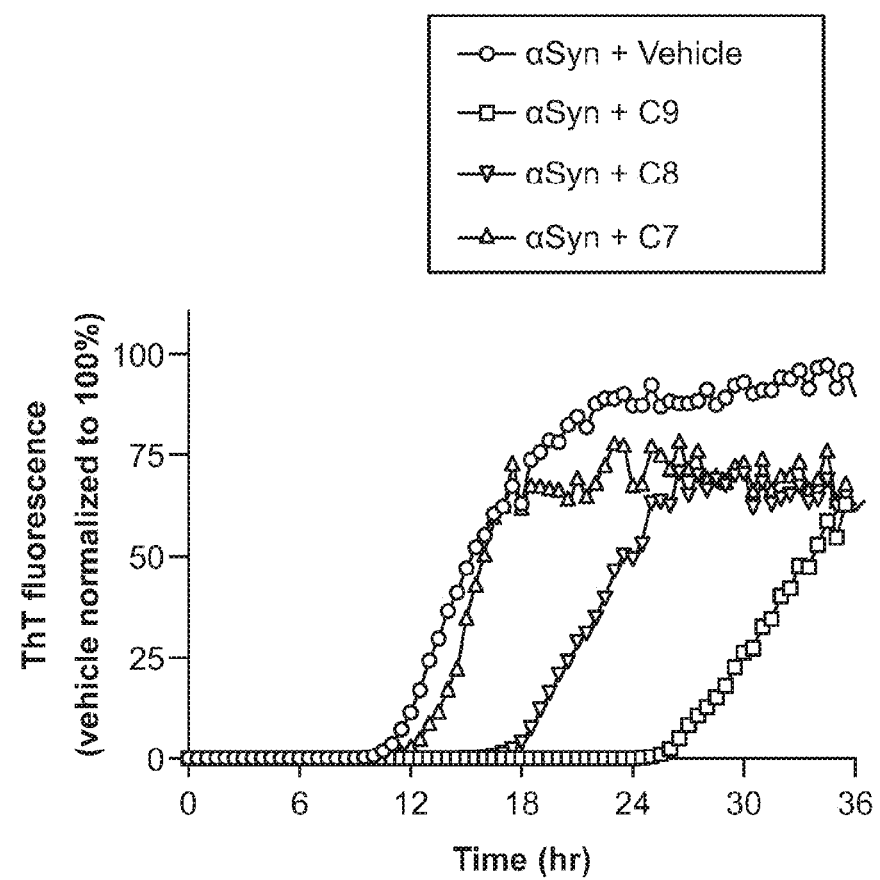
FIG. 1A shows the kinetics of recombinant human αSynuclein (αSyn) aggregation in the presence of the compound 2,3,5-trimethyl-6-nonylcyclohexa-2,5-diene-1,4-dione ("C9"), 2,3,5-trimethyl-6-octylcyclohexa-2,5-diene-1,4-dione ("C8"), 2,3,5-trimethyl-6-heptylcyclohexa-2,5-diene-1,4-dione ("C7"), or vehicle only, at a sub-stoichiometric ratio.

The present invention provides compounds, compositions, and methods for treating or suppressing α-synucleinopathies, tauopathies, ALS, traumatic brain injury, and ischemic-reperfusion related injuries. α-Synucleinopathies are neurodegenerative diseases characterized by the abnormal accumulation of aggregates of alpha-synuclein protein in neurons, nerve fibres or glial cells. Tauopathies belongs to a class of neurodegenerative diseases associated with the pathological aggregation of tau protein in neurofibrillary or gliofibrillary tangles in the human brain, such as Alzheimer's Disease (see e.g. Cellular and Molecular Neurobiology (2018) 38:965-980). As shown in the Examples, a claimed compound has demonstrated efficacy in reducing aggregates of alpha-synuclein protein, and in reducing aggregation of tau protein. Without wishing to be bound by theory, for the claimed diseases, it may be beneficial to have penetration of drug into the brain, and in addition, it may be beneficial to have the drug preferentially partition into the brain versus other tissues. For example, this may reduce off-target and side effects. Applicants have surprisingly found that a claimed compound has superior brain penetration and superior partitioning of the compound into the brain versus the plasma.

The present invention further provides a solid form of the compound 2,3,5-trimethyl-6-nonylcyclohexa-2,5-diene-1,4-dione, compositions comprising the solid form at higher purity and with preferred characteristics such as more preferred particle morphology and particle size distribution, and processes for making the same. As shown in more detail in the detailed description, the experimental section and the figures provided herein, the compositions have beneficial properties such as improved purity (e.g. lower silver content), improved handling characteristics (e.g. flowability), and improved ability to be formulated into pharmaceuticals (e.g. improved ability to be milled). The particles have good flow and morphology properties compared to an earlier process. The use of the present particles facilitates the drug product manufacture, for instance capsule filling. In addition, using the present particles, it may be possible to reduce the amount of excipients needed for the drug product manufacture which offers advantages in terms of cost, time and process efficiency. Indeed, if a drug substance is sticky or does not flow easily, more excipients may be needed to improve the handling of said drug substance. Also if drug substance milling is needed, the sticky material would have yield losses due to losses on surfaces of milling equipment, and also the milled product would form more, or harder to break, agglomerates. These characteristics are not desirable in processing for drug product manufacture and are improved in the described process.

The abbreviations used herein have their conventional meaning within the chemical and biological arts, unless otherwise specified.

Reference to "about" a value or parameter herein includes (and describes) variations that are directed to that value or parameter per se. For example, description referring to "about X" includes description of "X".

As used herein, and unless otherwise specified, the terms "about" and "approximately," when used in connection with various terms such as temperatures, doses, amounts, or weight percent of ingredients of a composition or a dosage form, mean e.g. a temperature, dose, amount, or weight percent that is recognized by those of ordinary skill in the art to provide an effect equivalent to that obtained from the specified temperature dose, amount, or weight percent. Specifically, the terms "about" and "approximately," when used in this context, contemplate a temperature, dose, amount, or weight percent, etc. within 15%, within 10%, within 5%, within 4%, within 3%, within 2%, within 1%, or within 0.5% of the specified temperature, dose, amount, or weight percent, etc.

The terms "a" or "an," as used in herein means one or more, unless the context clearly dictates otherwise.

By "subject," "individual," or "patient" is meant an individual organism, preferably a vertebrate, more preferably a mammal, most preferably a human.

"Treating" a disorder with the compounds and methods discussed herein is defined as administering one or more of the compounds discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the compounds and methods discussed herein is defined as administering one or more of the compounds discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. In some embodiments, genetic screening can be used to identify patients at risk of the disorder. The compounds and methods disclosed herein can then be administered to asymptomatic patients at risk of developing the clinical symptoms of the disorder, in order to suppress the appearance of any adverse symptoms.

"Therapeutic use" of the compounds discussed herein is defined as using one or more of the compounds discussed herein to treat or suppress a disorder, as defined herein. A "therapeutically effective amount" of a compound is an amount of the compound, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations.

"2,3,5-trimethyl-6-nonylcyclohexa-2,5-diene-1,4-dione" and "C9" are used interchangeably herein.

"2,3,5-trimethyl-6-octylcyclohexa-2,5-diene-1,4-dione" and "C8" are used interchangeably herein.

"2,3,5-trimethyl-6-heptylcyclohexa-2,5-diene-1,4-dione" and "C7" are used interchangeably herein.

"Hydroquinone form" indicates the form of the compound when a two electron reduction of the quinone ring is effected, providing a net conversion of the two oxo groups to two hydroxy groups. For example, the hydroquinone form of the quinone compound:

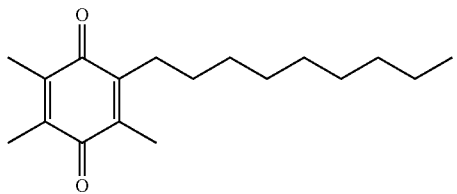 [SMILES: CCCCCCCCCC1=C(C)C(=O)C(C)=C(C)C1=O]

is the following:

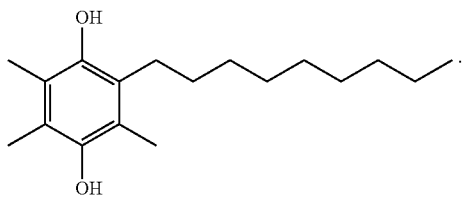 [SMILES: CCCCCCCCCc1c(C)c(O)c(C)c(C)c1O]

"alpha-synuclein" and "α-synuclein" are used interchangeably herein.

The description of compounds herein also includes all isotopologues, in some embodiments, partially deuterated or perdeuterated analogs of all compounds herein.

Ischemic-reperfusion related injuries include, but are not limited to, stroke and ischemic reperfusion-related retinal injury.

"Stroke" includes ischemic stroke (non-limiting examples include thrombotic stroke, embolic stroke), hemorrhagic stroke (non-limiting examples include intracerebral hemorrhage, subarachnoid hemorrhage), and transient ischemic attack. In some embodiments, the stroke is an ischemic stroke. In some embodiments, the stroke is a hemorrhagic stroke. In some embodiments, the stroke is a transient ischemic attack.

For all characterization data described in the claims herein (e.g. XRPD peaks, DSC, TGA, particle size distribution, etc.), in some embodiments the data are obtained by a method performed substantially as described herein (for example, for XRPD, DSC, and TGA, see e.g. Example 7 for specific methodology). "Substantially as described herein" indicates that one skilled in the art would use a method that is recognized by those of ordinary skill in the art to provide a result substantially equivalent to that obtained from the specified method.

Pharmaceutical Formulations

For the claimed crystalline form, residual solvents are within permissible limits, making them well suited for formulation into pharmaceutical compositions. A solid state form also allows for ease of purification via crystallization techniques. The claimed crystalline form is not hygroscopic nor is it a hydrate/solvate, which means it does not require special handling regarding humidity exposure. In addition, improved morphology resulting from the recrystallization process enables easier handling during manufacture (such as described in more detail herein). The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, in some embodiments, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic effect.

Pharmaceutical compositions containing the compounds of the invention may be in any form suitable for the intended method of administration, including, in some embodiments, a solution, a suspension, or an emulsion. Liquid carriers are typically used in preparing solutions, suspensions, and emulsions. Liquid carriers contemplated for use in the practice of the present invention include, in some embodiments, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, in some embodiments, monohydric alcohols, such as ethanol, and polyhydric alcohols, such as glycols. Suitable oils include, in some embodiments, sesame oil, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, in some embodiments, a biodegradable material that can degrade spontaneously in situ and in vivo, in some embodiments, by hydrolysis or enzymatic cleavage, e.g., by proteases. The delivery system may be, in some embodiments, a naturally occurring or synthetic polymer or copolymer, in some embodiments, in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. In some embodiments, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. Formulations for topical administration may include lotions, tinctures, creams, emulsions, ointments, sprays, gels, and the like, and may further be formulated in other suitable formulations such as sunscreens, moisturizing lotions and creams, facial gels and creams, etc. In these compositions, the active product is mixed with one or more inert excipients including, for example, water, acetone, ethanol, ethylene glycol, propylene glycol, butane 1,3 diol, isopropyl myristate, isopropyl palmitate, mineral oil, and mixtures thereof. Topical administration may also involve the use of transdermal administration such as transdermal patches or iontophoresis devices. The term parenteral as used herein includes subcutaneous, intravenous, intramuscular, and intrasternal injection or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. Topical administration is another preferred route of administration, and formulations suitable for topical administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. Additional methods of administration are known in the art.

The compositions for topical administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

Injectable preparations, in some embodiments, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, in some embodiments, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

The formulations of the present invention may comprise two or more compounds or compositions as described herein.

The invention also provides articles of manufacture and kits comprising any one or more of the compounds of the invention, for use in any of the methods described herein.

The amount of active ingredient that may be combined with the carrier materials to produce a single dosage form will vary depending upon the host to which the active ingredient is administered and the particular mode of administration. It will be understood, however, that the specific dose level for any particular individual will depend upon a variety of factors including the activity of the specific compound employed, the age, body weight, body area, body mass index (BMI), general health, sex, and diet of the patient; time of administration, route of administration, rate of excretion, or drug combination; and the type, progression, and severity of the particular disease or condition. The pharmaceutical unit dosage chosen may be fabricated and administered to provide a defined final concentration of drug in the targeted region of the body. The therapeutically effective amount for a given situation can be readily determined by routine experimentation and is within the skill and judgment of the ordinary clinician.

The single or multiple dosages which can be used include an amount independently selected from about 0.1 mg/kg to about 600 mg/kg body weight, or about 1.0 mg/kg to about 500 mg/kg body weight, or about 1.0 mg/kg to about 400 mg/kg body weight, or about 1.0 mg/kg to about 300 mg/kg body weight, or about 1.0 mg/kg to about 200 mg/kg body weight, or about 1.0 mg/kg to about 100 mg/kg body weight, or about 1.0 mg/kg to about 50 mg/kg body weight, or about 1.0 mg/kg to about 30 mg/kg body weight, or about 1.0 mg/kg to about 10 mg/kg body weight, or about 10 mg/kg to about 600 mg/kg body weight, or about 10 mg/kg to about 500 mg/kg body weight, or about 10 mg/kg to about 400 mg/kg body weight, or about 10 mg/kg to about 300 mg/kg body weight, or about 10 mg/kg to about 200 mg/kg body weight, or about 10 mg/kg to about 100 mg/kg body weight, or about 50 mg/kg to about 150 mg/kg body weight, or about 100 mg/kg to about 200 mg/kg body weight, or about 150 mg/kg to about 250 mg/kg body weight, or about 200 mg/kg to about 300 mg/kg body weight, or about 250 mg/kg to about 350 mg/kg body weight, or about 200 mg/kg to about 400 mg/kg body weight, or about 300 mg/kg to about 400 mg/kg body weight, or about 250 mg/kg to about 300 mg/kg body weight, or about 300 mg/kg body weight. Compounds of the present invention may be administered in a single daily dose, or the total daily dosage may be administered in divided dosage of two, three or four times daily.

Single or multiple doses can be administered. In some embodiments, the dose is administered once, twice, three times, four times, five times, or six times. In some embodiments, the dose is administered once per day, twice per day, three times per day, or four times per day. In some embodiments, the dose is administered every hour, every two hours, every three hours, every four hours, every 6 hours, every 12 hours, or every 24 hours.

While the compounds of the invention can be administered as the sole active pharmaceutical agent, they can also be used in combination with one or more other agents used in the treatment of or suppression of the disorders described here. In some embodiments, the compound(s) of the invention are administered as the sole active pharmaceutical agent that is present in a therapeutically effective amount.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents or prophylactically effective agents can be administered at the recommended maximum clinical dosage or at lower doses. Dosage levels of the active compounds in the compositions of the invention may be varied so as to obtain a desired response depending on the route of administration, severity of the disorder and the response of the individual. When administered in combination with other therapeutic or prophylactic agents, the therapeutic agents or prophylactic agents can be formulated as separate compositions that are given at the same time or different times, or the therapeutic agents or prophylactic agents can be given as a single composition.

Preparation of Compounds of the Invention

The compounds of this invention can be prepared from readily available starting materials using general methods and procedures that will be apparent to one skilled in the art in view of the disclosure provided herein. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Solutions of C9 are light sensitive; room lighting should ideally be filtered to remove wavelengths <450 nm (amber light filters) . If amber lighting is not available, then appropriate controls should be used to minimize solutions to light exposure e.g. aluminum foil wrapping, amber glassware For all of the compounds and methods described herein, the quinone form can also be used in its reduced (hydroquinone) form when desired. Likewise, the hydroquinone form can also be used in its oxidized (quinone) form when desired. The reduced (hydroquinone) form may readily be converted to the oxidized (quinone) form using methods known in the art. See, e.g., air, silica Miller et al PCT Intl Appl 2006130775 7 Dec. 2006. The oxidized (quinone) form may readily be converted to the reduced hydroquinone form using methods known in the art. See, e.g., Zn, AcOH Fuchs et al EJOC 6 (2009) 833-40.

The invention is further described by the following non-limiting examples and embodiments.

Recrystallization. As shown in Examples 1A and 3A, synthetic methods for making C9 resulted in product that had one or more undesired characteristics, such as high silver content, stickiness of product, and undesired particle sizes and distribution. Generally, for pharmaceutical uses, it is preferred to have product solid with a narrow particle size distribution. Stickiness of the product in Example 3A made the product difficult to handle, including making milling difficult and sieving not possible.

Recrystallization may results in improved properties, e.g. removing impurities from the product solid and producing material of more homogeneous size and distribution to improve product performance during subsequent formulation. As shown in the Examples, a recrystallization procedure was discovered that resulted in improving the quality of the product solid, including, e.g.: improved purity, higher melting point, lower silver content, better flowability, less stickiness, and more homogeneous particle size and distribution. Furthermore, the recrystallization method did not require seed crystals or have issues with the oiling out of the C9.

The recrystallization procedure generally comprises dissolving C9 in a solvent, warming the mixture to about 40-45° C. in order to dissolve the C9, cooling the mixture to about 32° C. where crystallization occurs, and filtering the product.

In some embodiments, the recrystallization solvent is about 75-85% IPA/water. In some embodiments, the recrystallization solvent is about 80-85% IPA/water. In some embodiments, the recrystallization solvent is about 80-87%

IPA/water. In some embodiments, the recrystallization solvent is about 83-87% IPA/water. In some embodiments, the recrystallization solvent is about 85% IPA/water. In some embodiments ratio is measured as (v:v). In some embodiments ratio is measured as (wgt:wgt),In some embodiments, the recrystallization solvent is a combination of methanol and water. In some embodiments, the recrystallization solvent is a combination of methanol and heptane.

When the recrystallization solvent is IPA/water, in some embodiments the method comprising dissolving the C9 in IPA (for example, by heating the mixture to about 40-45° C.), and then adding water. After addition of water, the temperature of the mixture may be returned to about 40-45° C. In other embodiments, the method comprises dissolving the C9 in the IPA/water mixture.

In some embodiments, the mixture containing dissolved C9 is polish filtered. The polish filtering may be performed at about 40-45° C., or at a temperature necessary to maintain the C9 in solution.

Cooling the mixture to about 32° C. in some embodiments occurs over a number of hours, for example, about 2-10 hours, or about 4-8 hours, or about 6 hours. In some embodiments, the mixture is then held at about 32° C. for a number of hours in order to allow the C9 to crystallize, for example, about 2-24 hours, or about 4-8 hours, or about 6 hours.

In some embodiments, the mixture is then further cooled. In some embodiments, the temperature may be cooled to about −5° C. to about 5° C., or about 0° C. The cooling may occur in a single step, or in multiple steps (e.g. cool to about 24° C., then to about 16° C., then to about 0° C.). In some embodiments, the mixture is cooled over a time period of about 3-24 hours. In some embodiments, the mixture is held at about 0° C., for example for at least an hour, or for about one hour.

The recrystallization procedure resulted in improved purity of C9 product. In various embodiments, the product comprises at least about 95% a/a, or at least about 96% a/a, or at least about 97% a/a, or at least about 98% a/a, or at least about 99% a/a, or at least about 99.5% a/a, as measured by HPLC, of the C9, exclusive of any solvents, carriers or excipients.

The procedure may also result in high purity of the claimed polymorph. In various embodiments, at least about 95% by mole, or at least about 96% by mole, or at least about 97% by mole, or at least about 98% by mole, or at least about 99% by mole, or at least about 99.5% by mole, of the 2,3,5-trimethyl-6-nonylcyclohexa-2,5-diene-1,4-dione is the polymorph, exclusive of any solvents, carriers or excipients.

The procedure may also result in high potency of C9. Potency=(100%−total impurities by HPLC)×(100%−water content %−total residual solvent %−Residue on ignition %). Potency may be calculated as follows (% area purity by HPLC/100)*(100−% wt/wt water content (KF)−% wt/wt residual solvents−% wt/wt=residue on ignition (ROI)). In various embodiments, the potency of the 2,3,5-trimethyl-6-nonylcyclohexa-2,5-diene-1,4-dione is at least about 95%, at least about 96%, at least about 97%, at least about 98%, at least about 99%, or at least about 99.5%.

The procedure may also result in a narrower distribution of particle sizes. D10 represents the particle diameter corresponding to 10% cumulative (from 0 to 100%) undersize particle size distribution (i.e. the percentage of particles smaller than D10 is 10%). D90 represents the particle diameter corresponding to 90% cumulative (from 0 to 100%) undersize particle size distribution (i.e. the percentage of particles smaller than D90 is 90%. In some embodiments, the particles have a ratio of D90:D10 less than about 11:1. In some embodiments, the particles have a ratio of D90:D10 less than about 10:1. In some embodiments, the particles have a ratio of D90:D10 less than about 9:1. In some embodiments, the particles have a ratio of D90:D10 less than about 8:1. In some embodiments, the particles have a ratio of D90:D10 less than about 7:1. In some embodiments, the particles have a ratio of D90:D10 less than about 6:1. In some embodiments, the particles have a ratio of D90:D10 less than about 5:1. In some embodiments, the particles have a ratio of D90:D10 less than about 4:1.

EXAMPLES

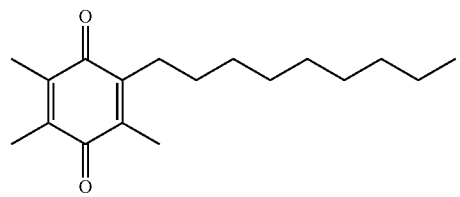 [SMILES: CCCCCCCCCC1=C(C)C(=O)C(C)=C(C)C1=O]

Example 1A. Synthesis of 2,3,5-trimethyl-6-nonyl-cyclohexa-2,5-diene-1,4-dione (3)

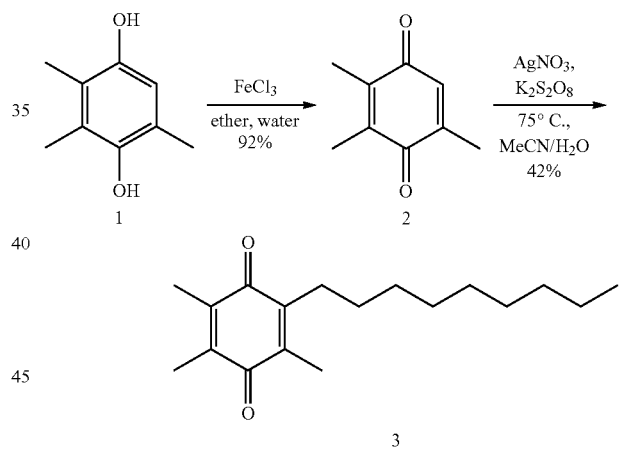

Into a 50 L reactor with a thermometer and a stirrer was added 2,3,5-trimethyl-benzene-1,4-diol (1) (1.39 kg, 9.1 mol) and ether (15 L) at 23° C. It turned to a clear solution after stirring for 30 minutes. A solution of ferric chloride (5.6 kg, 34.5 mol) in water (20 L) was added dropwise over 3 h. The reaction mixture was stirred for another 2 hours at this temperature. The organic phase was separated. The drained aqueous layer was extracted with ether (3×5 L). The combined organic phases were dried over sodium sulfate, and concentrated. The residue was diluted with dichloromethane (DCM) (1 L) and purified with silica gel chromatography (one column) to give the desired product 2 (1.27 kg, 95%). TLC (petroleum ether (PE)/ethyl acetate (EA)=30/1). $R_f$(Compound 1)=0.2. $R_f$(Product 2)=0.6.

Into a 50 L reactor with a thermometer and a stirrer was added 2,3,5-trimethyl-[1,4]benzoquinone (2) (780 g, 5.2 mol, 1.0 eq), decanoic acid (895 g, 5.2 mol, 1.0 eq), and acetonitrile (15 L). It turned to a clear solution after stirring at room temperature for 30 minutes. Silver nitrate (882 g, 5.2 mol, 1.0 eq) was added in one portion. The reaction mixture was heated up to 75° C. A solution of potassium persulfate (1.54 kg, 5.7 mol, 1.1 eq) in water (30 L) was added dropwise over 2 hours. After the addition, the reaction was stirred for additional 3 hours at 75° C. The solution was cooled to room temperature. The aqueous layer drained into 15 L of water, which was extracted with ethyl acetate (3×5 L). The combined organic phases were dried over sodium sulfate, filtered. The filtrate was concentrated to give a yellow residue, which was crystallized with hot methanol (800 mL). The solid was filtered and washed with small amount of methanol and ether, and dried in vacuo to afford 2,3,5-trimethyl-6-nonylcyclohexa-2,5-diene-1,4-dione (3) (447 g) as a yellow crystal agglomerate. The filtrate was concentrated and purified by flash column chromatography (petroleum ether:ethyl acetate, 100:1) to afford additional 155 g of 2,3,5-trimethyl-6-nonylcyclohexa-2,5-diene-1,4-dione (3) (total amount: 602 g, 42%). TLC (Petroleum ether/ethyl acetate (PE/EA)=30/1). $R_f$(Compound 2)=0.5. $R_f$(Product 3)=0.6. $^1$H NMR (400 MHz, CDCl$_3$) δ 2.46 (s, 2H), 2.02-2.01(m, 9H), 1.35-1.26 (m, 22H), 0.88-0.86 (m, 5H). Ag=45 ppm. Melting point 49.9.

The product had high silver content, and due to the combination of two isolations, one from trituration from MeOH and the other from column chromatography, the product was an inhomogeneous mixture comprising fine particles as well as large chunks of compound.

Example 1B. Recrystallization of 2,3,5-trimethyl-6-nonylcyclohexa-2,5-diene-1,4-dione (C9)

Summary. The product was prepared, after NaCl pretreatment, by recrystallization from 2-propanol (IPA)/water (H$_2$O) followed by digestion, collection, and drying via air and vacuum. The starting material (C9 as prepared in Example 1A, 99.9 g) had high Ag content (45 ppm) so a brine wash and two water washes were performed on a methyl tert-butyl ether (MTBE) solution of the C9 compound prior to drying and recrystallization. The MTBE solution of C9 was filtered through a 2.7 μm filter to remove any particulates present after the sodium chloride (NaCl) wash. During the solvent exchange from MTBE to the recrystallization solvent IPA, a brown solid formed in solution necessitating a hot filtration to remove. The tan solid likely resulted from light exposure of the quinone solution, and was not analyzed further. The filtered bright yellow solution was then protected from light, concentrated and dissolved into 85% IPA/H$_2$O (486 g/98 g) at 40° C. Heat was removed and crystals formed at 35° C. The slurry was allowed to stir for 48 h at 16° C., cooled to 0° C. and the solids collected, washed and dried to a constant weight under air and vacuum (~125 mmHg) to give 82.1 g (82.1%) of fine yellow needles. The material was analyzed by NMR, UPLC, LCMS, IR and MP.

Ag removal by NaCl wash. Crude C9 (99.9 g, as prepared in Example 1A) as a yellow conglomerate of mixed powder and crystals was dissolved in 500 mL methyl tert-butyl ether (MTBE) and the cloudy yellow liquid with small (1-2 mm) black flecks was washed with brine (100 mL, 20 wt % NaCl in H$_2$O). The turbid yellow organic upper layer was retained, the rag layer and clear, colorless aqueous phases were discarded. The organic phase was washed with water (2×100 mL) and dried over anhydrous sodium sulfate (Na$_2$SO$_4$, 35 g). The clear yellow solution was filtered through a 55 mm Whatman Type 3 filter (6 μm) stacked on top of a 55 mm Whatman GF/D filter (2.7 μm) and the vessels rinsed with MTBE (2×20 mL). IPA (100 mL) was added and concentrated via rotovap (125-90 mmHg, 40-25° C. bath) to give a bright yellow slurry (180 g). IPA (348 g) was added and the slurry heated to clarity (35° C., 120 mmHg) for 20 min, then pressure reduced to 60 mmHg and volume reduced until crystals started to form (~45 min). There was no odor of MTBE in the resulting slurry. The slurry was concentrated at 35° C. to a weight of 182 g, IPA (404 g) was added, heated to 40° C. until dissolved and concentrated to a yellow solid (35 mmHg). IPA (500 mL) was added and let stir overnight.

Filtration to remove Tan solids. Brown flecks were noted in the IPA solution and were removed by hot filtration (~40° C.) through a stacked 55 mm Whatman type 3 (8 μm) and Whatman GF/D (2.7 μm) filter. A sticky tan residue was left on the filter and the clear bright yellow solution was concentrated to a yellow solid via rotovap.

Recrystallization. To the yellow solid was added IPA (486 g), the vessel heated to 40° C. and water (98 g) added to the clear yellow solution. Heat was lowered to 21° C. over 2 h to give a bright yellow slurry of needles. The slurry was stirred for 48 h at 16° C., cooled to 0° C. and the thick yellow slurry filtered (Whatman #54, 150 mm Buchner). The fine yellow needles were rinsed with ice cold 85% IPA/H$_2$O (2×250 mL, 0° C.) and IPA (100 mL, 0° C.). The solids were left under suction for 1 h, a nitrile dam was installed on the Buchner funnel and held under house vac (~100 mmHg) overnight. The yellow crystals (88.9 g) still had an odor of IPA, so were removed to a new Buchner/filter (funnel had become plugged with C9 residue) and held under vacuum (100 mmHg, 6 h) to a constant weight (82.1 g, 82.1%). Transferred to a 500 mL Amber Type I Schott-Duran bottle at RT for storage. ~280 mL volume of crystals (82.1 g).

CoA analysis by qualified methods: Water content (KF)= 0.05%; Solvent Content=0.23%; HPLC Purity=100% AUC; Melting Point by DSC=53.0° C.; Ag content <2.00 ppm; Residue On Ignition=0.02%; Potency (calculated)=99.71%, Crystal form concordant with Pattern A.

Potency is calculated as follows (% area purity by HPLC/ 100)*(100−% wt/wt water content (KF)−% wt/wt residual solvents−% wt/wt=residue on ignition (ROI)).

Example 2. Recrystallization Screening

As shown in Examples 1A and 3A, synthetic methods for making C9 resulted in product that had one or more undesired characteristics, such as high silver content, stickiness of product, and undesired particle sizes and distribution. As discussed above, recrystallization may improve the properties of the product. Accordingly, a variety of solvents were screened for suitability in recrystallizing C9.

100 mg of C9 was placed in test tubes and solvent added and any change noted. Samples were then heated briefly with a heat gun (heating to approximately 45-50° C.), the solubility noted, allowed to cool to RT and solubility noted, then cooled to 0° C. and the solubility noted. The results are in the table below.

TABLE 1

Solvent Screening for Recrystallization

| Solvent | Approx conc. (mg/mL) | RT result | Hot Result | Hot to RT result | RT to Cold result |
|---|---|---|---|---|---|
| MeOH | 100 | slightly soluble | soluble | slightly soluble | insoluble - long needles |
| EtOH | 100 | partially soluble | soluble | slightly soluble | partially soluble - small needles |
| IPA | 100 | soluble | soluble | soluble | partially soluble- small needles |
| 70% IPA/H$_2$O | 100 | slightly soluble | mostly soluble - melted | slightly soluble (got cloudy and solids melted before solubility) | slightly soluble- translucent needles |
| MeCN | 100 | soluble | soluble | soluble | mostly soluble - small needles |
| THF | 100 | soluble | soluble | soluble | soluble |
| 95% EtOH | 100 | partially soluble | soluble | partially soluble | mostly insoluble |
| water | 10 | insoluble | insoluble | insoluble | insoluble |
| 80% EtOH | 100 | partially soluble | melted before complete dissolution | partially soluble | slightly soluble |
| 80% EtOH | 50 | partially | melted before dissolution | partially | slightly |

The following solvents were discarded as unsuitable, because the C9 was too soluble at cold temperatures: MeCN, THF.

The following solvents were discarded as unsuitable, because the C9 was not sufficiently solvent at higher temperatures: water.

The following solvents were discarded as unsuitable, because the C9 material melted before dissolution: 80% EtOH. This is disfavored since it will form an oil suspended in the solution. Upon cooling, it may crystallize, but the crystals will generally not be homogeneous or increase in purity.

95% EtOH was discarded as unsuitable because it contains MeOH and acetone, which can be problematic for pharmaceuticals.

Methanol and ethanol were less preferred, due to their low boiling points. In addition, the long needles from MeOH were less preferred because long needle crystals are harder to transfer and filter than more compact particles.

It was noted that ethanol produced almost completely soluble material when hot, and partially soluble when cold. IPA also exhibited similar behavior but was soluble at high temp at 100 mg/mL, and partially soluble at RT/cold. Ethanol/water mixtures were initially examined for solubility properties but was rejected as the C9 compound oiled out at >40° C. Since IPA had slightly better solubility without oiling out at higher temperatures before complete dissolution, and IPA was miscible with a good anti-solvent (H$_2$O), it was examined after ethanol proved unsuitable. 70% IPA/H$_2$O resulted in melting issues and oiling out, whereas 100% IPA was not ideally insoluble at cold temperatures. Accordingly, concentrations of IPA between 70-100% were tested.

Test solutions on 1 g scale determined that 75-85% IPA/water gave good solubility (~10:1 vol:wt), fine crystals that were filterable and solutions that could be heated and cooled to produce a predictable melt/crystallization. Seeding did not appear to be necessary. A hot filtration was required as a brown, material formed during crystallization when the solution was left exposed to room light for >1 h. This was only observed with the solution was exposed to light. Recovery was 92.7% of fine needles and UHPLC analysis of the supernatant was 91% a/a vs 99% for the solid indicating the supernatant was removing impurities. Fine yellow needles resulted which were easily filtered and washed with good recovery. UHPLC showed an improvement in UHPLC area % and the crystals were all similar in size and flowed easily once dry.

Example 3A. Synthesis of 2,3,5-trimethyl-6-nonyl-cyclohexa-2,5-diene-1,4-dione

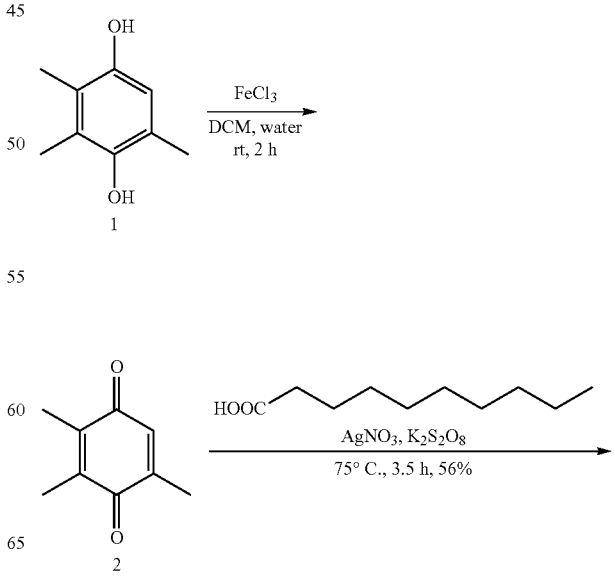

-continued

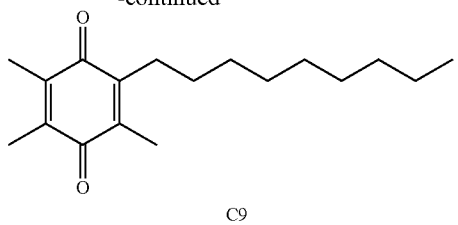

C9

The stirred solution of compound 1 (2.0 kg, 13.15 mol, 1.0 eq) in dichloromethane (20 L) was stirred at 23° C. for 30 min. A solution of ferric chloride (5.33 kg, 32.88 mol, 2.5 eq) in water (19.04 L) was added dropwise over 22 h. The reaction mixture was stirred for another 2 hours at this temperature. HPLC showed compound 1 was completely consumed. The organic phase was separated. The drained aqueous layer was extracted with dichloromethane (2×10 L). The combined organic phases were washed with water (2×20 L), brine (2×10 L) and dried over sodium sulfate (about 5 kg), and concentrated to give crude compound 2 (1.95 kg, crude), which used directly in the next step without further purification.

A mixture of compound 2 (1.25 kg, 8.33 mol, 1.0 eq) and decanoic acid (1.44 kg, 8.33 mol, 1.0 eq) in acetonitrile (25 L) was stirred at room temperature for 30 minutes. Silver nitrate (353.9 g, 2.08 mol, 0.25 eq) was added in one portion. The reaction mixture was heated up to 75° C. A solution of potassium persulfate (2.48 kg, 9.17 mol, 1.1 eq) in water (100 L) was added dropwise. After the addition, the reaction was stirred for additional 3.5 hours at 75° C. HPLC showed compound 2 was completely consumed. The solution was cooled to room temperature. The aqueous layer was drained into 50 L of water, which was extracted with ethyl acetate (3×10 L). The combined organic phase was washed with aqueous sodium chloride (5 L), dried over sodium sulfate (about 5 kg), and filtered. The filtrate was concentrated. The residue was purified by column chromatography on a silica gel (PE, PE/EA, 50/1) to give a crude product. The product was obtained as oil after flash column chromatography (FCC) (solidified after standing). It was charged into three-necked flask quickly before solidifying. The oil was stirred and a solid was formed with stirring. The solid was triturated with methanol (2 volumes, added dropwise, as the amount of crude product after column purification) overnight (~15 hours) at room temperature (20~30° C.), and filtered. The cake obtained was washed with methanol (500 mL) and dried in vacuo: solid was charged into a 20 L rotary evaporator with a vacuum pump (0.5 mmHg) in a water-bath (<30° C.), for 7 days, 8 hours/day, for removing the residual solvents: acetonitrile, methanol, dichloromethane and ethyl acetate) to afford C9 (1.28 kg, 56%) as a yellow crystal. The product was spread in a stainless container, and crashed with a mortar in order to obtain similar size. The milling process was repeated several times. Attempt to sieve the solid was tried. However, the solid could not be sieved as the product stuck on the sieve (100 mesh). Because the milling of this material is difficult, the particles derived are large and will be difficult to formulate.

TLC (PE/EA=30/1). $R_f$(Compound 2)=0.5. $R_f$(C9)=0.8. LC-MS: n/a.

$^1$H NMR (400 MHz, CDCl$_3$) δ 2.45-2.42 (t, J=7.4 Hz, 2H), 1.99-1.94 (m, 9H), 1.24 (m, 16H).

Assay=HPLC 92.2% w/w versus reference standard.

Example 3B. Recrystallization of 2,3,5-trimethyl-6-nonylcyclohexa-2,5-diene-1,4-dione Summary. This example summarizes the recrystallization of C9 on a 10 g engineering batch and the subsequent recrystallization of 2.4 kg of C9 (both samples as provided from Example 3A). Dissolution of the material in 2-propanol at 40° C., followed by the addition of water to achieve a hazy solution which was polish filtered through a jacketed filter at 40° C. The resulting clear solution was slowly cooled to 32° C., upon which the product spontaneously crystallized as fine yellow needles. Further stepwise cooling to 16° C. and then 0° C. afforded a slurry which was collected by filtration and rinsed with 85% 2-propanol in water. The resulting solid was dried under vacuum at 25° C. to constant weight to afford the product (1.975 kg) with a recovery of 82%. The isolated solid was tested and passed by DSC, IR, and $^1$H NMR.

Discussion.

Advantages of the processing described here are: allows for controlled formation of a truly crystalline solid, with no oiling; no need for seed crystals; an increase in assay/purity; lack of stickiness with good flow properties; a tighter particle size distribution; and regular-shaped particles that are easier to isolate and dry. If necessary, milling of this material is expected to be straightforward.

LCMS analysis of the supplied C9 (made according to Example 3A, 92.2% pure) showed a major impurity by total ion count (TIC) that was not visible at UV254 or by evaporative light scattering detector (ELSD). The impurity was efficiently purged in the recrystallized product with high recovery of the impurity in the mother liquor.

The cooling protocol enacted produced crystals without oiling out or requiring the use of seed crystals, crystallization occurred at 32° C.

The final product isolation afforded a wet cake that was transferred to a drying oven at 25° C. without the use of a nitrile dam.

Recrystallization (2.4 kg).

To a 50 L jacketed reactor equipped with an overhead mechanical stirrer, argon inlet, and a Teflon-coated temperature probe was added C9 (2400 g) and 2-propanol (15.6 L, Fisher A416). The mixture was stirred at 75 rpm under argon and the reactor was covered with aluminum foil. The reactor jacket was warmed to 41° C. (internal temperature 40° C.) and stirred for 60 minutes to become a clear solution.

To the reaction was added deionized water (2.5 L, Ricca 9150-5) and the solution was stirred for 90 minutes. The solution was polish filtered through a P4 (10-16 um) sintered glass jacketed funnel at 40° C. using positive argon pressure (8 psi) and collected in a 20 L glass carboy.

The 50 L reactor was rinsed with 2-propanol (2 L, Fisher A416) and drained to organic waste.

The clear supernatant (36° C.) was returned to the 50 L jacketed reactor equipped with an overhead mechanical stirrer, argon inlet, and a Teflon-coated temperature probe, and heated back to 40° C. The solution was stirred at 75 rpm and cooled to 32° C. over 6 hours and then held at 32° C. for an additional 6 hours. Crystals had formed. The slurry was cooled to 24° C. for 1 hour and further cooled to 16° C. for 1 hour and cooled to 0° C. for 1 hour.

The solid was collected on a P4 (10-16 um) sintered glass funnel using positive argon pressure (8 psi). The filter cake was rinsed with 2-propanol/water (85/15 v/v, 2×6 L) and dried under an argon stream for 2 hours to afford 3450 g of a yellow solid. The solid was transferred to a vacuum oven and dried under vacuum at 25° C. for 240 hours. The weight was checked at ~24 hour intervals until constant weight was achieved to afford the final product C9 (1975 g, 82.2% yield) as a free-flowing yellow crystalline solid. DSC analysis of the solid showed an onset of melting at 48.66° C. and a melting point of 50.13° C. Assay by HPLC showed 99.4% a/a purity.

The mother liquor was concentrated under reduced pressure to afford 400 g of a red oil. Analysis of the oil showed some product, with a major impurity peak by TIC that did not appear to have appreciable absorbance at 254 nm. The molecular weight of the impurity appeared to be 373 (M+H=374 amu).

CoA analysis by qualified methods: Water content (KF) =0.06%; Solvent Content=0.24%; HPLC Purity=100% AUC; Melting Point by DSC=53.0° C.; Ag content <2.00 ppm; Residue On Ignition=<0.01%; Potency (calculated) =99.69%, Crystal form concordant with form A.

Example 4. Polymorph of 2,3,5-trimethyl-6-nonyl-cyclohexa-2,5-diene-1,4-dione Summary A summary of as-received Pattern A and its melt is given below.

Figure 6:
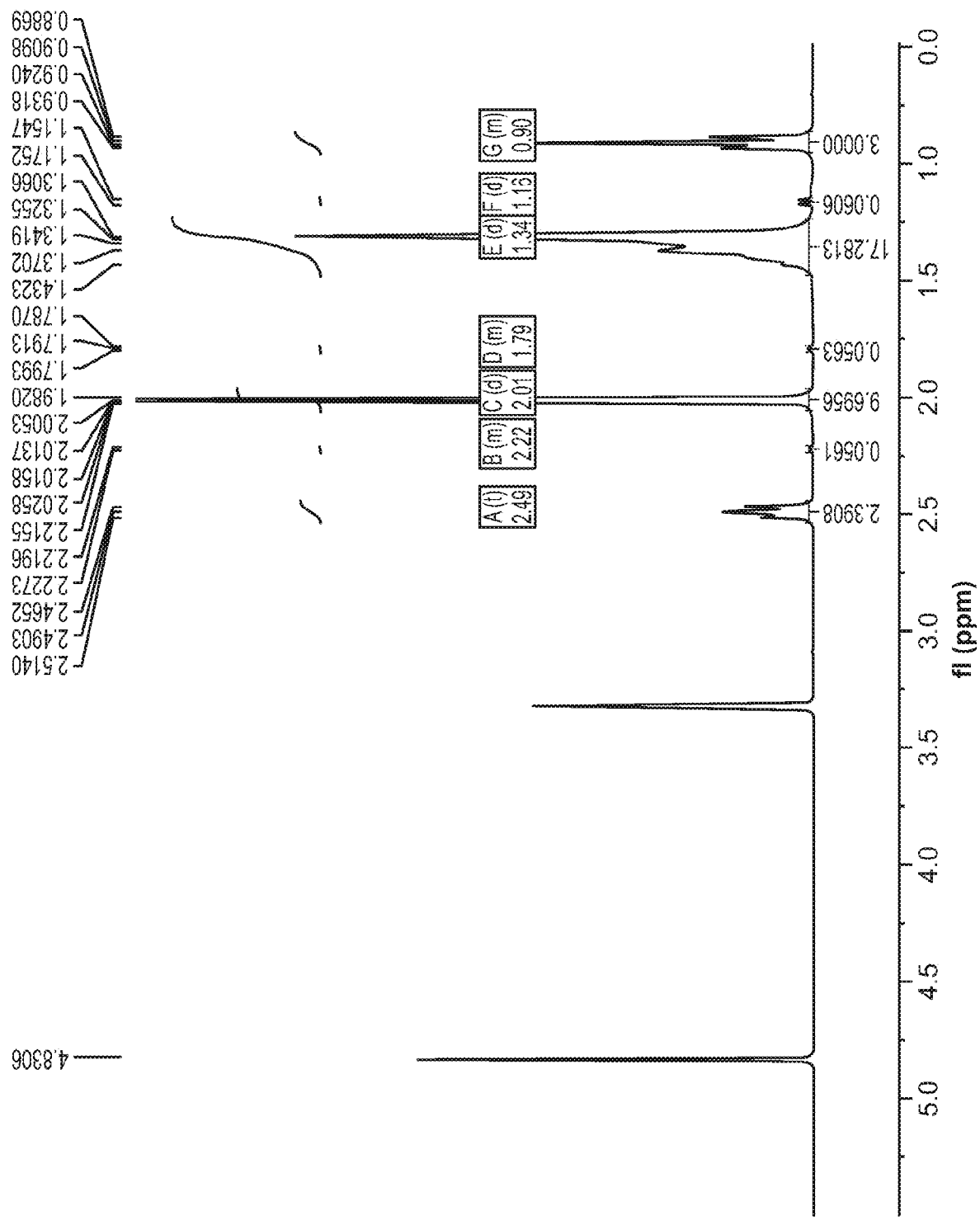
FIG. 6 shows the $^{1}$H NMR spectrum of as-received material (ID 1-1) in MeOD.

The material (ID 1-1) was dissolved in MeOD and analyzed by $^1$H NMR (FIG. 6). The NMR spectrum was consistent with the structure of 2,3,5-trimethyl-6-nonylcyclohexa-2,5-diene-1,4-dione. It is also consistent with it being anhydrous and not a solvate.

Figure 7:
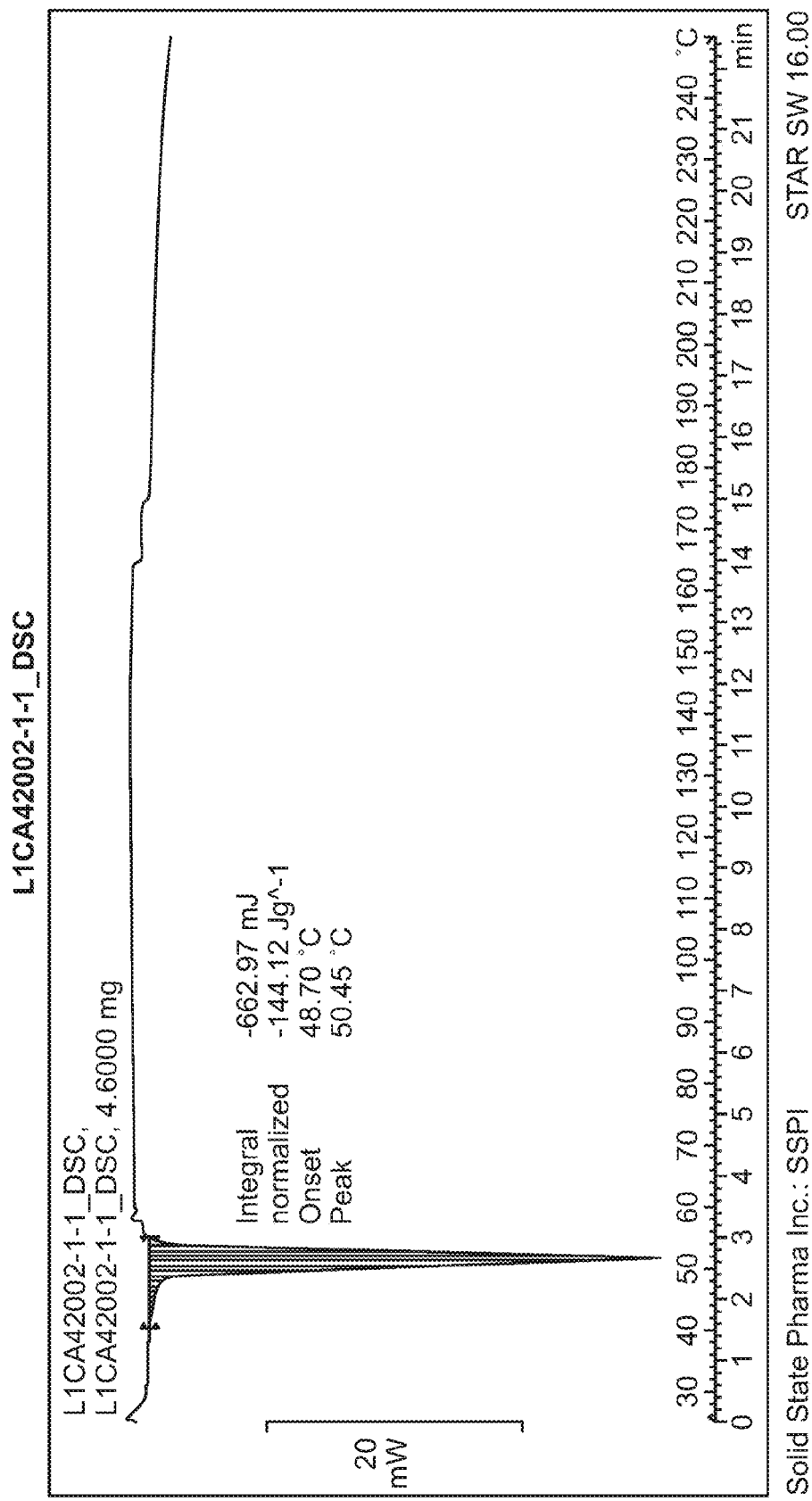
FIG. 7 shows the Standalone DSC thermogram of as-received material (ID-1-1).
Figure 8:
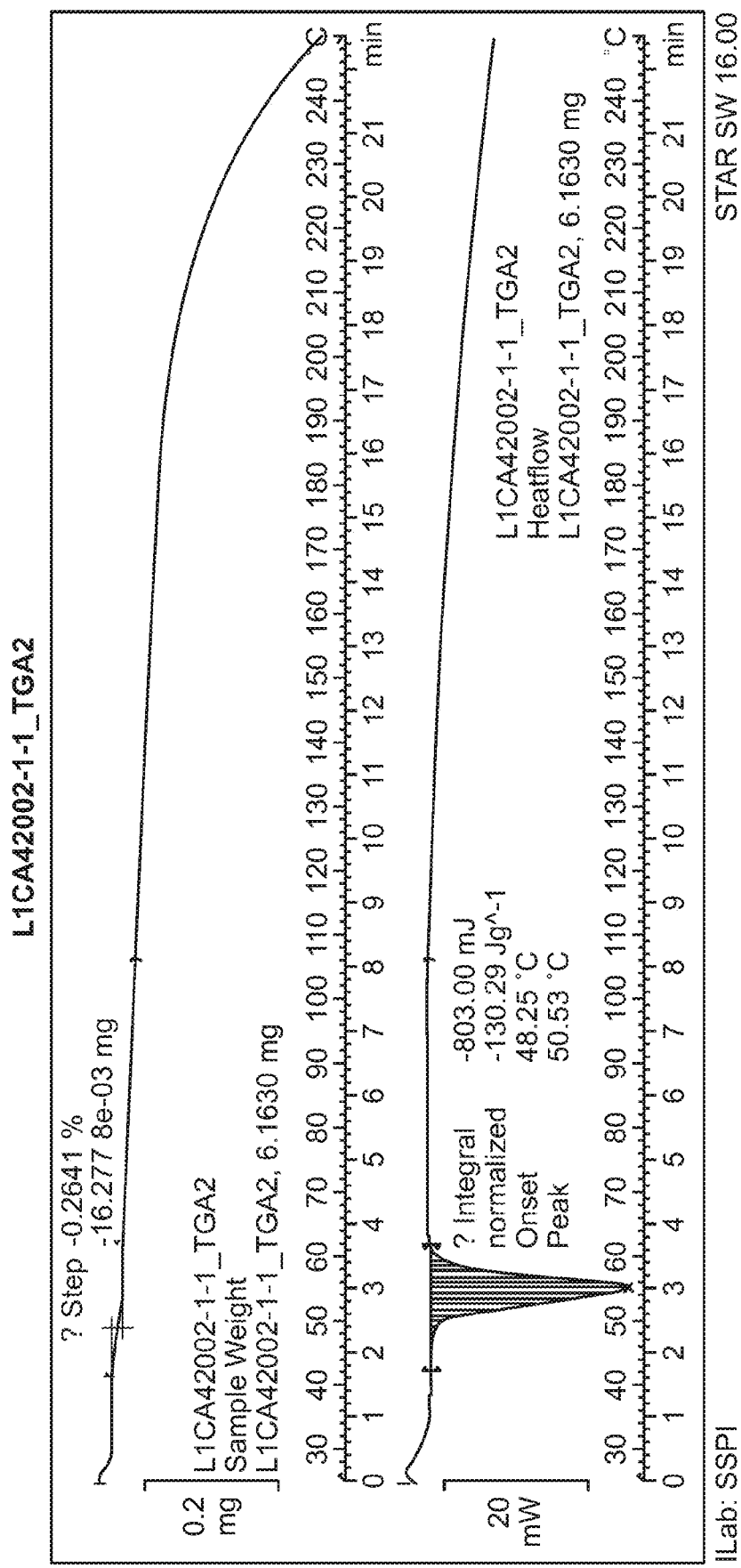
FIG. 8 shows TGA and DCS thermograms of as-received material (ID-1-1).

DSC of the material (ID 1-1) showed an onset of melting at 48.70° C. (FIG. 7). Simultaneous TGA/DSC showed an onset of melting agreeing with DSC, with an associated step for weight loss of 0.26% (FIG. 8). Summary of DSC data including method details is shown in Table 3.

TABLE 3

Peak list for DSC thermogram of material (ID 1-1)*.

| Onset (° C.) | Peak (° C.) | Normalized enthalpy (J/g) |
|---|---|---|
| 48.70 | 50.45 | −144.12 |

*The DSC thermogram was obtained with Mettler Toledo DSC3+ with a method that ramps from 25-250° C. at 10° C./min, 60 mL/min N2, in hermetic Al pan with lid with pinhole, uncrimped.

| | | | | | Solubility at 24 hours (mg/mL)* | | | |
|---|---|---|---|---|---|---|---|---|
| Solid | Crystallinity | DSC Onsets (° C.) | DVS Mass Change (wt. %) | FaSSGF | FeSSIF | FaSSIF | 0.5% MC + 2% Tween80 (aq) | Water |
| Pattern A | high | 48.70 | 0.01 (15-75% RH); 0.08 (2-95% RH) | BDL | 0.20 | BDL | 0.31 | BDL |
| Melted Pattern A | none | — | 0.044 (15-75% RH); 0.073 (2-95% RH) | BDL | 0.20 | 0.04 | 0.28 | BDL |

*BDL: Below detection limit.

Characterization

Figure 5:
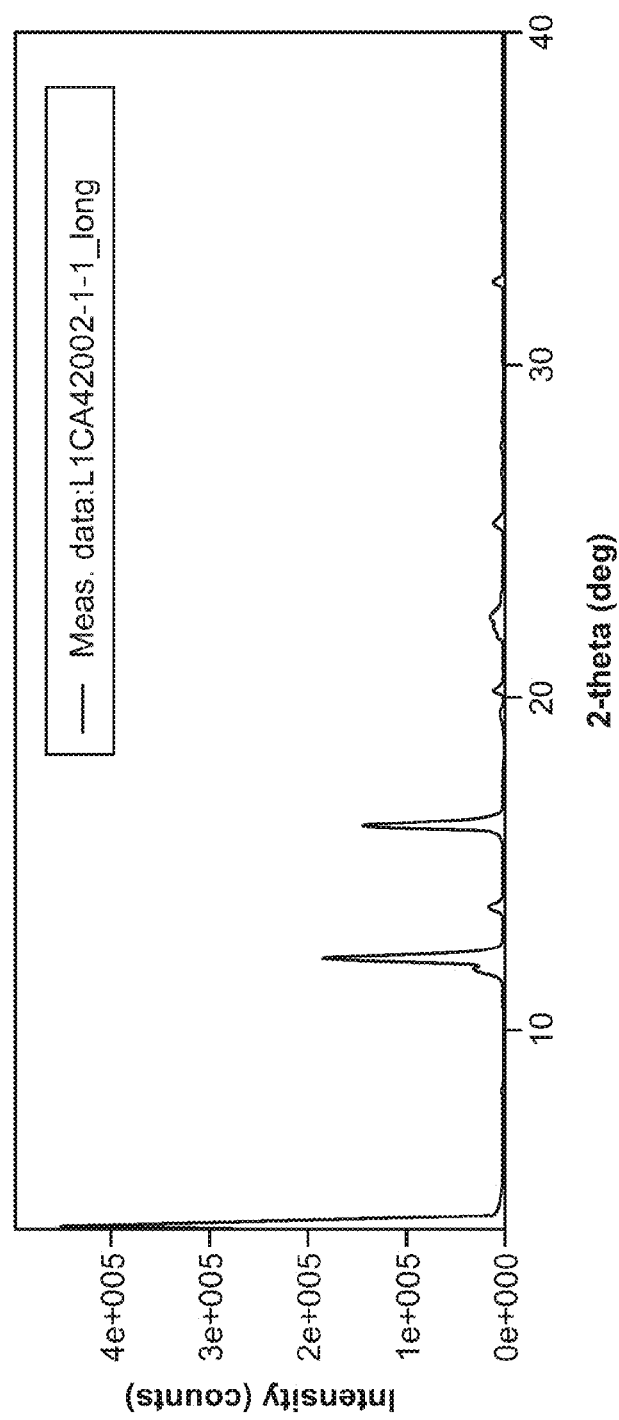
FIG. 5 shows XRPD diffractogram of as-received material (ID 1-1), Pattern A, analyzed by long scan method.

The as-received solid (ID 1-1, as produced according to Examples 1A and 1B) was a slightly tacky, yellow powder. The container was stored in a refrigerator at 5° C. As the material was sensitive to light, the container and all sample vials were protected from light exposure with amber or foil-covered vials. XRPD analysis of the material (ID 1-1) showed the material was crystalline and had high intensity peaks at 4, 12, and 16 °2θ, as well as several other lower intensity peaks; this pattern was designated as Pattern A (FIG. 5). A peak list with d-spacing and intensity is shown in Table 2.

TABLE 2

XRPD Peak list for material (ID 1-1). Peaks with relative intensity >5 are reported

| 2-theta (deg.) | D-spacing (Å) | Relative Intensity (counts) |
|---|---|---|
| 4.10 | 21.52 | 100 |
| 11.77 | 7.51 | 8 |
| 12.12 | 7.30 | 40 |
| 16.14 | 5.49 | 31 |
| 22.41 | 3.96 | 7 |

* diffraction pattern in Table 2 was obtained with a Rigaku MiniFlex 600 with Cu Kα1 source, a wavelength of 1.540598 Å, and a temperature of 23-25° C.

Figure 9A:
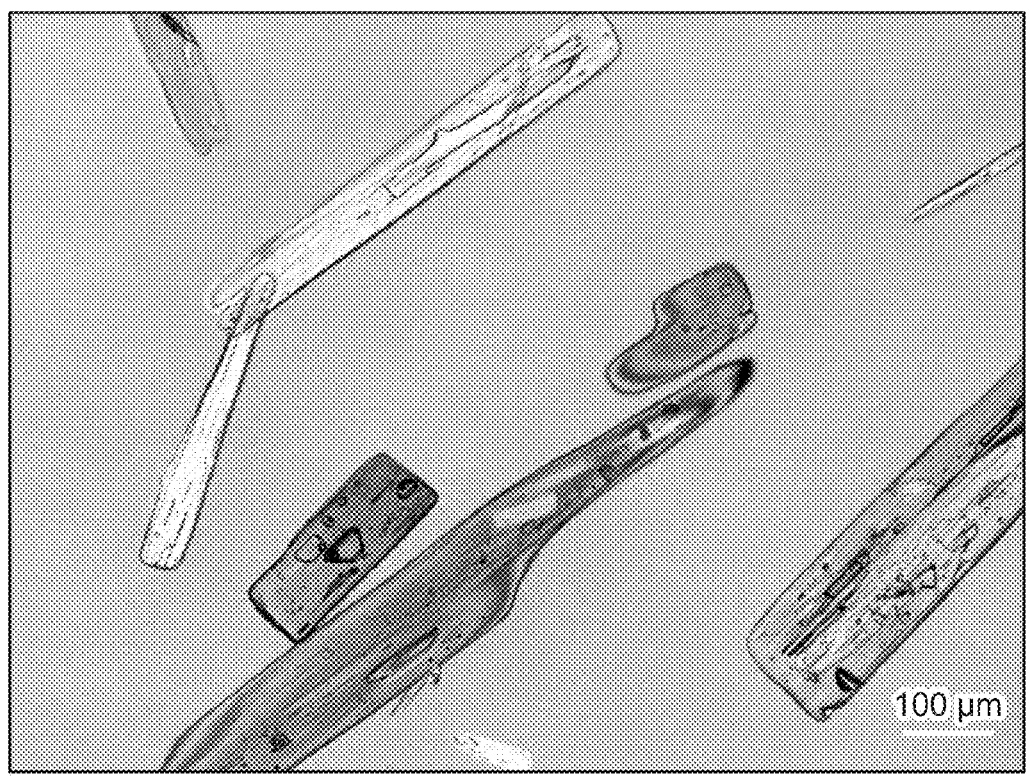
FIG. 9A (where 100 μm scale is indicated in the bottom right corner) and 9B (where 20 μm scale is indicated in the bottom right corner) shows microscopy images of as-received material (ID-1-1) at 100× and 400× magnification, respectively.
Figure 9B:
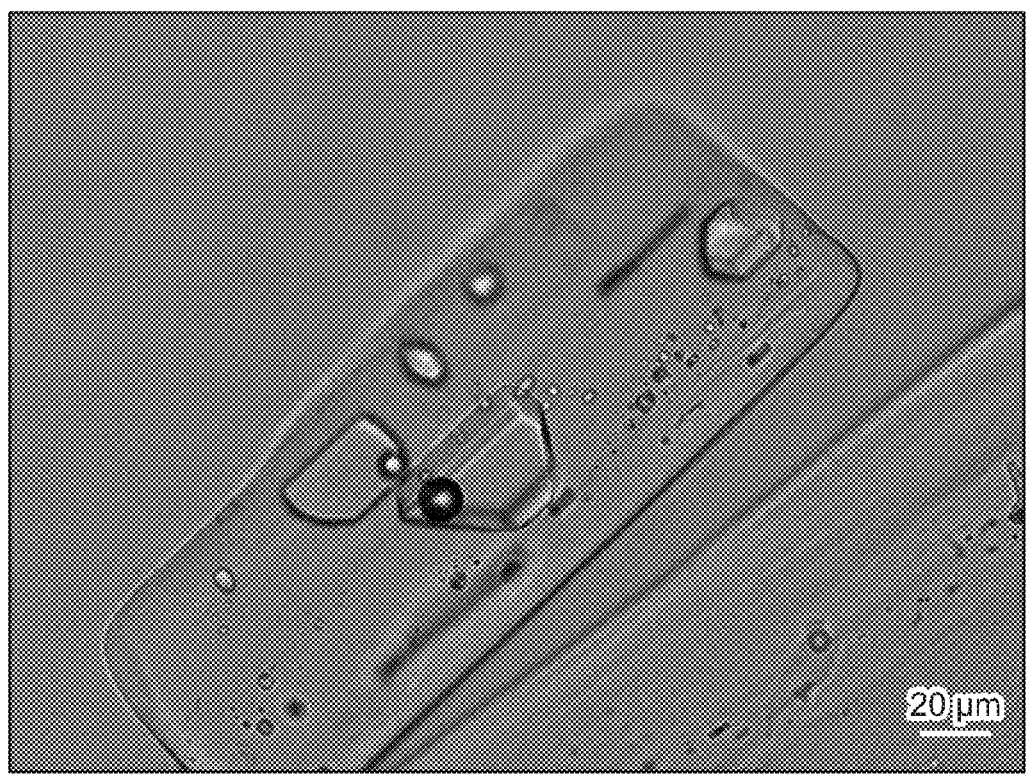

Microscopy images of the as-received material (ID 1-1) were captured at 100× (FIG. 9A) and 400× (FIG. 9B) magnification. The material showed rectangular, plate-like morphology.

Karl Fischer (KF) titration for water content was performed with two samples of as-received material (ID 1-1), the first with 24 mg and the second with 43 mg; however, neither sample provided a measurement by the titrator. This indicated that the water content of the material was below the limit of detection for the instrument (>1 ppm). This result is consistent with the material being anhydrous.ppm).

Figure 10:
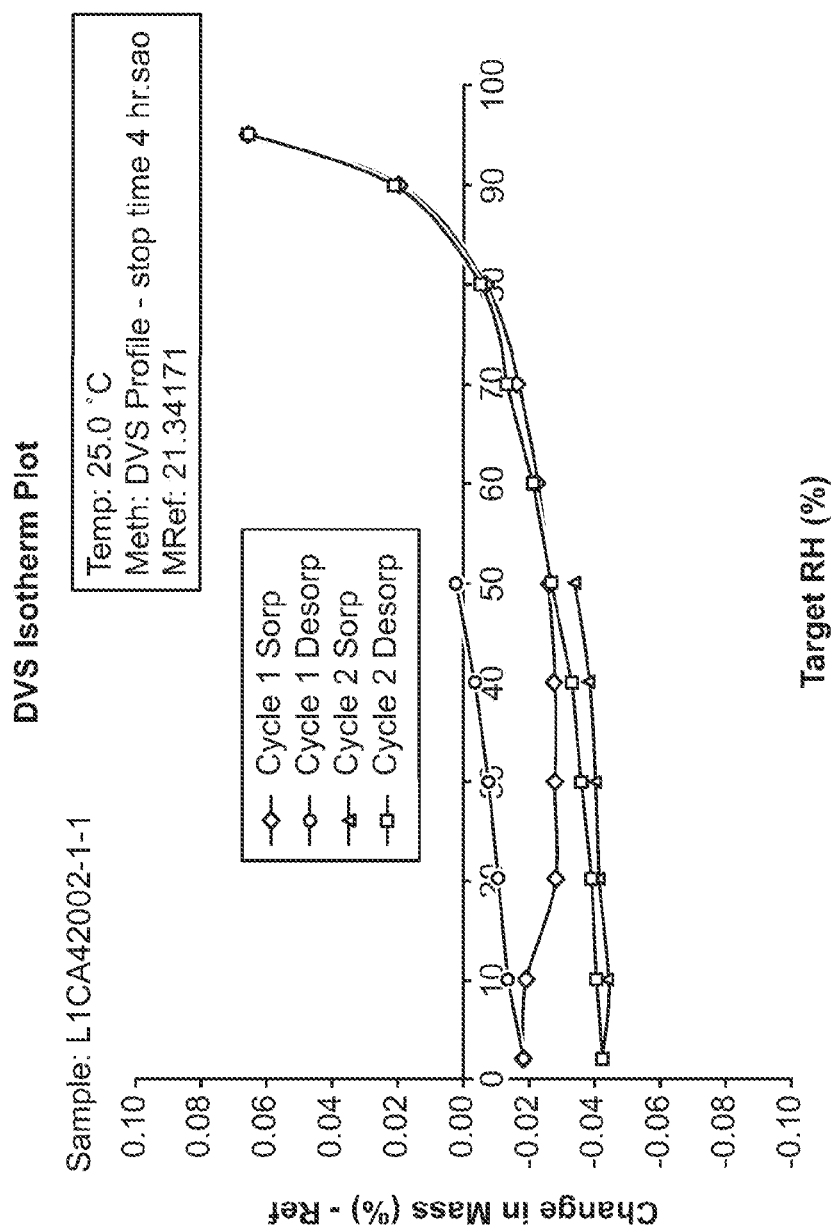
FIG. 10 shows a DVS isotherm plot for as-received material (ID-1-1).
Figure 11:
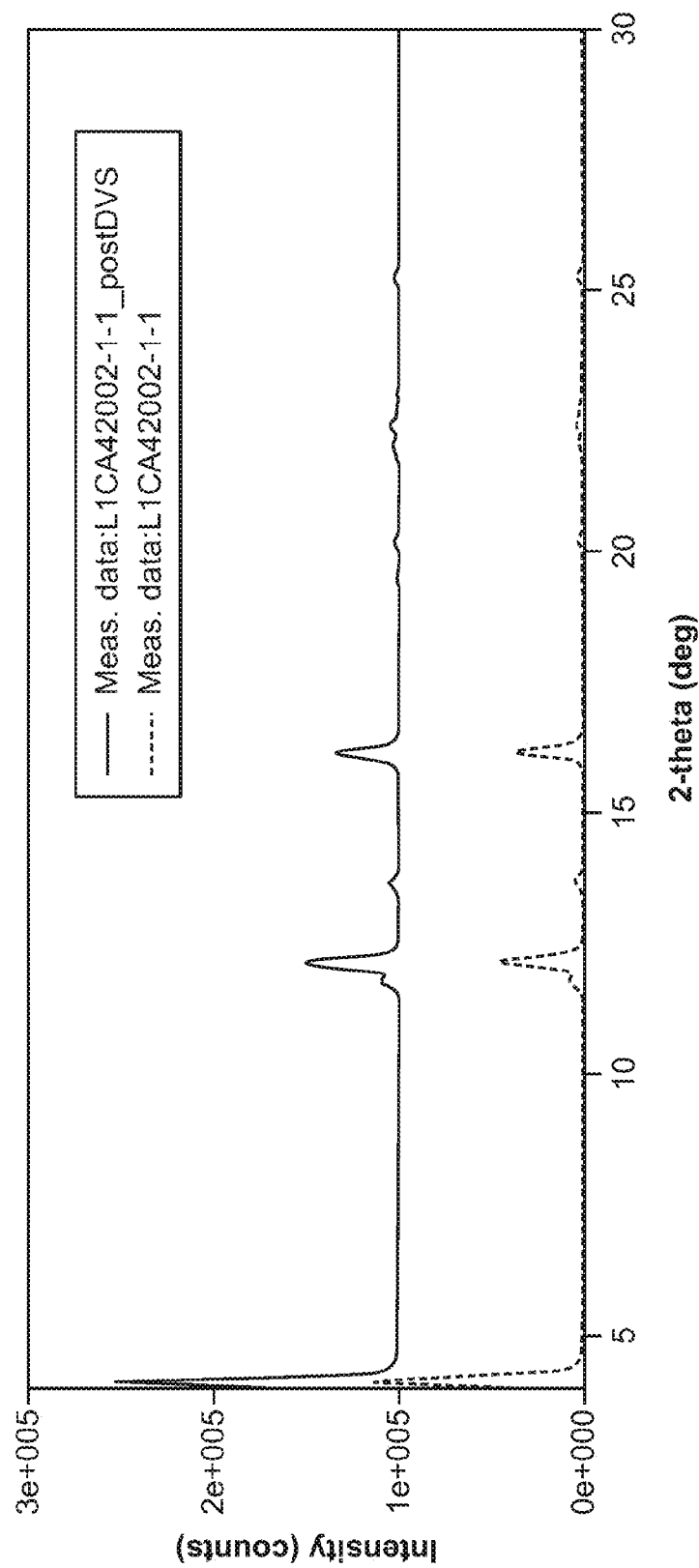
FIG. 11 shows XRPD diffractograms of the as-received solid (ID-1-1), Pattern A (bottom), compared to the solid after humidification cycling in the DVS instrument (top).

As-received material (ID 1-1) was subjected to humidification cycling by dynamic vapor sorption (DVS) instrument. The material underwent a 0.01% change in mass in the 15-75% relative humidity range, and a 0.08% change in mass over the full range of 2-95% relative humidity. The isotherm plot is shown in FIG. 10. Following humidification cycling, the solid was analyzed by XRPD. The observed pattern was unchanged from the as-received solid (ID 1-1), Pattern A; the XRPD data is shown in FIG. 11. These results demonstrate that the material is not hygroscopic.

Figure 12:
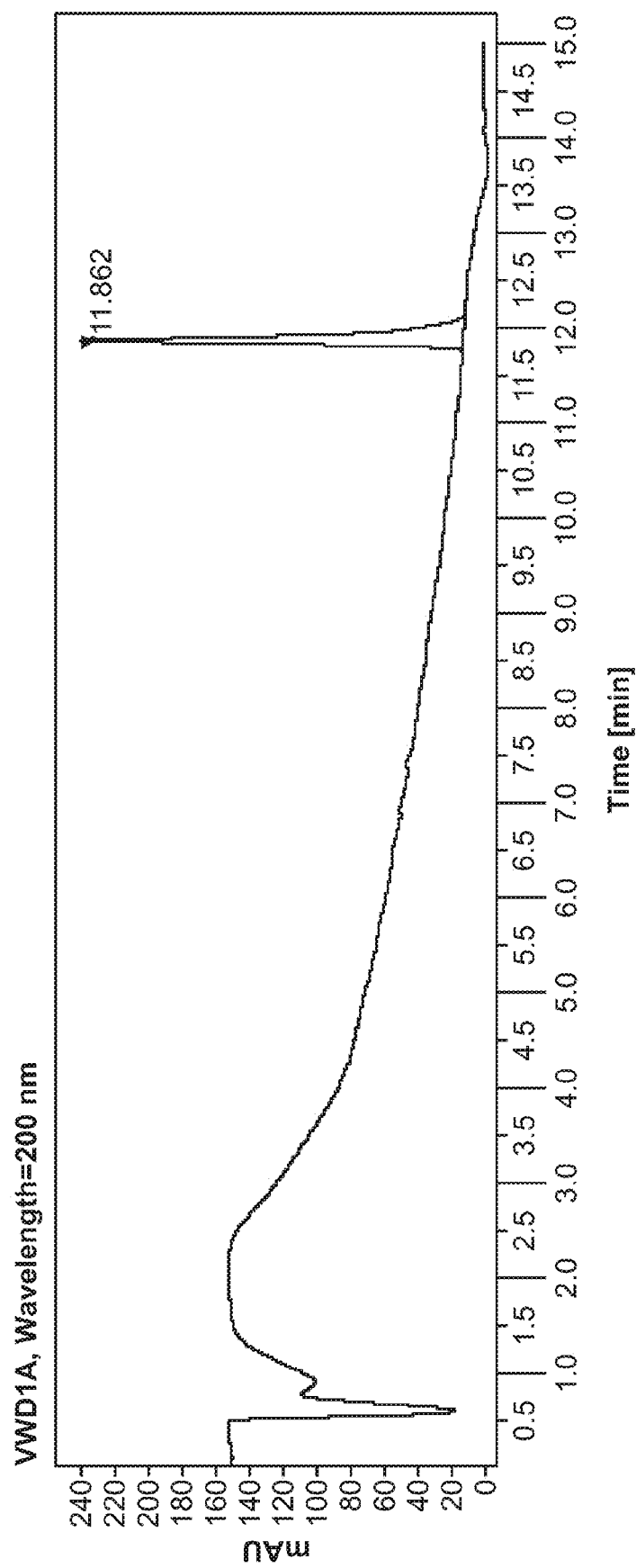
FIG. 12 shows HPLC chromatogram of as-received material (ID-1-1).

A sample of the as-received solid was dissolved to 0.5 mg/mL concentration and injected by HPLC for purity analysis. No impurities were observed. The chromatogram is shown in FIG. 12.

Figure 13:
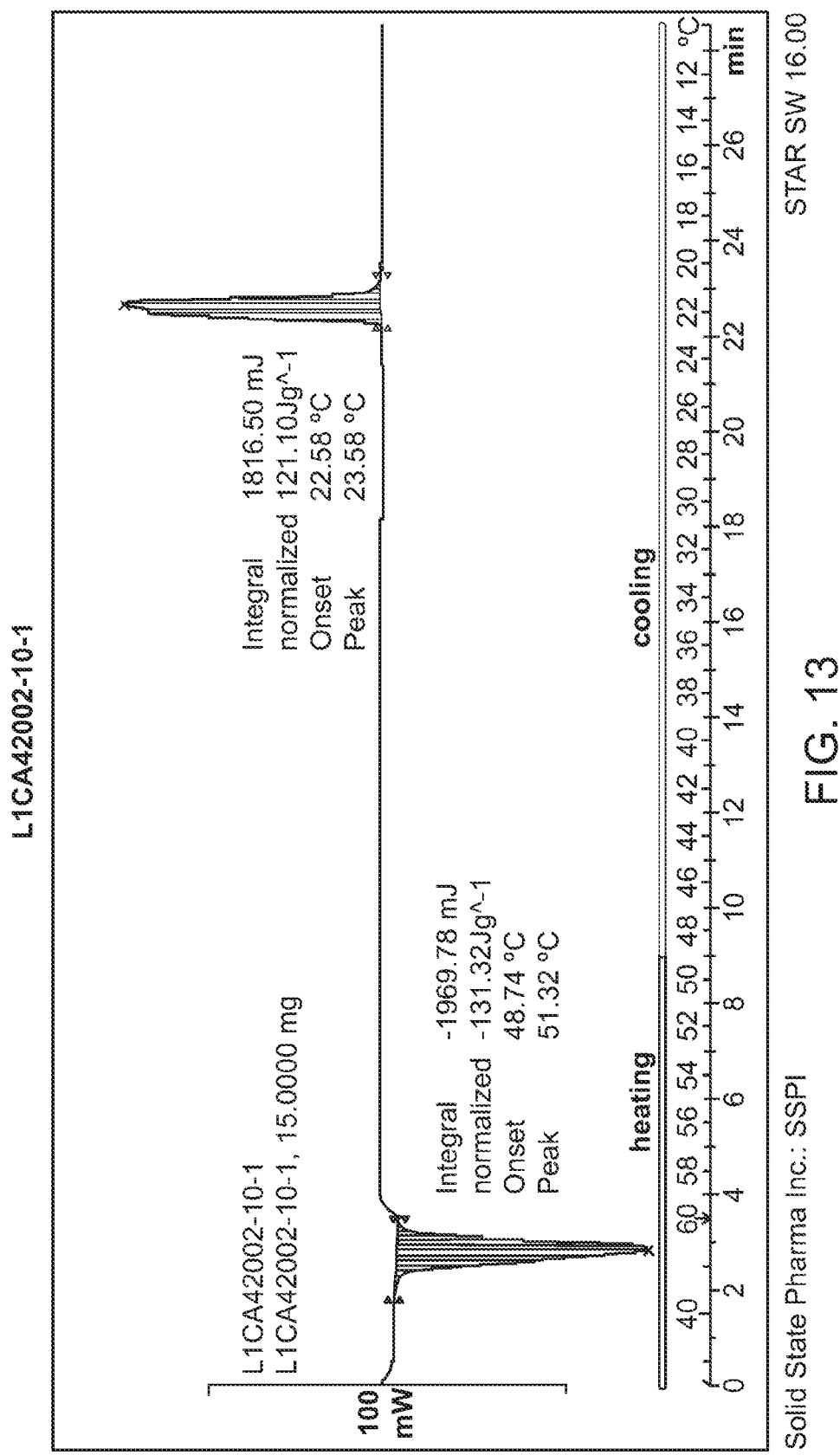
FIG. 13 shows DSC thermogram of ID-10-1 after thermal treatment of ID 1-1.
Figure 14:
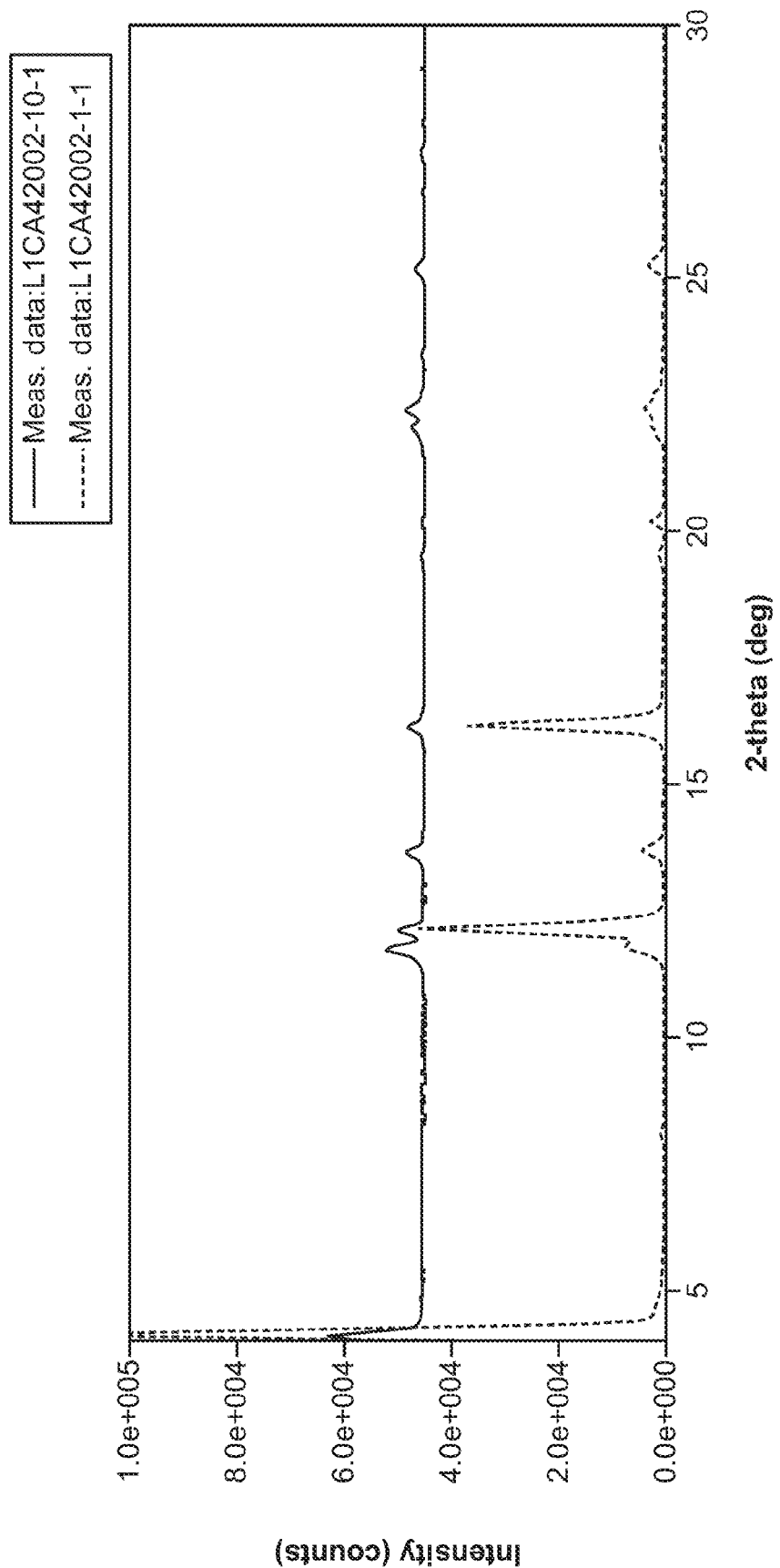
FIG. 14 shows XRPD diffractograms of as-received material (ID-1-1), Pattern A (bottom), compared with the solid recovered from thermal treatment (ID 10-1) (top).

Thermal Treatment 15 mg of as-received material (ID-1-1) was weighed into a DSC pan and subjected to thermal treatment on the standalone DSC instrument with a method that heated to 60° C. at 10° C./min and then cooled to 10° C. at 2° C./min. The resulting material was recovered from the pan and plated for XRPD analysis (ID-10-1). The material melted with onset of 48.74° C., and recrystallized with an exothermic onset of 22.58° C. The recovered material showed Pattern A by XRPD. The thermogram from the DSC treatment is shown in FIG. 13. The XRPD data is shown in FIG. 14.

Hot Stage Microscopy

A Linkam hot stage system was employed to capture images of the as-received solid (ID-1-1) during melting. A small amount of material was placed on a microscope slide inside the hot stage, and a temperature ramp method was employed to go from 30° C. to 55° C. at a rate of 1° C./min. A series of images was captured at 200× magnification during the ramp. No morphology changes were observed up until melting (data not shown). Following melting, the hot stage was cooled back to room temperature naturally and the material was monitored at 200× magnification for recrystallization, but no solids were observed; the sample appeared as a glass. The material was manipulated with a 21-gauge needle to attempt crystal nucleation. The slide was then removed from the hot stage and an image was captured at 200× magnification; the resulting material appeared unchanged (data not shown). This shows that the compound can exist as a melted liquid form (amorphous) at room temperature.

Solid Form Stability.

The solid form stability of the material was assessed over one week. 49.0 mg of ID-1-1 was placed inside of a foil-covered 4 mL vial, which was covered with a KimWipe. This vial was placed inside a 20 mL vial containing saturated aqueous sodium chloride. The vial was placed on a hot plate at 40° C. for 7 days, creating an atmosphere of 75% relative humidity in the system. After 7 days, the solid was sampled for HPLC (ID-4-1).

Figure 15:
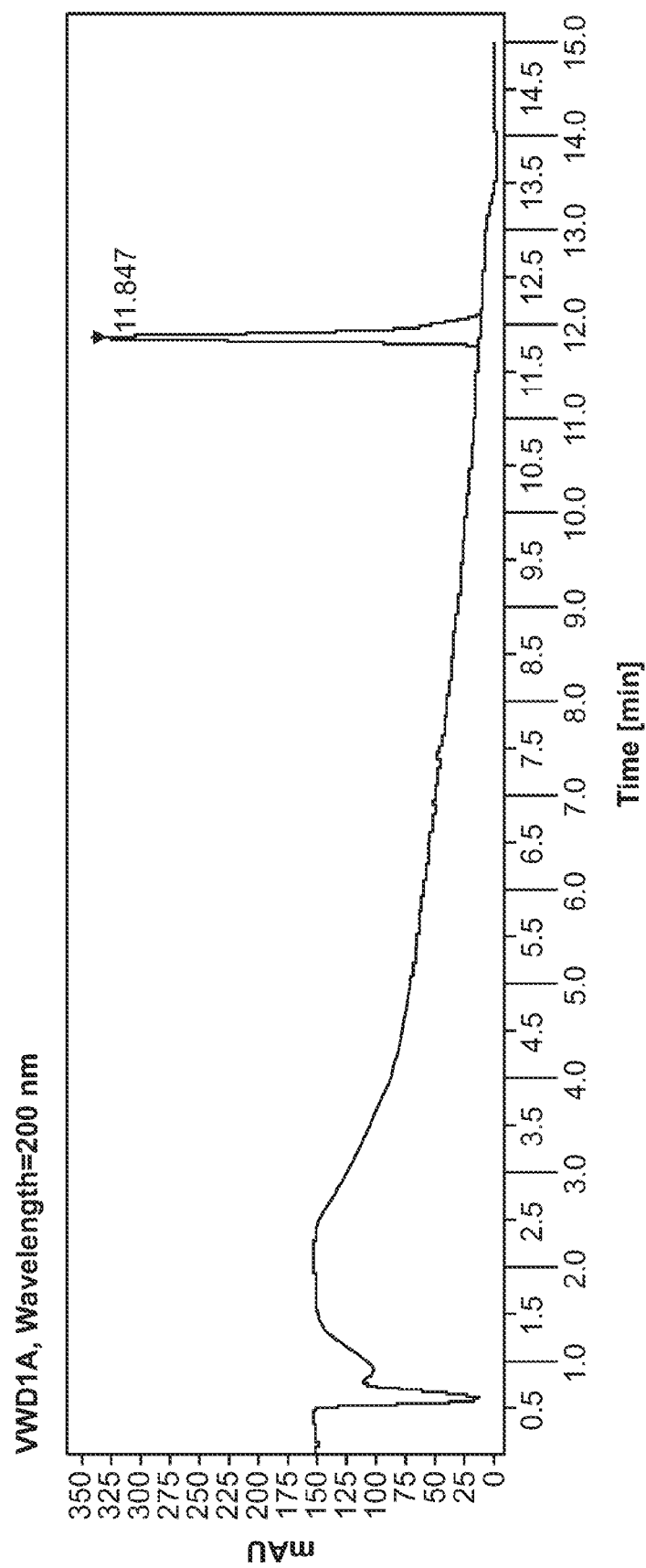
FIG. 15 shows HPLC chromatogram of stability sample ID-4-1.
Figure 16:
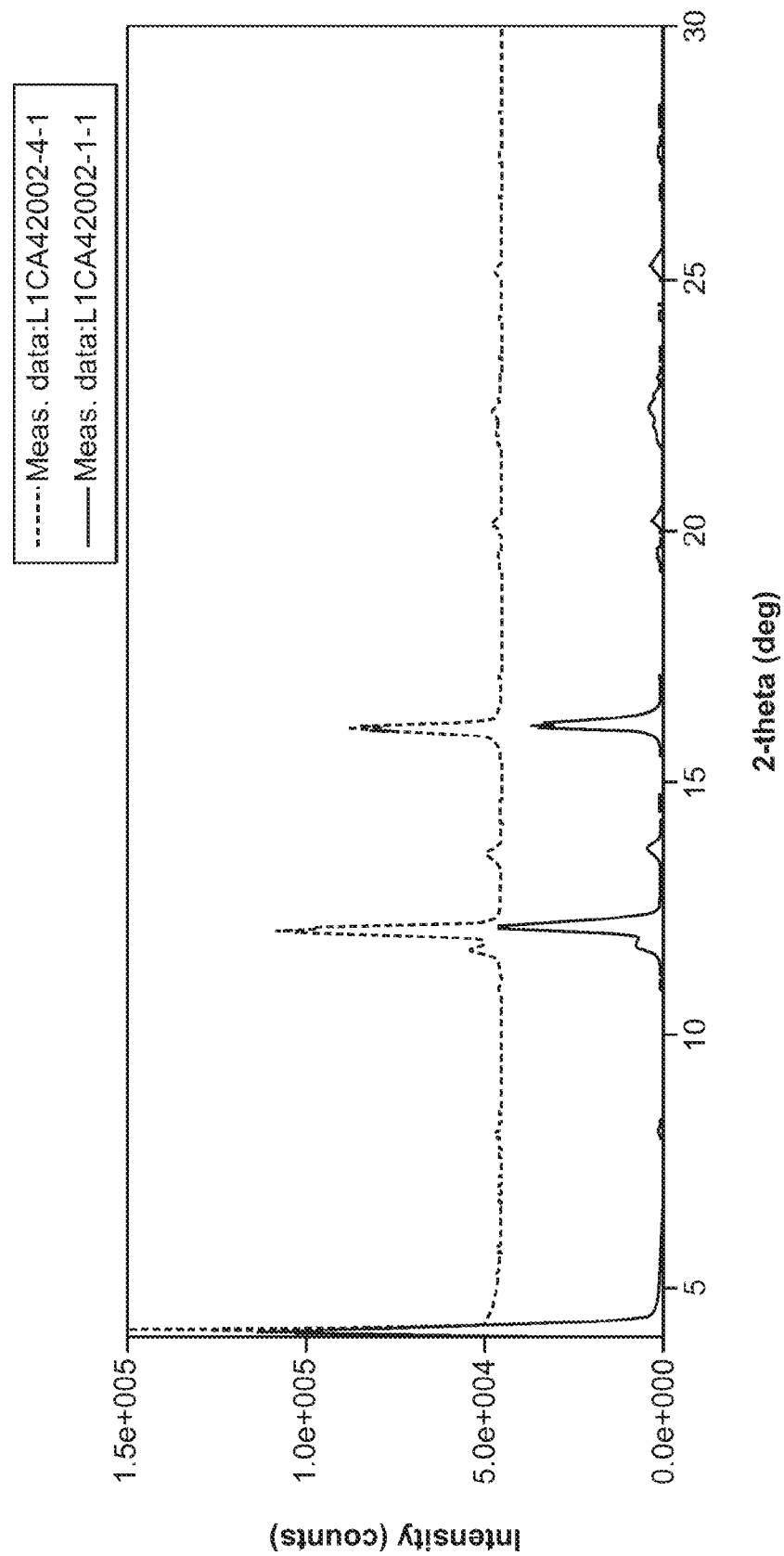
FIG. 16 shows XRPD diffractograms of as-received ID-1-1 (bottom) compared to solid form stability sample ID-4-1 (top) after one week at 75% RH and 40° C.
Figure 17A:
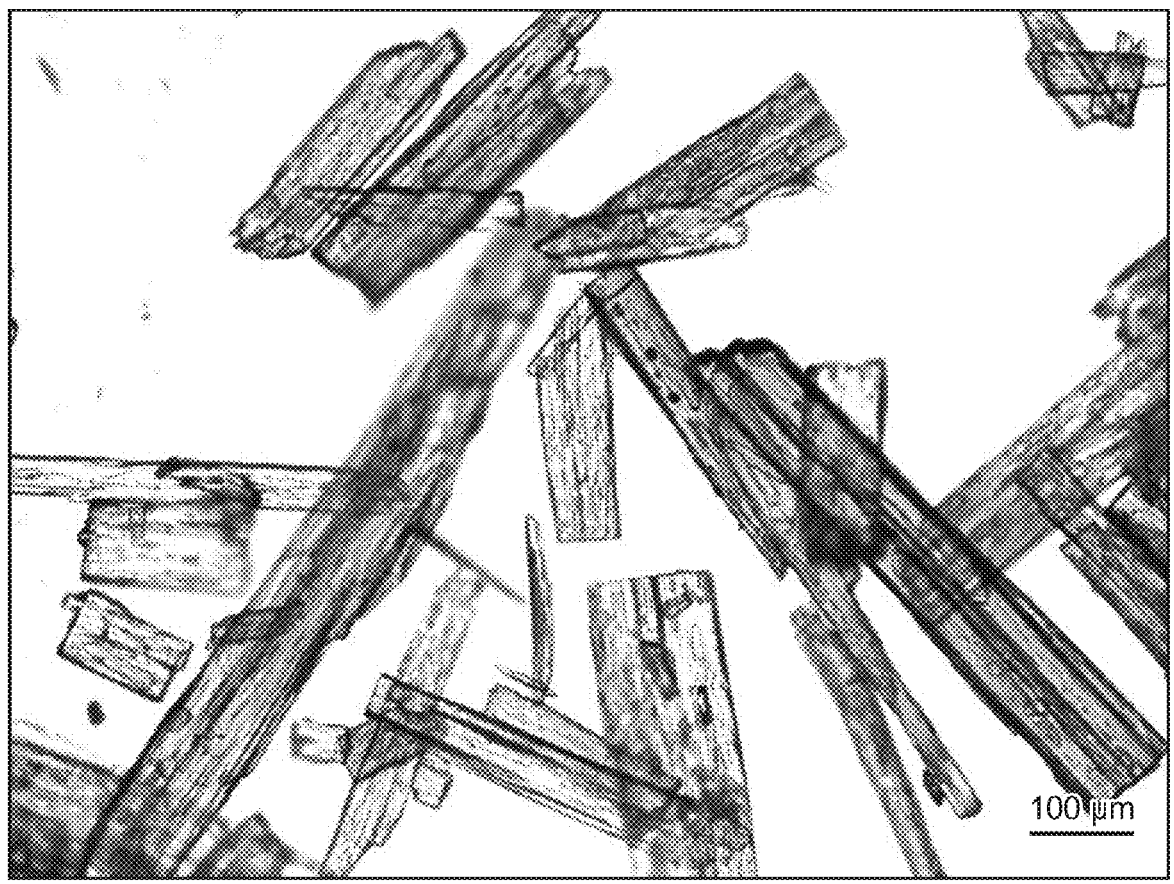
FIGS. 17A (where 100 μm scale is indicated in the bottom right corner) and 17B (where 20 μm scale is indicated in the bottom right corner) show microscopy images of ID-4-1 at 100× and 400× magnification, respectively.
Figure 17B:
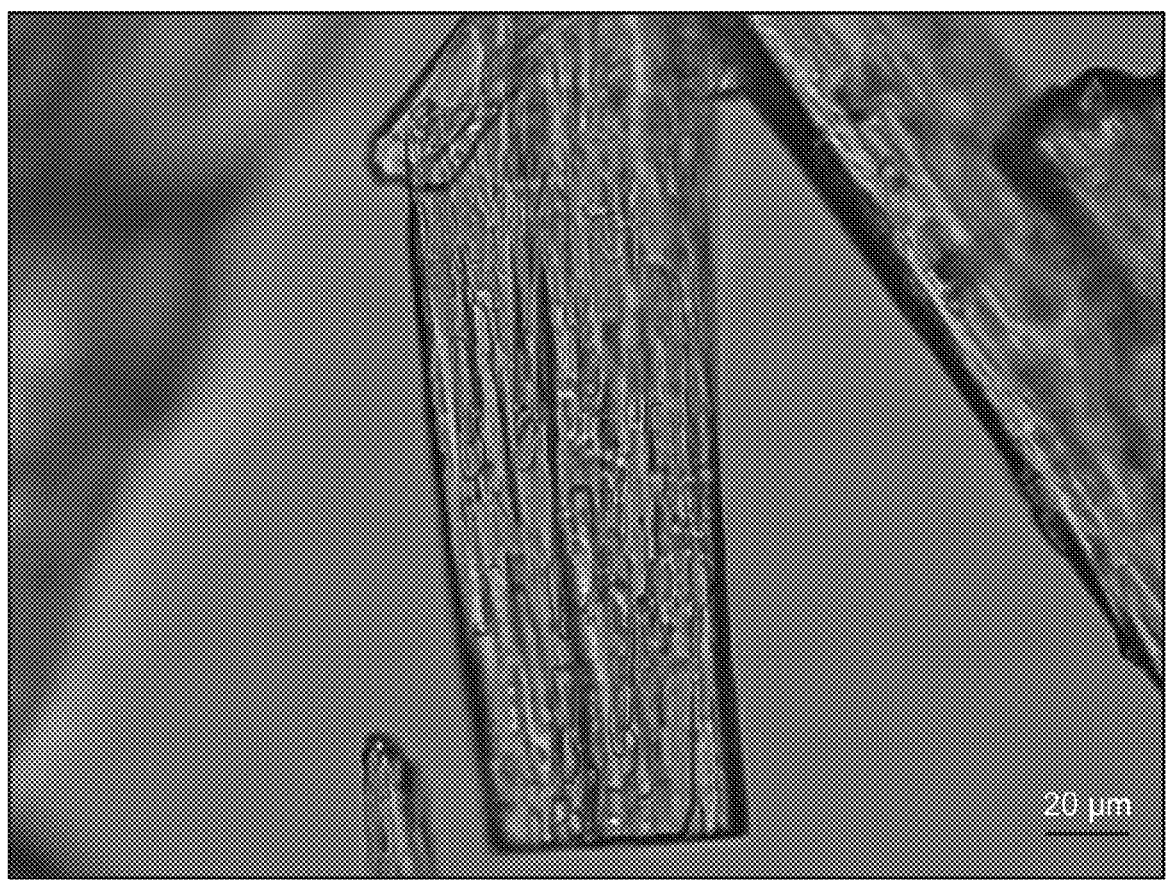

The resulting chromatogram did not show any impurities in the stability sample. The chromatogram is shown in FIG. 15. A sample of the stressed material was plated and analyzed by XRPD; the observed pattern was Pattern A. The XRPD data is shown in FIG. 16. Microscopy images of ID-4-1 were captured at 100× and 400× magnification. The images are shown in FIG. 17A (100×) and FIG. 17B (400×).

Figure 31:
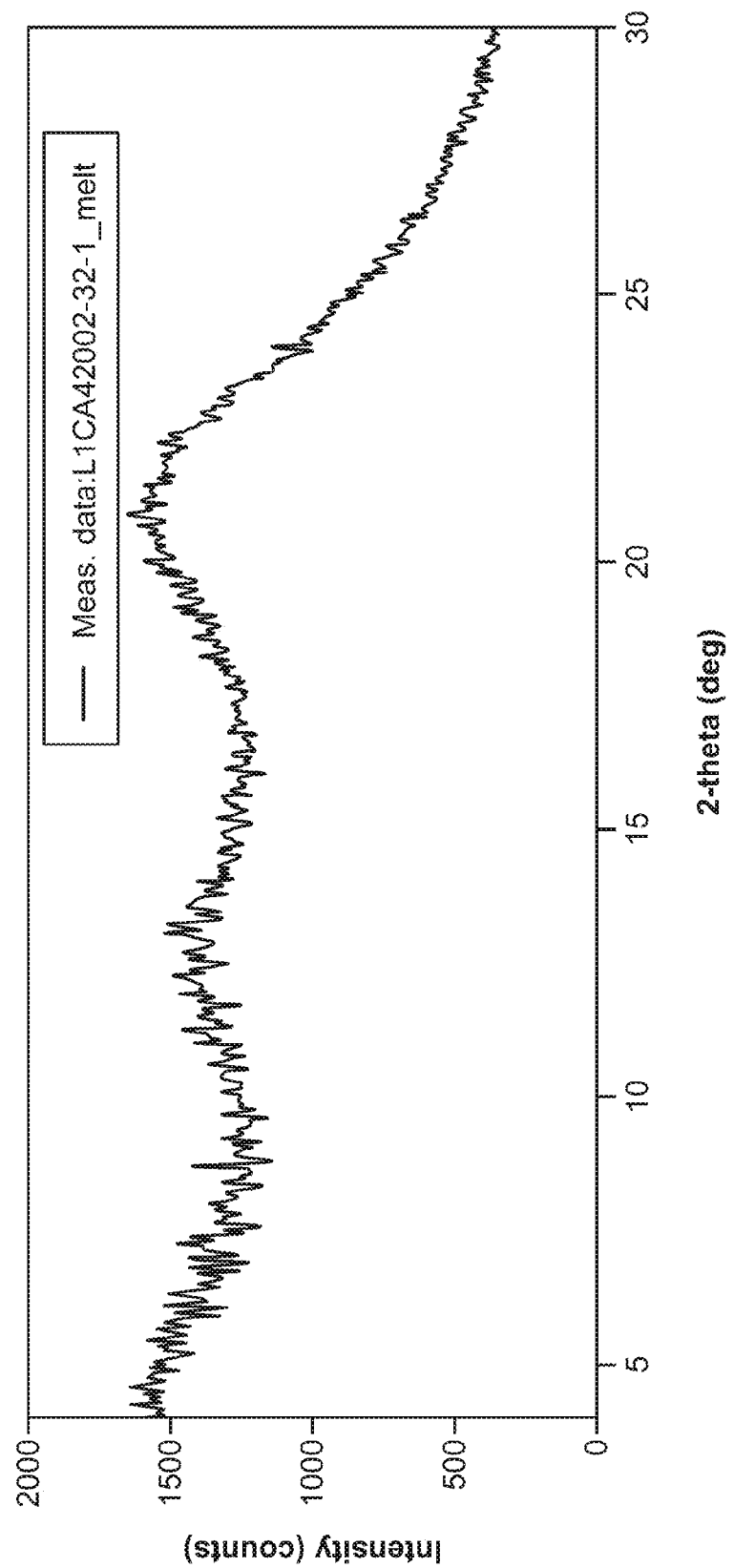
FIG. 31 is an XRPD diffractogram of liquid C9 cooled to room temperature for 5 minutes.
Figure 32:
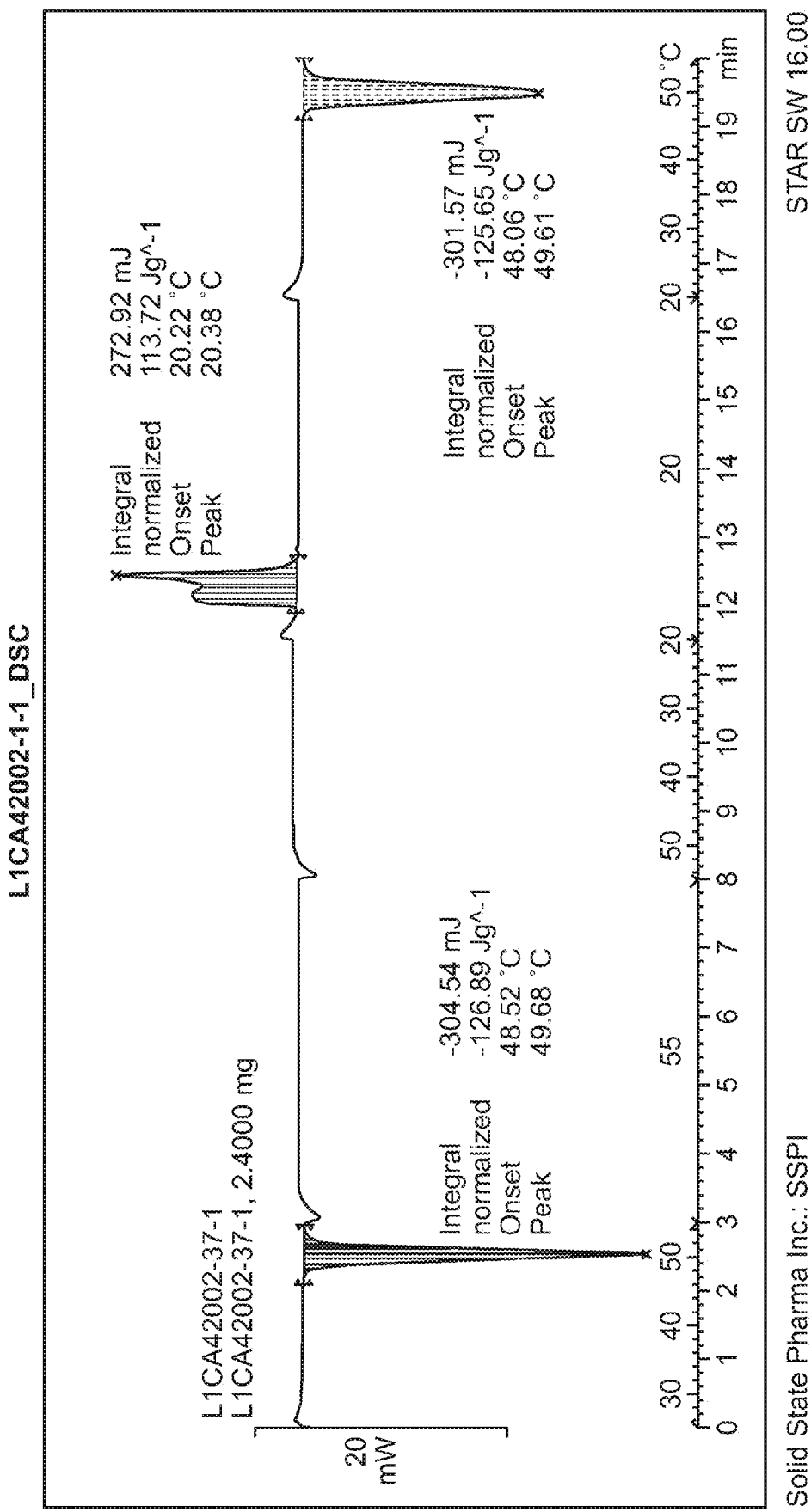
FIG. 32 is a DSC thermogram from temperature cycling experiment with less stressful conditions.

A sample of the solid form was heated at 55° C. until melted, then cooled to room temperature for 5 minutes, and an XRPD diffractogram showed it to be amorphous (FIG. 31). At 20° C., the melt eventually solidified into Pattern A, as seen in a temperature cycling DSC experiment (FIG. 32). This indicates that the amorphous liquid form is metastable, and converts to Pattern A.

Solubility in Simulated Fluids and Water.

Solubility of Pattern A and melted solid was assessed in Fasted-State Simulated Gastric Fluid (FaSSGF), Fed-State Simulated Intestinal Fluid (FeSSIF), and Fasted-State Simulated Intestinal Fluid (FaSSIF), water, and 0.5% methyl cellulose +2% Tween80 in water. Five foil-covered 4 mL vials were prepared with 11-13 mg of as-received material (ID-1-1), 10 mm stir bars were included. Five foil-covered 4 mL vials containing between 11-13 mg of C9 were melted on a hot plate at 70° C. for 10 min and cooled to room temperature for 5 min, 10 mm stir bars were included.

Slurries were prepared with the as-received material ID-1-1 (Pattern A) and melted C9, each in 2.5 mL of simulated fluids (including 0.5% methyl cellulose +2% Tween80 in water), or water. The samples containing melted active pharmaceutical ingredient (API) were sonicated briefly, as they appeared to contain clumps of material. Both pH and solubility were assessed at 30 minutes and 24 hours. For solubility analysis 1 mL of each sample was pipetted into a syringe filter, the first 0.5 mL was filtered back into the source vial and the remaining 0.5 mL was filtered into HPLC vials with low volume inserts.

The response factor calculated with the calibration points was used to determine the concentrations of API in the simulated fluids and water. Calibration samples were prepared with as-received material (ID-1-1) in ACN. The concentrations and peak areas for each calibration point were plotted and a response factor calculated for solubility assessment.

The experimental design and resulting data are shown in Table 5. The remainder of each slurry was filtered and plated for XRPD analysis. All patterns observed were Pattern A (data not shown).

TABLE 5

Experimental design and resulting data from solubility in simulated fluids and water

| Pattern | Fluid | Conc. (mg/mL) at 30 min* | Conc. (mg/mL) at 24 h* | pH of pure fluid | pH at 30 min | pH at 24 hr | XRPD |
|---|---|---|---|---|---|---|---|
| A | FaSSGF | BDL | BDL | 1.63 | 1.51 | 1.60 | A |
|   | FeSSIF | 0.29 | 0.20 | 4.95 | 4.90 | 4.82 | A |
|   | FaSSIF | 0.01 | BDL | 6.55 | 6.48 | 6.44 | A |
|   | 0.5% MC + 2% Tween80 (aq.) | 0.53 | 0.31# | 3.38 | 3.52 | 3.62 | A |
|   | water | BDL | BDL | ~7.00 | 6.65 | 6.82 | A |
| A (melted) | FaSSGF | BDL | BDL | 1.63 | 1.48 | 1.62 | A |
|   | FeSSIF | 0.25 | 0.20 | 4.95 | 4.87 | 4.83 | A |
|   | FaSSIF | 0.02 | 0.04 | 6.55 | 6.54 | 6.44 | A |
|   | 0.5% MC + 2% Tween80 (aq.) | 0.22 | 0.28# | 3.38 | 3.61 | 3.65 | A |
|   | water | BDL | BDL# | ~7.00 | 7.18 | 7.29 | A |

*BDL: below detection limit
With Phenomenex Luna Phenyl Hexyl HPLC column and modified method.

Due to high pressures observed with the UPLC column, a different column and a modified method was employed for 24 h data points with 0.5% methyl cellulose +2% Tween80 in water, and 24 h in water (ID-30-4, ID-30-9 and ID-30-10). HPLC samples of ID-30-4 and 30-9 (those containing the methyl cellulose/Tween80 mixture) were diluted 10× with ACN. These samples plus a new set of injections of the calibration points were analyzed, a new response factor was determined, and the solubility of the remaining samples was calculated (response factor: 8084.7908; R2: 0.9989).

Example 5. Crystal Morphology of C9 from Examples 3A and 3B

Summary.
Material from lots as described in Examples 3A and 3B were visually yellow, crystalline solids.

Multiple microscopy images were taken for each lot at 3 different magnifications (25×, 10×, 400×) to avoid bias when capturing images. The first lot, ID-38-1 (Example 3B), demonstrated mostly larger particles by microscopy, ranging from approximately 100 μm to over 600 μm. Overall, the particles were regular shaped, rectangular and somewhat planar in shape, and demonstrated good birefringence.

The second lot, ID-38-2 (Example 3A), demonstrated significantly smaller particles overall when compared to the first lot. A range of particles between approximately 50-350 μm were observed, and these particles tended to be more granular or irregular in shape. There was also notable agglomeration of smaller particles stuck to the larger particles, unlike the first lot in which individual particles were consistently observed.

Results.
Microscopy was carried out on ID-38-1 (Example 3B) at 3 different magnifications: 25×, 100×, and 400×. This particular lot of C9 demonstrated a wide range of particle sizes, by microscopy.

Figure 18:
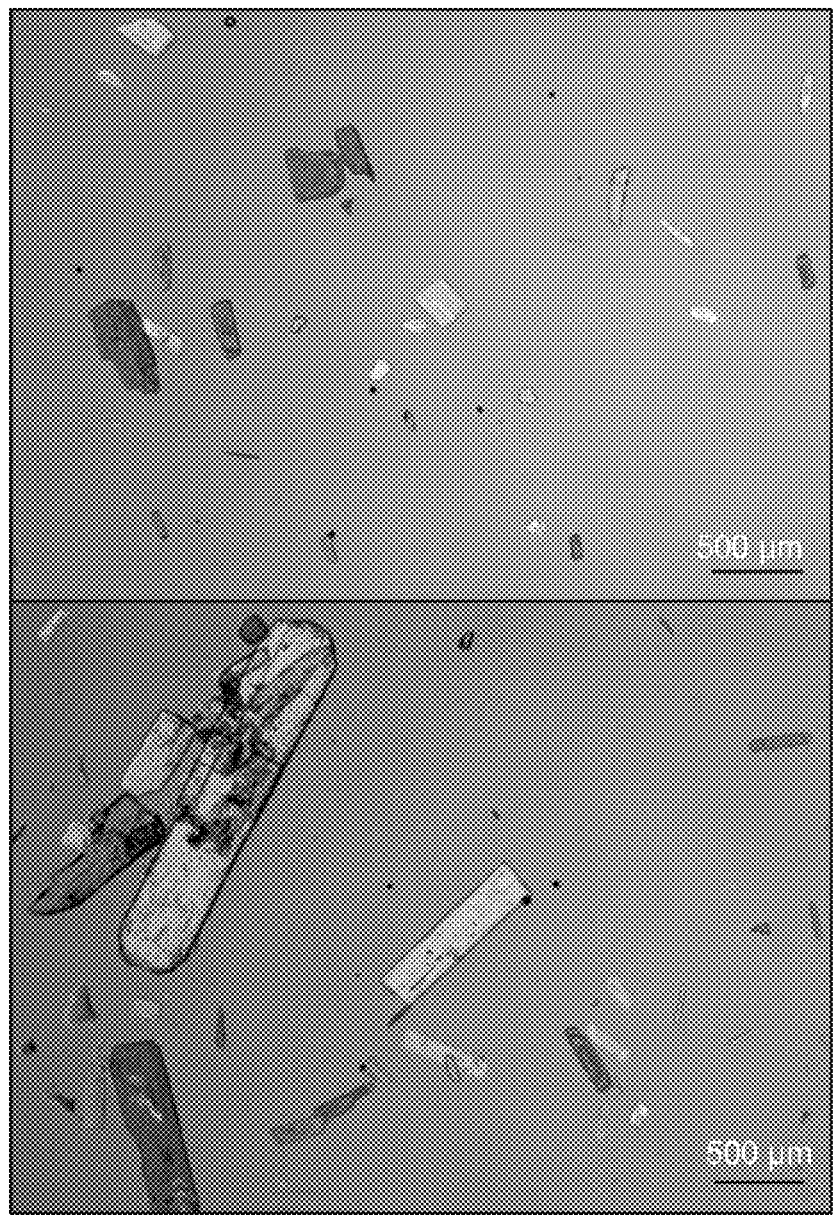
FIG. 18 shows microscopy images of ID-38-1 at 25× magnification, where 500 μm scale is indicated in the bottom right corner.
Figure 19:
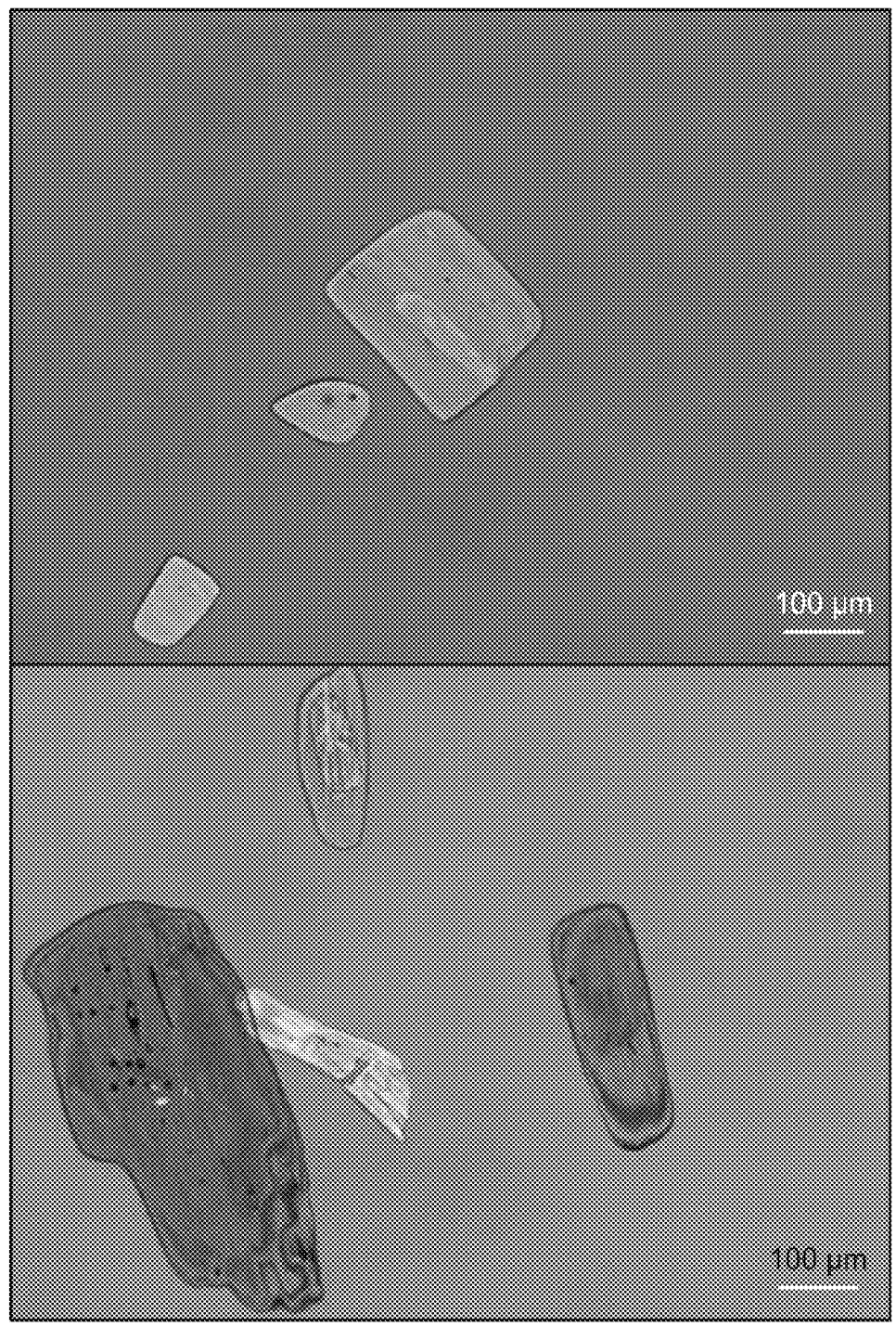
FIG. 19 shows microscopy images of ID-38-1 at 100× magnification, where 100 μm scale is indicated in the bottom right corner.
Figure 20:
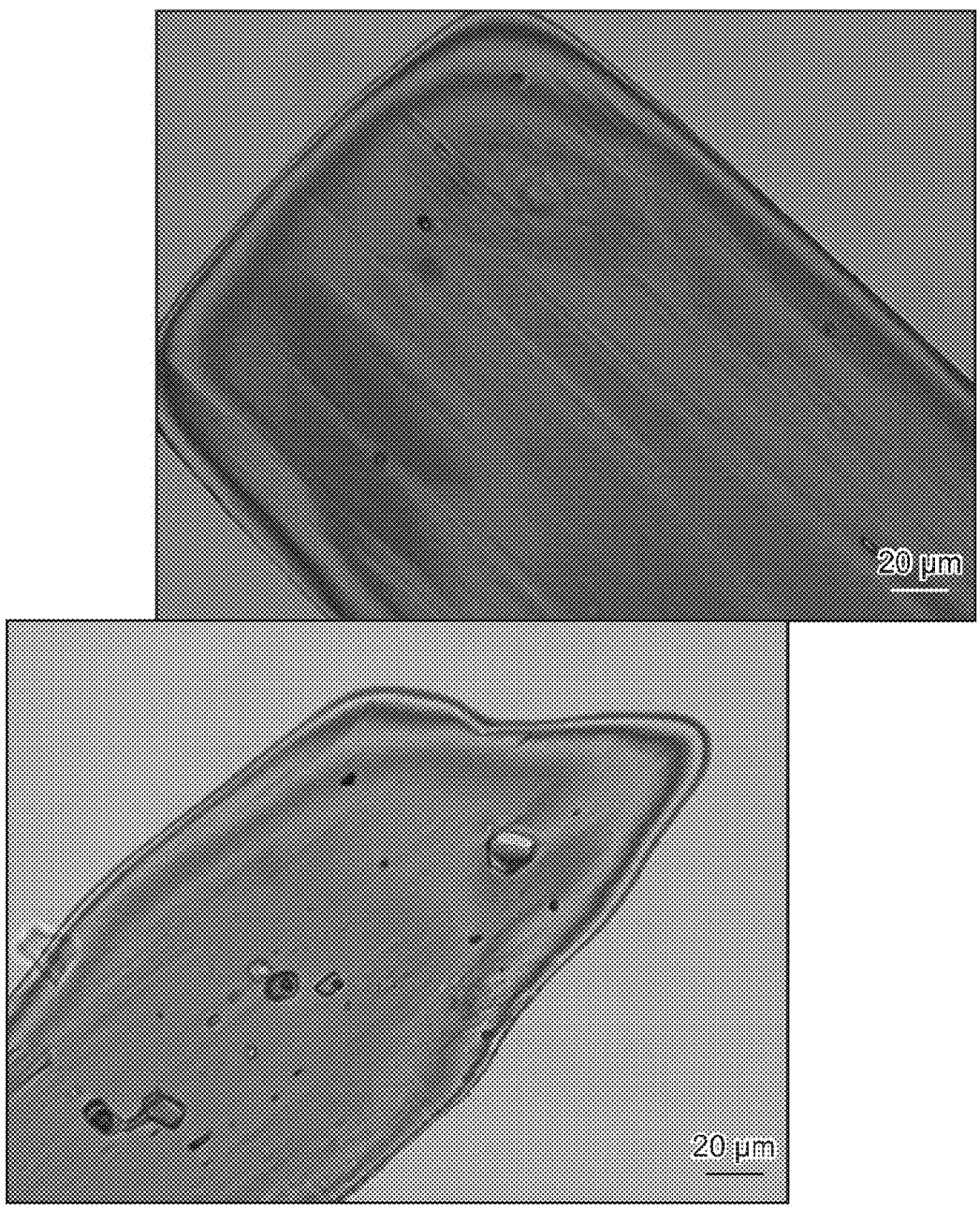
FIG. 20 shows microscopy images of ID-38-1 at 400× magnification, where 20 μm scale is indicated in the bottom right corner.

In FIG. 18, 25× magnification, it was possible to see the variance in particle sizes and shapes. Predominantly, rectangular plates were observed; however, there were also some jagged 2-dimensional shapes as well. At 100× magnification, FIG. 19, lengths range from approximately 100 μm-600 μm; birefringence was observed. At 400× magnification, the particles were too large to fit within the frame, but the smooth rectangular birefringent shapes were observed well (FIG. 20).

Microscopy was carried out on ID-38-2 (Example 3A) at 3 different magnifications: 25×, 100×, and 400×. This particular lot of C9 demonstrated smaller particles overall when compared to ID-38-1 (Example 3B), less birefringence, and more small agglomerated particles 'stuck' to some of the larger particles observed.

Figure 21:
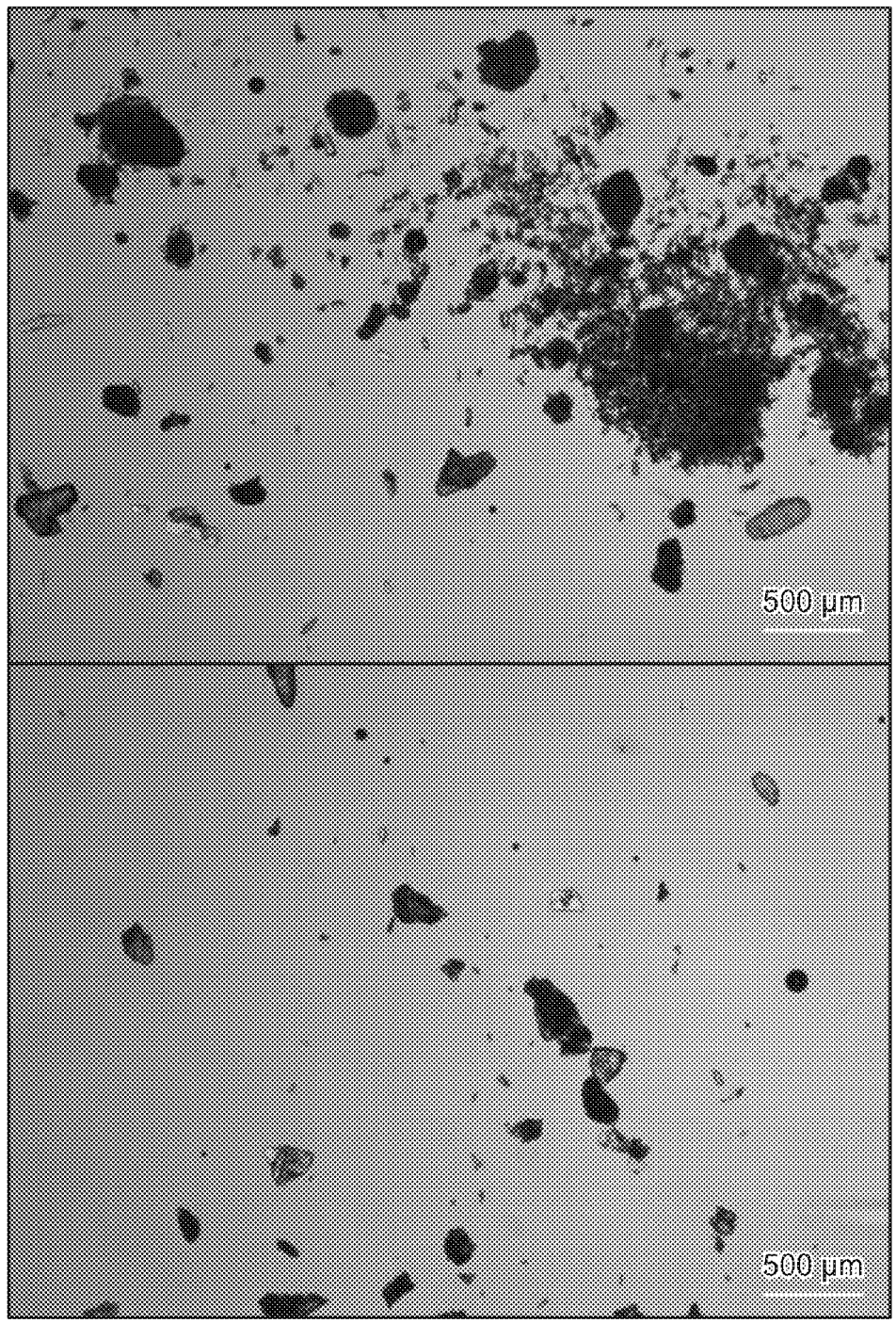
FIG. 21 shows microscopy images of ID-38-2 at 25× magnification, where 500 μm scale is indicated in the bottom right corner.
Figure 22:
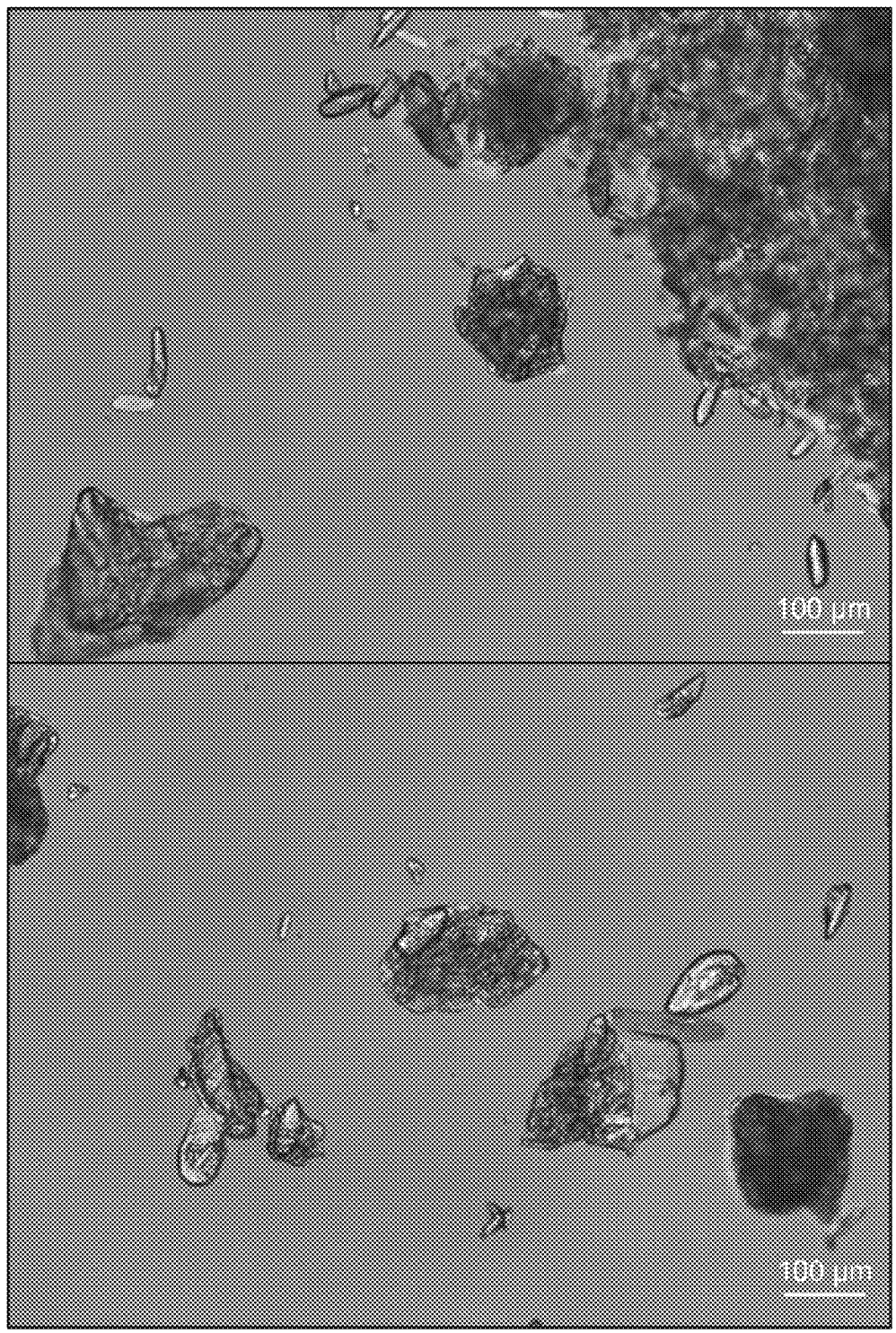
FIG. 22 shows microscopy images of ID-38-2 at 100× magnification, where 100 μm scale is indicated in the bottom right corner.
Figure 23A:
FIGS. 23A and 23B shows microscopy images of ID-38-2 at 400× magnification, where 20 μm scale is indicated in the bottom right corner.
Figure 23B:
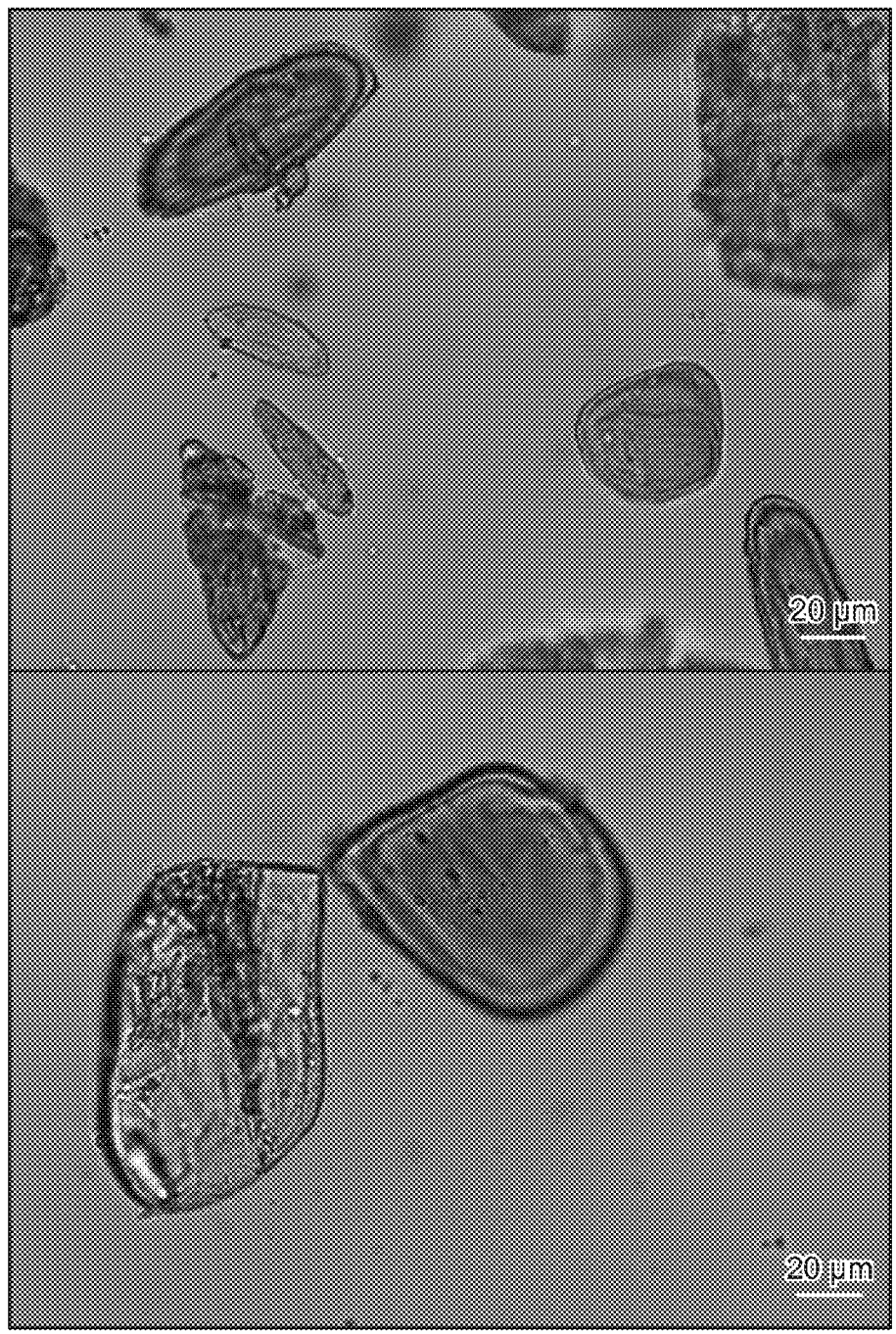

In FIG. 21, small agglomerated particles were observed at 25× magnification. At 100× magnification, FIG. 22, granular shape particles became more visible ranging from approximately 50 μm-350 μm. Several smaller agglomerated particles were observed as well. At 400× magnification, FIGS. 23A and 23B, the particles were observed within the frame, unlike with ID-38-1 (Example 3B). Translucent particles were observed in a spherical-like shape, and birefringence was also observed for many of the particles. Multiple images were captured at this magnification to demonstrate the large range in particle sizes observed, as well as to view the smaller particles which were agglomerated onto some of the larger solids.

Figure 24:
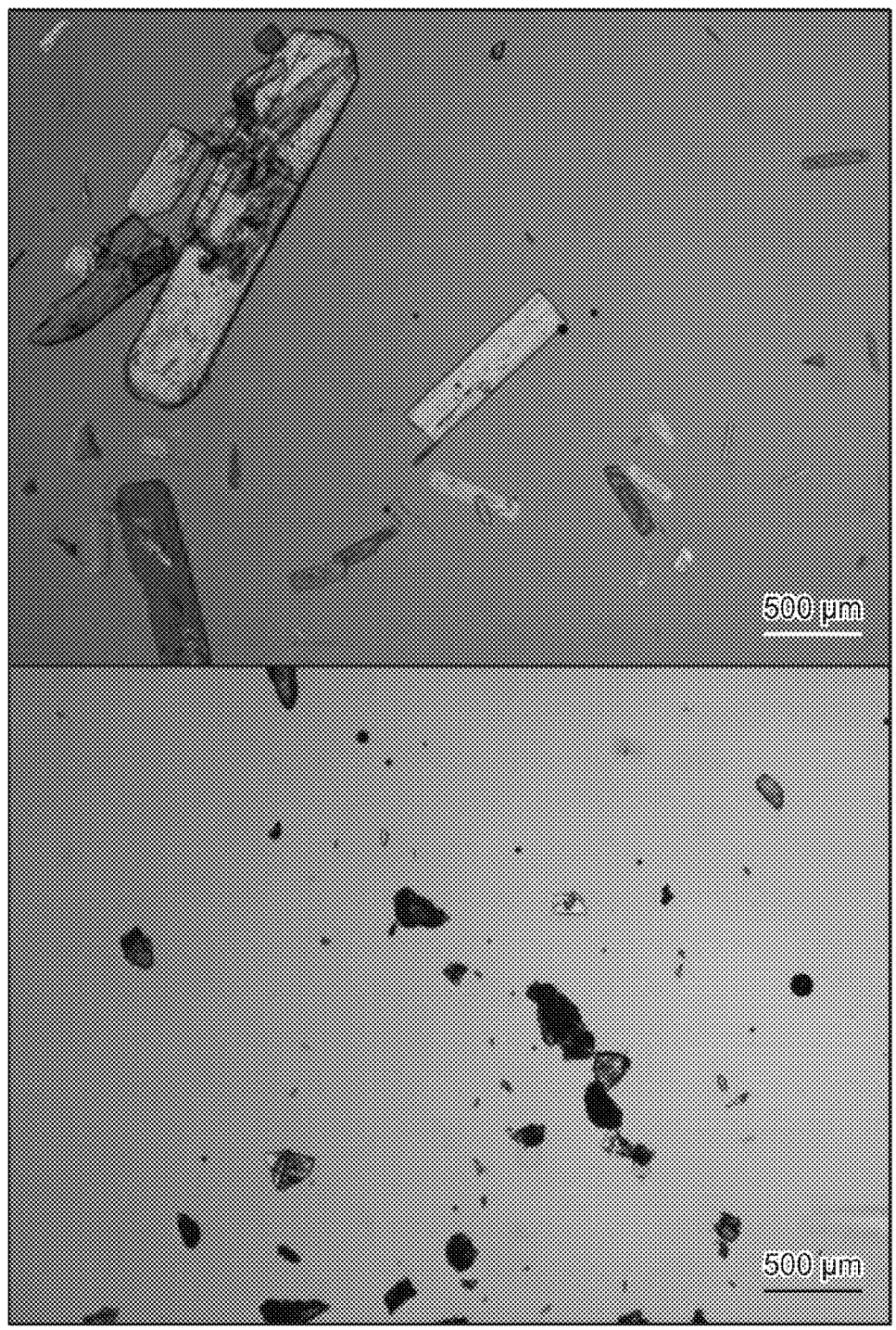
FIG. 24 shows microscopy comparing both lots ID-38-1 (top) and ID-38-2 (bottom) at 25× magnification, where 500 μm scale is indicated in the bottom right corner.
Figure 25:
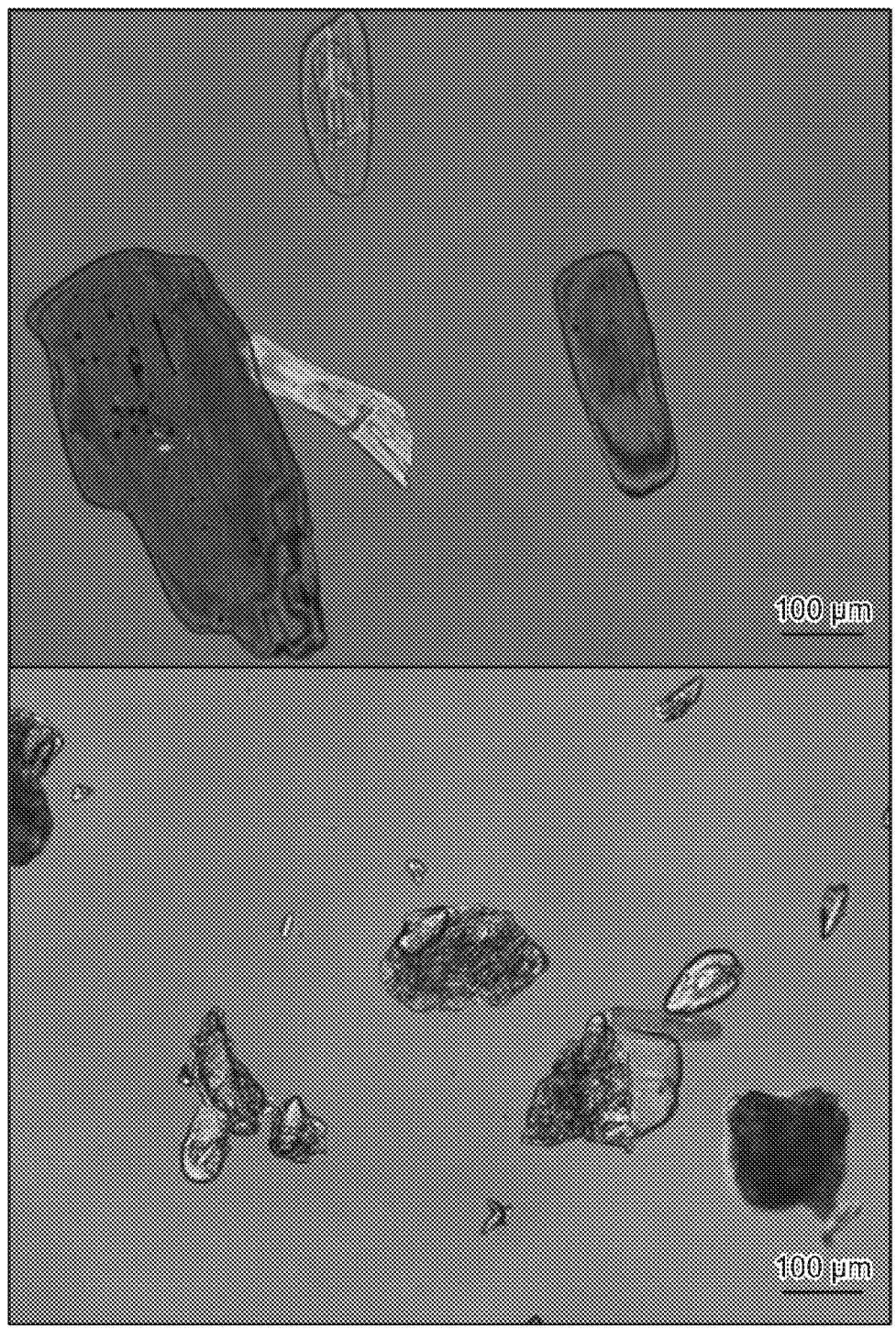
FIG. 25 shows microscopy comparing both lots ID-38-1 (top) and ID-38-2 (bottom) at 100× magnification, where 100 μm scale is indicated in the bottom right corner.
Figure 26:
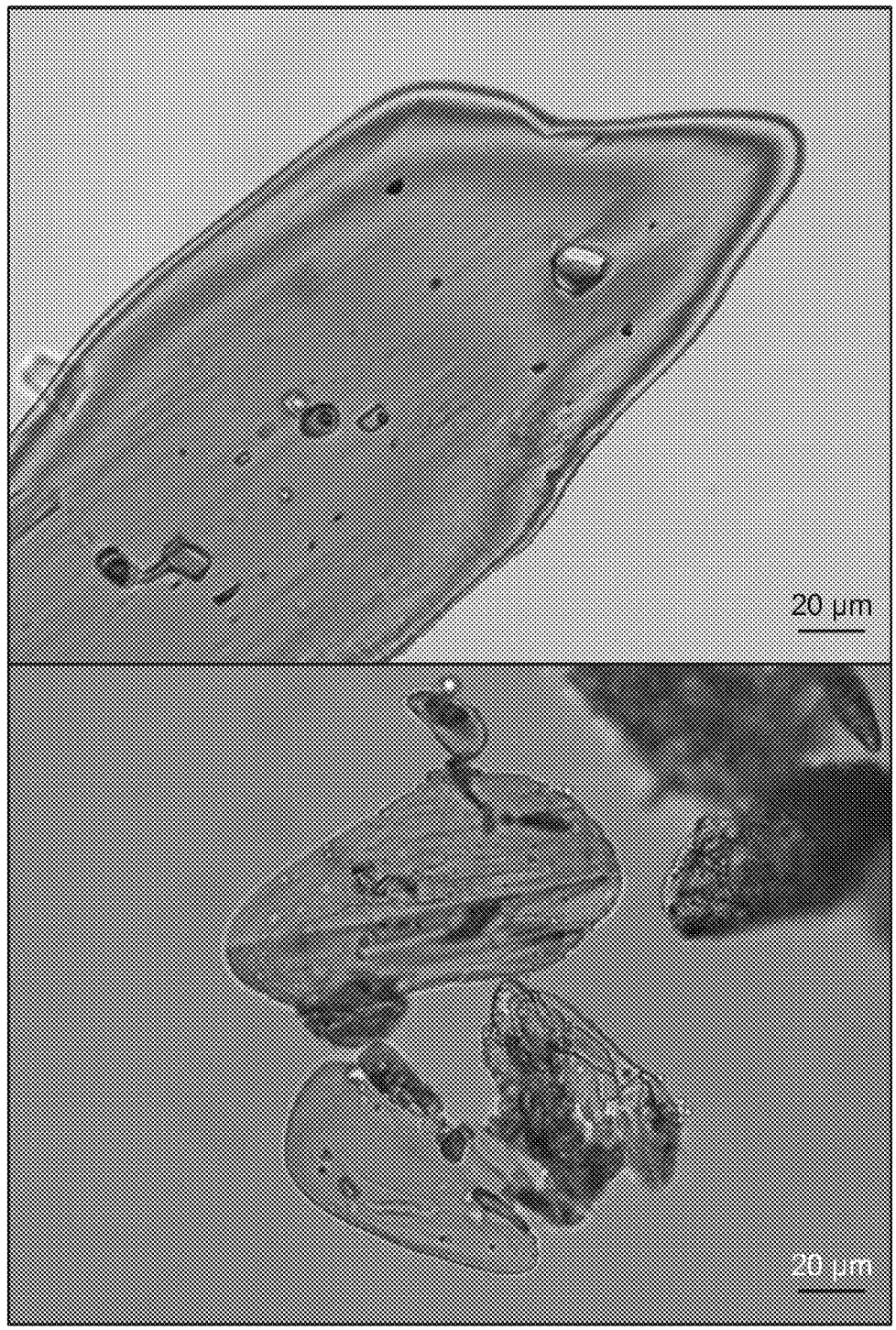
FIG. 26 shows microscopy comparing both lots ID-38-1 (top) and ID-38-2 (bottom) at 400× magnification, where 20 μm scale is indicated in the bottom right corner.

Comparison of Lots.
A direct comparison was given below of ID-38-1 (Example 3B) and ID-38-2 (Example 3A). At 25× magnification the difference in morphology and size was quickly observed between the two lots, FIG. 24. In FIG. 25, at 100× magnification, more individual particles were observed for ID-38-1 when compared to ID-38-02, in which small particles were observed agglomerated onto the larger ones. At 400× magnification, FIG. 26, the particles were too large to fit in the frame for ID-38-1 (Example 3B), but the smooth plate-like morphology was observed clearly, whereas small agglomerated particles onto larger solids was once again observed for ID-38-2 (Example 3A).

Microscopy
Optical microscopy was performed using a Zeiss Axio-Scope A1 digital imaging microscope equipped with 2.5×, 10×, 20× and 40× objectives and polarizer. Images are captured through a built-in Axiocam 105 digital camera and processed using ZEN 2 (blue edition) software provided by Zeiss.

Example 6. Particle Size Distribution C9 from Examples 3A and 3B

Summary. Particle size distribution for C9 from Example 3A (crude) and 3B (recrystallized) were determined using a Malvern 3000 Mastersizer.

Example 3A, Prep 1. 24.4 mg of C9 sample were weighed into a vial. Approximately 20 mL of water was added. 20 drops of 5% octylphenoxypolyethoxyethanol (IGEPAL) in water solution was added to vial. The solution was capped and gently mixed.

Example 3A, Prep 2. 25.2 mg of C9 sample were weighed into a vial. Approximately 20 mL of water was added. 20 drops of 5% IGEPAL in water solution was added to vial. The solution was capped and gently mixed.

Example 3B, Prep 1. 24.7 mg of C9 sample were weighed into a vial. Approximately 20 mL of water was added. 20 drops of 5% IGEPAL in water solution was added to vial. The solution was capped and gently mixed.

Example 3B, Prep 2. 25.2 mg of C9 sample were weighed into a vial. Approximately 20 mL of water was added. 20 drops of 5% IGEPAL in water solution was added to vial. The solution was capped and gently mixed.

Visual Observations of PSD Samples.
Example 3A samples were observed to be very non-uniform solids. Many large particles were observed in the samples. Both preps contained similar non-uniformity.

Very large crystals were observed in the Example 3B samples. Visual observation indicated either very small crystals to larger crystals in both sample preps. Sample 2 preparation contained more smaller/finer particles visually than the sample 1 prep.

Particle size distribution.
Particle size distribution was determined by laser diffraction, using a Malvern 3000 Mastersizer. Settings are shown in Table 6. The same settings were used for the other samples. Results are shown in Table 7.

TABLE 6

Malvern Instrument Settings for Example 3A, Prep 1

| Particle Type | |
| --- | --- |
| Non-spherical particle mode | Yes |
| Is Fraunhofer type | No |

TABLE 6-continued

Malvern Instrument Settings for Example 3A, Prep 1

Material Properties

| | |
|---|---|
| Refractive index | 1.480 |
| Absorption index | 0.001 |
| Particle density | 1.00 g/cm$^3$ |
| Different optical properties in blue light | Yes |
| Refractive index (in blue light) | 1.480 |
| Absorption index (in blue light) | 0.001 |

Dispersant properties

| | |
|---|---|
| Dispersant name | Water |
| Refractive index | 1.330 |
| Level sensor threshold | 100.000 |

Measurement Duration

| | |
|---|---|
| Background measurement duration (red) | 15.00 s |
| Sample measurement duration (red) | 15.00 s |
| Perform blue light measurement? | Yes |
| Background measurement duration (blue) | 15.00 s |
| Sample measurement duration (blue) | 15.00 s |
| Assess light background stability | No |

Measurement sequence

| | |
|---|---|
| Aliquots | 1 |
| Automatic number of measurements | No |
| Pre-alignment delay | 0.00 s |
| Number of measurements | 3 |
| Delay between measurements | 0.00 s |
| Pre-measurement delay | 0.00 s |
| Close measurement window after measurement | No |

Measurement obscuration settings

| | |
|---|---|
| Auto start measurement | No |
| Obscuration low limit | 1.00% |
| Obscuration high limit | 10.00% |
| Enable obscuration filtering | No |

Measurement alarms

| | |
|---|---|
| Use Background Check | No |
| Background Check Limits | [1, 200], [20, 60] |

TABLE 7

Particle Size Distribution for C9 Samples.

| Combined Results (Two Preps, N = 3 for each Prep) | d(v, 0.1) (μm) (D10) | d(v, 0.5) (μm) (D50) | d(v, 0.9) (μm) (D90) |
|---|---|---|---|
| Example 3A | | | |
| Average | 59.78 | 278.83 | 926.00 |
| RSD (%) | 5.68 | 10.27 | 13.51 |
| Example 3B | | | |
| Average | 133.22 | 433.33 | 877.67 |
| RSD (%) | 43.71 | 13.54 | 5.71 |

Figure 27:
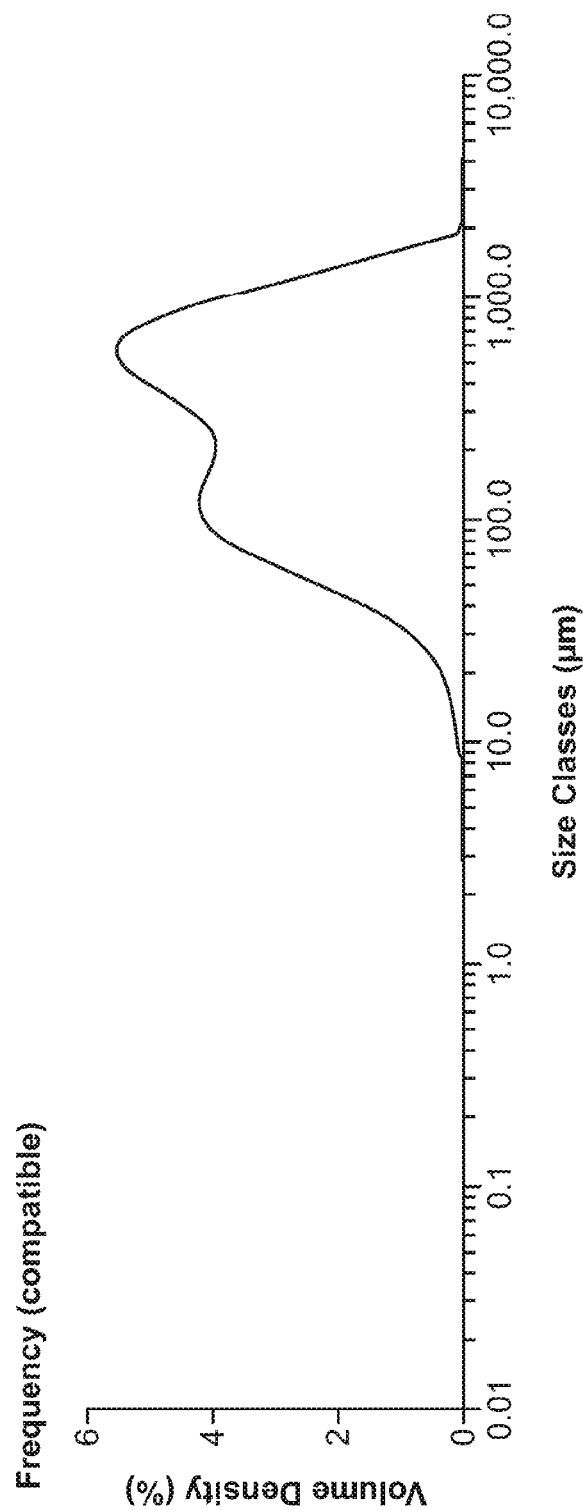
FIGS. 27 and 28 show particle size distribution for a representative experiment for material Example 3A, preps 1 and 2, respectively.
Figure 28:
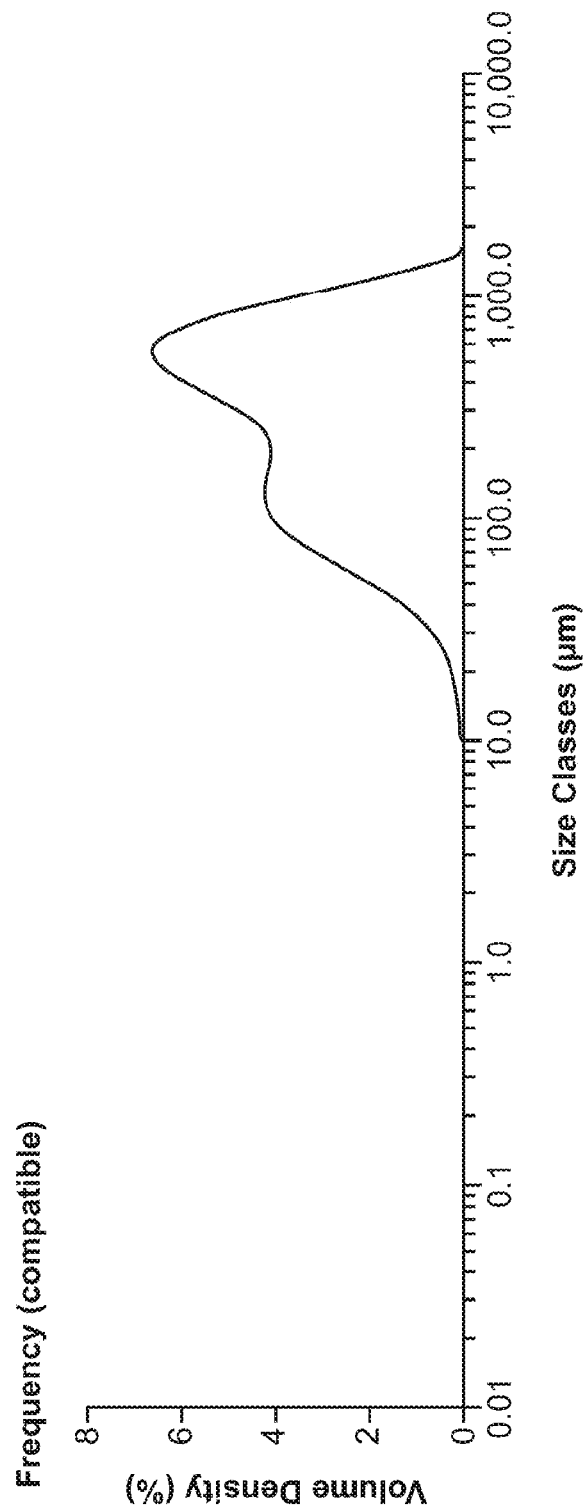
Figure 29:
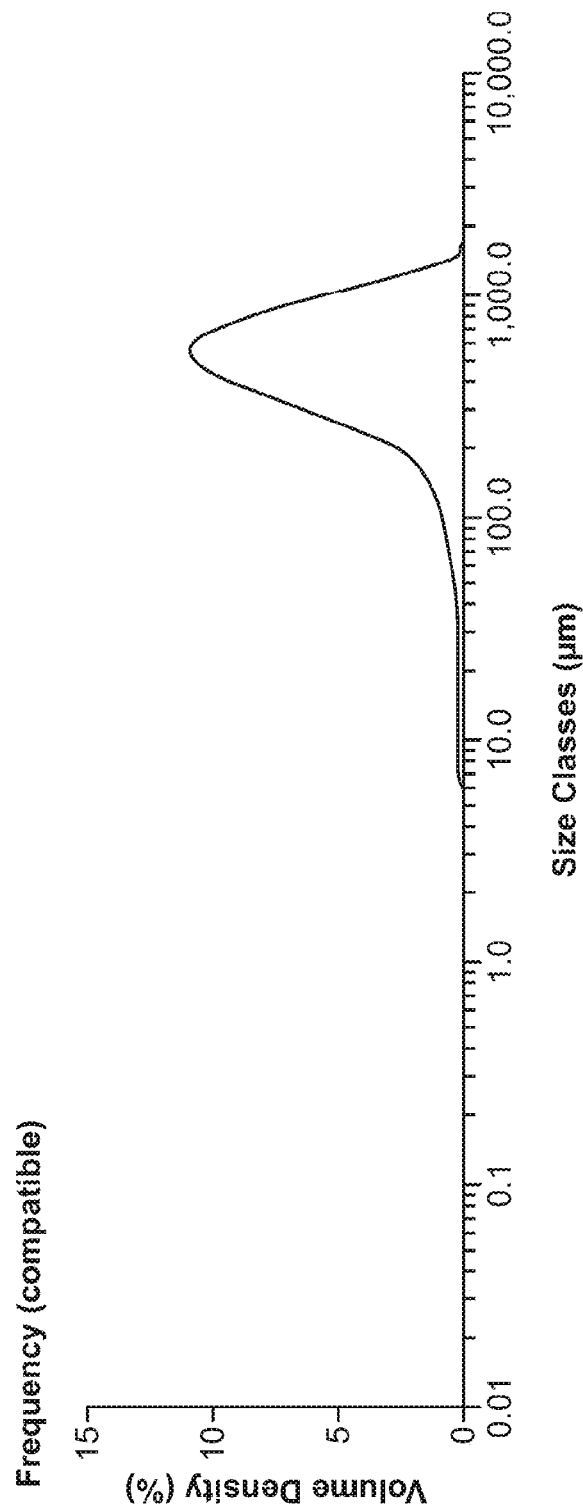
FIGS. 29 and 30 show particle size distribution for a representative experiment for material Example 3B, preps 1 and 2, respectively.
Figure 30:
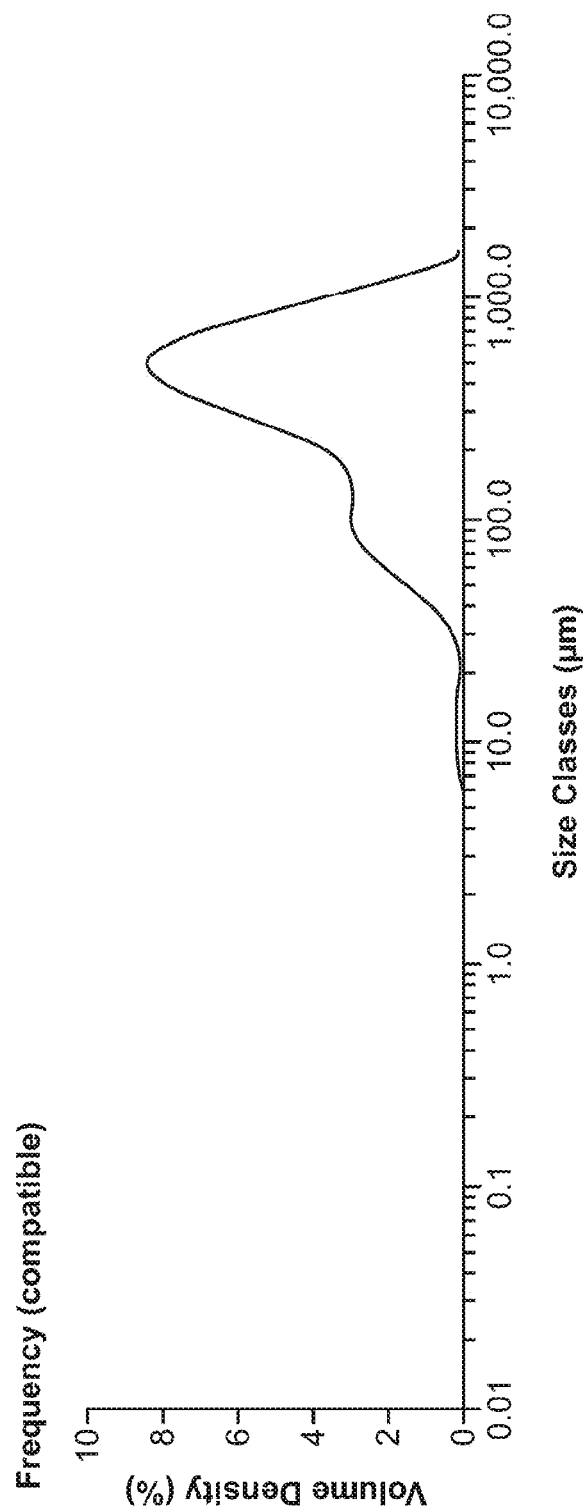

As shown in Table 7, both examples are comprised of fairly large particles, but 3B is quite larger on average: Ave. d (v, 0.5 um)=278 μm for 3A and 433 μm for 3B. However, 3A has a wider size distribution probably due to the partial milling (d(v, 0.1 to 0.9)=~60 μm to 925 μm for 3A versus d(v, 0.1 to 0.9=~133 to 878 μm) for 3B. A representative example of each analysis is shown in FIGS. 27 and 28 (Example 3A preps 1 and 2 and FIGS. 29 and 30 (Example 3B preps 1 and 2). As seen in FIGS. 27 and 29, Example 3A samples have a wider particle size distribution and also a bimodal characteristic compared to the Example 3B (recrystallized) samples. There is a narrower distribution range between D90 and D10 in the Example 3B samples (a ratio of 6.6:1), compared with the Example 3A samples (ratio of 15.5:1). D10 represents the particle diameter corresponding to 10% cumulative (from 0 to 100%) undersize particle size distribution (i.e. the percentage of particles smaller than D10 is 10%). D90 represents the particle diameter corresponding to 90% cumulative (from 0 to 100%) undersize particle size distribution (i.e. the percentage of particles smaller than D90 is 90%). Representative examples of each prep are shown in FIGS. 27-30 (Example 3A prep 1, Example 3A prep 2, Example 3B prep 1, Example 3B prep 2, respectively). As seen in FIGS. 27-30, Example 3A samples have a wider particle size distribution than the Example 3B (recrystallized) samples.

Example 7. Screening Compounds in Human Dermal Fibroblasts from Parkinson's Disease (PD) and Alzheimer's Disease (AD) Patients An initial screen was performed to identify the effectiveness of compounds for the amelioration of PD and AD. Test samples and solvent controls were tested for their ability to rescue PD and AD fibroblasts stressed by addition of L-buthionine-(S,R)-sulfoximine (BSO, a specific inhibitor of GSH synthetase) plus iron (e.g. iron citrate), in a similar manner as that described in Jauslin et al., Hum. Mol. Genet. 11(24):3055 (2002), Jauslin et al., FASEB J. 17:1972-4 (2003), and International Patent Application WO 2004/003565. This specific BSO-mediated cell death was prevented or ameliorated by administration of compounds described herein.

The AD experiments were performed as follows. PD experiments were performed in a similar manner; certain specific conditions are noted below in Table 1A.

MEM (a medium enriched in amino acids and vitamins) and Medium 199 (M199) with Earle's Balanced Salts (EBS), without phenol red, were purchased from Invitrogen. Fetal Calf Serum was obtained from Corning. Basic fibroblast growth factor (bFGF) and epidermal growth factor (EGF) were purchased from PeproTech. Penicillin-streptomycin-glutamine mix, L-buthionine (S,R)-sulfoximine, iron citrate, and insulin from bovine pancreas were purchased from Sigma. Calcein AM was purchased from Anaspec. Cell Culture Medium was prepared by combining 450 mL MEM, 50 mL Fetal Calf Serum, 100 U/mL penicillin, and 100 microgram/mL streptomycin. Assay medium was prepared by combining 125 mL M199, 50 mL Fetal Calf Serum, 100 U/mL penicillin, 100 microgram/mL streptomycin, 2 mM glutamine, 10 microgram/mL insulin, 10 ng/mL EGF, and 10 ng/mL bFGF; MEM was added to make the volume up to 500 mL. 10 mM BSO and 10 mM iron citrate solutions were prepared in water with subsequent filter-sterilization and stored at −20° C.

The test samples were supplied in 1.5 mL glass vials or polypropylene vials. The compounds were diluted with DMSO, to result in a 1 mM stock solution. Once dissolved, they were stored at −20° C.

Test samples were screened according to the following protocol:

A culture of AD or PD patient-derived fibroblasts was started from a vial with approximately 500,000 cells stored in liquid nitrogen. Cells were propagated in Cell Culture Medium, with subcultivation every third day by trypsinization at a ratio of 1:3. Once confluent, fibroblasts were harvested by trypsinization, resuspended in Assay Medium, and seeded at a final cell density of 2,500 cells/0.1 mL per well of a standard 96-well tissue culture plate. The plates were incubated 5 hours at 37° C. in an atmosphere with 95% humidity and 5% CO$_2$ to allow attachment of the cells to the culture plate, then iron citrate solution (in water) was added to the desired final concentration.

Test samples (1 mM in DMSO) were diluted in a 10% DMSO:water solution to a final concentration of 5 microM, then serially diluted in 10% DMSO to the desired concentrations. Cells were then treated with the various compound dilutions, resulting in a final DMSO concentration of 1%, and then incubated at 37° C. in an atmosphere with 95% humidity and 5% $CO_2$ for 18 hours.

The next day, BSO solution was added to the wells to result in the desired final concentration. Forty-eight hours later, the medium was discarded and the remaining liquid was removed by gently tapping the plate inverted onto a paper towel. The plates were washed once with 100 microliters per well of PBS containing Calcium and Magnesium (+Ca +Mg).

100 microliters of Calcein AM (1 microM) in PBS +Ca +Mg was then added to each well. The plates were incubated for 30 minutes at 37° C. After that time fluorescence (excitation/emission wavelengths of 485 nm and 525 nm, respectively) was read on a Spectramax fluorescence reader. Data were analyzed using standard four-parameter curve fit algorithms (XLFit or Prism) to determine the $EC_{50}$ concentration for each compound.

The solvents (DMSO, water) did not have a detrimental effect on the viability of non-BSO treated cells nor did they have a beneficial influence on BSO plus iron-treated fibroblasts even at the highest concentration tested (1%).

Test samples described herein were found to rescue fibroblast cells from Parkinson's Disease and Alzheimer's Disease patients from BSO plus iron-induced oxidative stress.

TABLE 8

Rescue of PD Patient Fibroblasts From BSO (125 μM) Plus Iron (125 μM)-Induced Oxidative Stress

| Compound (#C) | PD (ND29542) | | |
|---|---|---|---|
| | $EC_{50}$ (nM) | SEM | Max Rescue (@ 500 nM) |
| C6 | >500 | 20 | 39 |
| C8 | >500 | 97 | 73 |
| C9 | 84 | 4 | 103 |

$EC_{50}$ = concentration at which 50% maximal rescue of cell viability was observed
SEM = standard error of the mean.

The C9 compound also demonstrated activity in rescuing AD patient fibroblast cells from oxidative stress (Table 9).

Example 8. Screening Compounds for Inhibition of α-Synuclein Aggregation

Summary: The compound 2,3,5-trimethyl-6-nonylcyclohexa-2,5-diene-1,4-dione ("C9"), and its C8 (2,3,5-trimethyl-6-octylcyclohexa-2,5-diene-1,4-dione) and C7 (2,3,5-trimethyl-6-heptylcyclohexa-2,5-diene-1,4-dione) analogs were tested for their function as inhibitors of αSynuclein aggregation, as measured by the presence and extent of a lag phase in the kinetics of protein aggregation. Changes in the fluorescence intensity by the aggregate-binding fluorophore, Thioflavin T, were followed to report on the protein aggregation as a function of time.

Experimental Methods: Cell-free αSynuclein aggregation assays were set up with 200 μM of recombinant human αSynuclein (Proteos, Inc.) in the presence of 100 μM of compound (from 10 mM stock solutions in DMSO) or in 1% (v/v) DMSO as vehicle. All solutions were prepared in Dulbecco's phosphate-buffered saline (DPBS) buffer (pH 7.4) with 0.03% (v/v) $NaN_3$ and 5 μM Thioflavin T (ThT), prepared as a master mix before addition of the protein or compounds. A protein master mix was then prepared and separated into 4 tubes (1 per condition). In parallel, a master mix was created for background measurements, under identical conditions except there was no protein added to the solution. Compounds or DMSO were loaded in each sample, vortexed for 10 seconds and centrifuged for 3 seconds.

Protein solution +/− compound and background samples were then loaded into wells of an optically transparent 96-well plate with black walls (Corning Costar), which was sealed with a LightCycler® 480 seal (Roche Life Science), incubated at 37° C. for 15 minutes to equilibrate, after which the data collection was started. A Tecan M1000 spectrometer was used to collect data points on ThT fluorescence (ex/em 450/490 nm) every 30 minutes. The plate was agitated by shaking in between fluorescence reads.

Data Analysis and Results: Fluorescence intensity data were collected on all the samples over time. The endpoint fluorescence intensity unit (HU) value of the mean of vehicle-treated αSyn samples was set to 100%, and all other HU values were normalized relative to it (see FIG. 1A). The end results were plotted as normalized ThT fluorescence (%) with respect to time.

TABLE 9

Rescue of AD Patient Fibroblasts From BSO-Plus Iron-Induced Oxidative Stress by C9

| | $EC_{50}$ (nM) | | | |
|---|---|---|---|---|
| Cell line | Iron citrate (50 μM) + BSO (50 μM) | Iron citrate (100 μM) + BSO (25 μM) | Iron citrate (100 μM) + BSO (100 μM) | Iron citrate (200 μM) + BSO (100 μM) |
| ND34730 | 15 | 24 | — | — |
| ND41001 | 13 | 17 | — | — |
| AG04402 | — | — | 5 | 12 |
| AG11414 | — | — | 11 | 23 |

— = not tested

As noted in Table 8, the C9 compound (2,3,5-trimethyl-6-nonylcyclohexa-2,5-diene-1,4-dione) had greater potency than the C6 and C8 analogs in rescuing PD fibroblasts from BSO- plus iron-mediated oxidative stress.

Figure 1B:
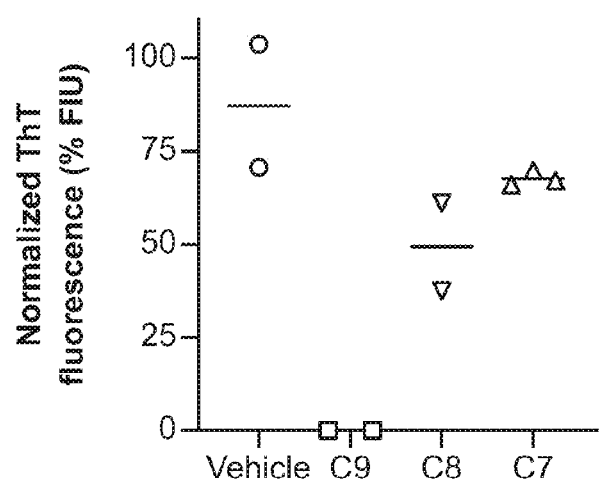
FIG. 1B shows fibril content of αSyn in the absence (vehicle) or presence of C9, C8, or C7 at t=24 hours of fibrilization. The fibril content was assessed based on relative ThT fluorescence intensity (100% was set to the endpoint value at t=45.5 hr of the average of vehicle-treated αSyn samples).

Normalized ThT fluorescence values (% FIU) at t=24 hours were used to compare samples (see FIG. 1B). At least 2 technical replicates were used per condition. Statistical analysis of samples was performed via ordinary one-way ANOVA analysis. Tukey's multiple comparisons test was conducted over all the protein-containing samples, which showed statistical significance between the vehicle and the C9-treated samples (p=0.0041), C9-treated vs. C7-treated samples (p=0.0085) and C9-treated vs. C8-treated samples (p=0.0437). All other comparisons were not statistically significant (i.e. ns), with p>0.05.

As shown in FIGS. 1A and 1B, the C9 compound has a significant inhibition effect on αSynuclein aggregation, and shows greater inhibition than either the C7 or C8 analogs.

Example 9. 2,3,5-Trimethyl-6-nonylcyclohexa-2,5-diene-1,4-dione (C9) and its Structural Analogs' Potency in Tau K18 WT Pre-Formed Fibril Disaggregation Summary: Compounds 2,3,5-trimethyl-6-nonylcyclohexa-2,5-diene-1,4-dione (C9), 2,3,5-trimethyl-6-octylcyclohexa-2,5-diene-1,4-dione (C8), and 2,3,5-trimethyl-6-heptylcyclohexa-2,5-diene-1,4-dione (C7) were tested for their ability to disaggregate pre-formed fibrils (PFFs) of human wild-type Tau K18 fragment, as measured by the decrease in fluorescence intensity of the aggregate-binding fluorophore, Thioflavin T, over time.

Experimental Methods: Pre-formed fibrils (PFFs) of the human recombinant Tau K18 WT fragment were generated by incubating the Tau K18 monomer (Bio-Techne®) with sodium heparin in a 1:1 ratio in presence of excess (50×) tris(2-carboxyethyl)phosphine (TCEP) as the reducing agent in Dulbecco's phosphate-buffered saline (DPBS) buffer (pH 7.4). The mixture was incubated for 4 days at 37° C. without agitation to yield PFFs in 100 μM final concentration.

Cell-free Tau disaggregation assays were set up with 10 μM of Tau PFFs in the presence of 30 μM of compound (from 10 mM stocks in DMSO) or in 0.3% (v/v) DMSO as vehicle. All solutions were prepared in DPBS buffer (pH 7.4) with 0.03% (v/v) $NaN_3$ and 5 μM Thioflavin T (ThT), prepared as a master mix before addition of the protein or compounds. A protein master mix was first prepared the day before the assay to pre-equilibrate the Tau PFFs at 10 μM at ambient temperature and atmosphere. The next day, the pre-mixed protein solution was separated into 4 tubes (1 per condition). Compounds or DMSO were loaded in each sample, vortexed for 10 seconds and centrifuged for 3 seconds, followed by a 15-minute incubation at ambient temperature. In parallel, a master mix was created for background measurements, under identical conditions except with no protein added.

Tau PFFssolution +/− compound and background samples were then loaded into wells of an optically transparent 96-well plate with black walls, which was sealed with a LightCycler® 480 seal (Roche Life Science), incubated at 37° C. for 15 minutes to equilibrate and the data collection was initiated. A Tecan M1000 spectrometer was used to collect data points on ThT fluorescence (ex/em 450/490 nm) every 30 minutes without agitation.

Data Analysis and Results: The maximum fluorescence intensity unit (FIU) value of the vehicle-treated Tau samples was set to 100%, to which all other FIU values were normalized relatively. At least 2 technical replicates were used per condition. Endpoint values of the fibril content of all samples 94 hours after assay initiation were reported (FIG. 2).

Statistical analysis of samples was performed via ordinary one-way ANOVA analysis. Dunnett's multiple comparisons test was conducted between vehicle-treated vs. compound-treated Tau PFF samples, which showed statistical significance between the vehicle and the C9-treated samples (p=0.0478).

Figure 2:
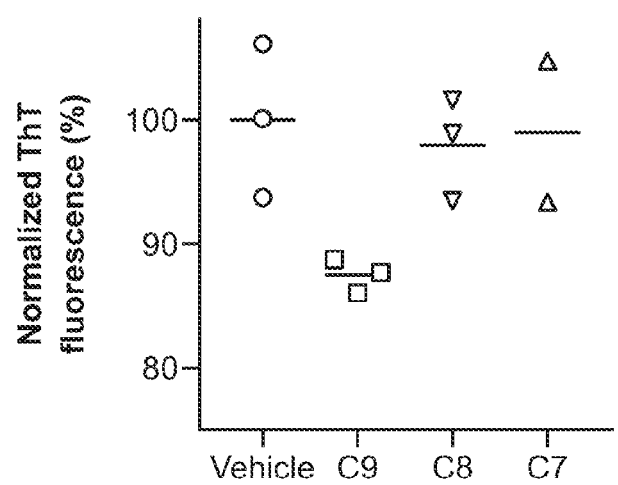
FIG. 2 shows the effect of vehicle, C9, C8, or C7 treatment on Tau pre-formed fibril content after 94 hours of incubation.

As shown in FIG. 2, the C9 treated sample had a significant reduction in Tau fibril content at 94 hr. In contrast, the C7 and C8 treated samples did not have a significant reduction in fibril content at 94 hr.

Example 10. Inhibition of RSL3-Induced αSynuclein Aggregation

N27 rat dopaminergic cells (purchased from EMD Millipore, SCC048) were transformed to stably overexpress truncated α-Synuclein fused with green fluorescent protein (GFP) with a plasmid construct obtained from Origene (RG221446). Cells were maintained in selection media which consisted of RPMI 1640 media supplemented with 10% (v/v) fetal bovine serum (Millipore, ES-009-B), 1% (v/v) Pencillin-Streptomycin (Gibco, 15140-122), 1% (v/v) L-Glutamine (Gibco, 25030-081) and 500 μg/mL of G418 (Gibco, 10131-027).

Figure 3A:
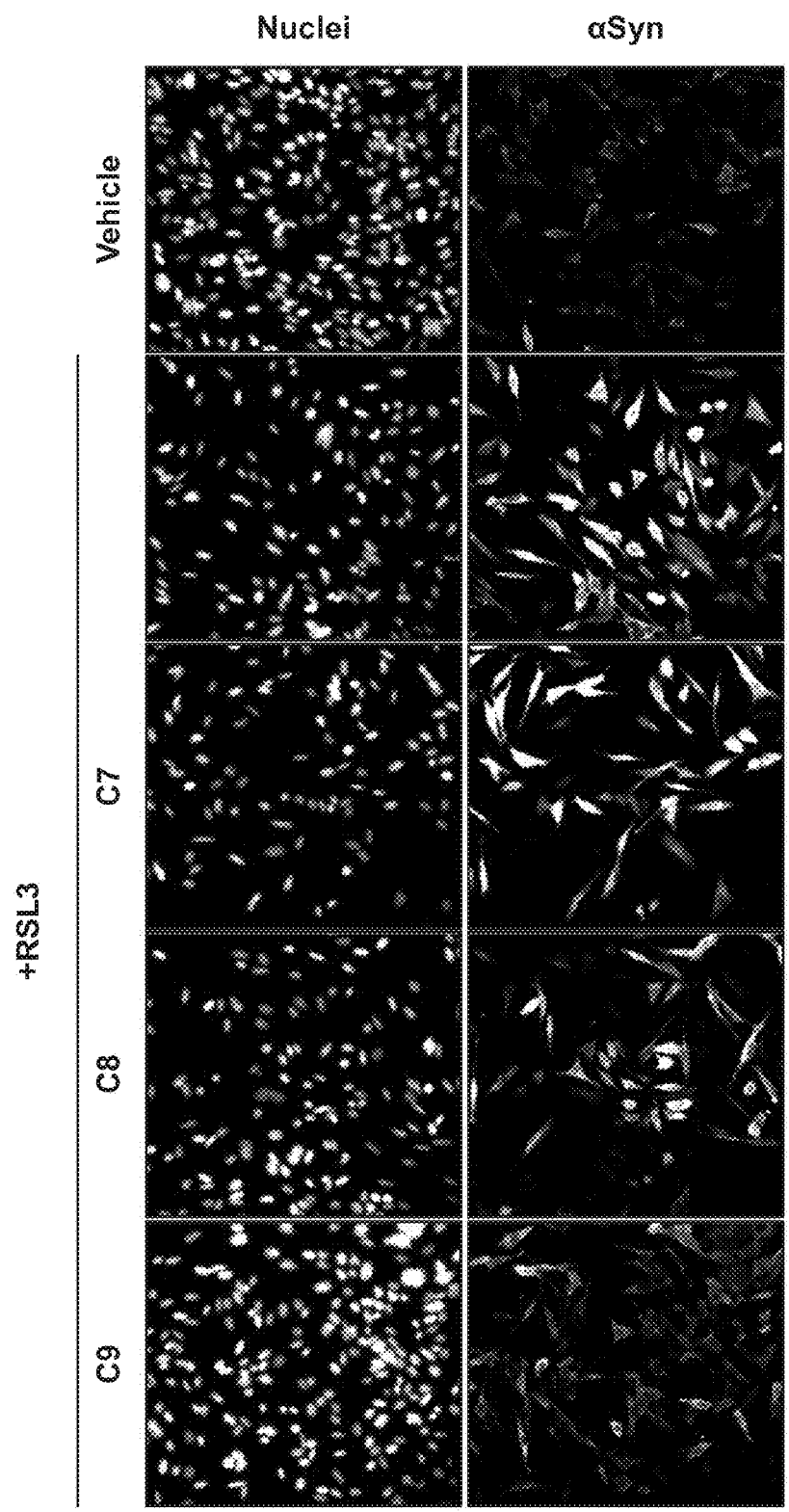
FIG. 3A shows nuclei and aggregated αSynuclein in N27 rat dopaminergic cells treated with RSL3 in the absence or presence of C9, C8, or C7 co-treatment.

N27 rat dopaminergic cells overexpressing a truncated (112 amino acid) human αSynuclein-GFP fusion protein, as described above, were maintained in normal culture conditions as described above. The day before the experiment, cells were plated in 96 well optical bottom, black walled plates at 3,000 cells/well, and maintained at 37° C. for 24 hr. The experiment was initiated by co-treating cells with (1S,3R)-methyl 2-(2-chloroacetyl)-1-(4-(methoxycarbonyl)phenyl)-2,3,4,9-tetrahydro-1H-pyrido[3,4-b]indole-3-carboxylate (1S,3R-RSL3, described by Yang et al., Cell 156: 317-331 (2014)) (60 nM) and 70 nM compounds (2,3,5-trimethyl-6-nonylcyclohexa-2,5-diene-1,4-dione (C9), 2,3,5-trimethyl-6-octylcyclohexa-2,5-diene-1,4-dione (C8), or 2,3,5-trimethyl-6-heptylcyclohexa-2,5-diene-1,4-dione (C7)) using a D300e compound printer (Tecan), and placed back in the incubator at 37° C. for 24 hr. Cells were fixed with 4% paraformaldehyde for 15 minutes at room temperature, washed 3 times with Dulbecco's phosphate-buffered saline (DPBS) buffer, and then incubated at room temperature for 48 hr with 1% Triton-X 100 solution (in DPBS) to enable selective labeling of aggregated αSynuclein. Cells were then washed and standard immunocytochemistry (ICC) methods were employed to label total αSynuclein (mouse anti-αSynuclein, 1:250, BD Biosciences). Cells were incubated with primary antibody overnight at 4° C. and then washed with DPBS 3 times the following day. Cells were then incubated at room temperature with a fluorescently conjugated secondary antibody (goat anti-mouse Alexa 647, Invitrogen) for 2 hr at room temperature. 10 nM Hoechst was also added to label nuclei, and cells were imaged on a high-content imaging platform (ThermoFisher, HSC Cellomics Arrayscan) to quantify total aggregated αSynuclein (see FIG. 3A).

Figure 3B:
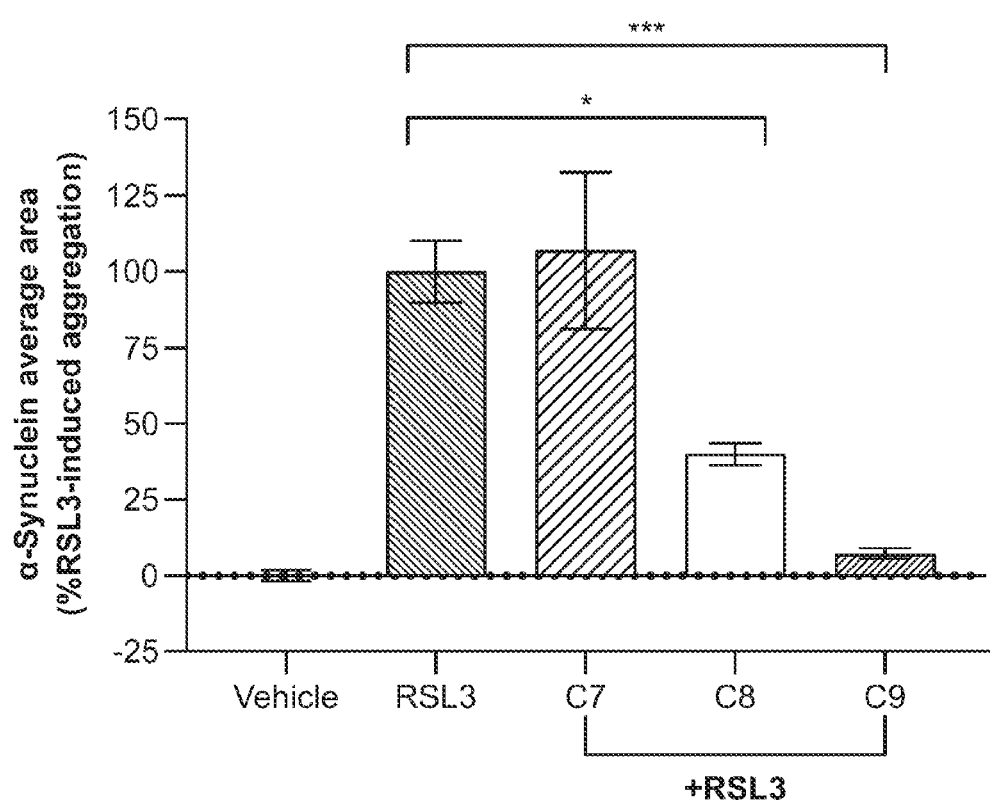
FIG. 3B shows the effects of C9, C8, or C7 treatment on RSL3-induced αSynuclein aggregation in N27 cells.

FIG. 3B shows the inhibition of RSL3-induced αSynuclein aggregation by compounds C7, C8, and C9. Statistical analysis of samples was performed via ordinary one-way ANOVA analysis with Dunnett's multiple comparisons test, comparing RSL3 only-treated vs. RSL3 plus compound-treated cells. C7 did not demonstrate any inhibition of αSynuclein aggregation (p>0.05). C8 and C9 showed significant inhibition of αSynuclein aggregation (p-values of 0.01 and 0.0003, respectively, with C9 demonstrating an approximately 5.45-fold higher level of aggregation inhibition over C8.

Example 11. Effectiveness of 2,3,5-trimethyl-6-nonylcyclohexa-2,5-diene-1,4-dione in a Mouse MPTP Model of Parkinson's Disease Summary Treatment of animals with (1-methyl-4-phenyl-1,2,3,6-tetrahydropyridine) (MPTP) (60 mg/kg) produced a significant depletion (~74%) of dopamine in the striatum, in line with literature reports and internal validation studies.

Figure 4A:
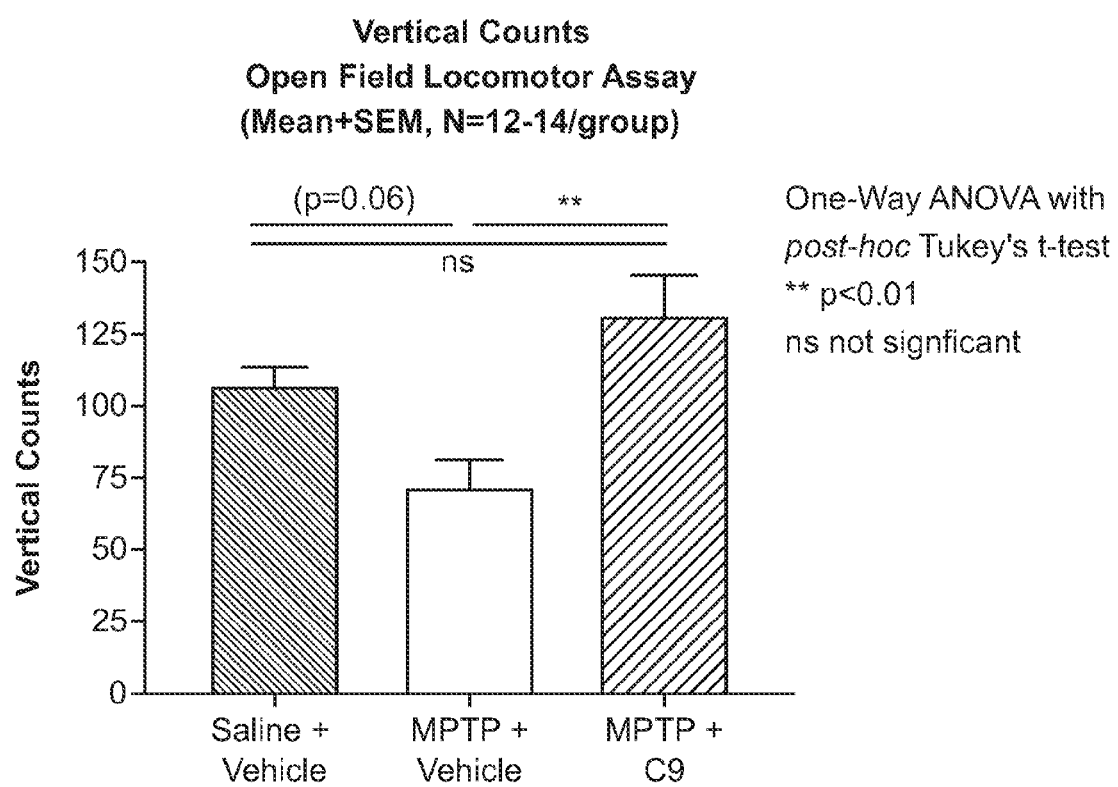
FIGS. 4A and 4B show the effect of C9 dosing on 1-methyl-4-phenyl-1,2,3,6-tetrahydropyridine (MPTP)-suppressed vertical activity (overall vertical counts and vertical time, respectively) in an open field locomotor assay of C57BL/6 mice.
Figure 4B:
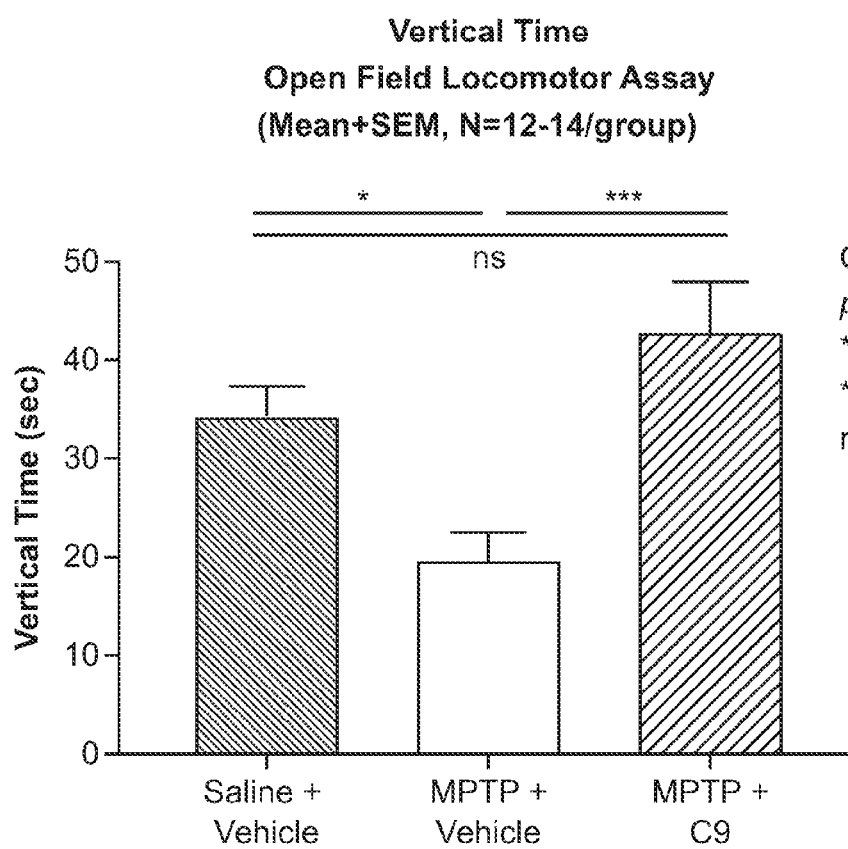

Administration of C9 (300 mg/kg) produced significant effects of treatments on vertical activity (vertical counts and time, as shown in FIGS. 4A and 4B).

Introduction

MPTP is a potent and selective nigrostriatal dopaminergic neurotoxin that produces many of the neuropathological features of Parkinson's disease (PD) in humans, nonhuman primates, and mice. In mice, MPTP produces nigrostriatal dopaminergic degeneration. Pharmacological agents that increase dopaminergic function or that block the neurotoxicity of MPTP also attenuate MPTP-associated locomotor dysfunction and have been useful in the clinic for treating Parkinson's disease. Moreover, MPTP-mediated toxicity may have a relationship to the mechanisms associated with dopaminergic loss in the disease indicating that this model may also be potentially useful for identifying agents that slow or reduce nigrostriatal dopaminergic loss.

In this study, C9 was tested in the MPTP-induced model of PD. The endpoints of the study were locomotor activity parameters in an open field test.

Experimental Procedures

Animals. Species: Mouse. Strain: C57Bl/6. Source of Animals: Charles River. Age: 6 to 7 weeks. Sex: Male. Randomization: Animals were assigned randomly to treatment groups. Blinding of Study: Experimenters were blinded to the experimental treatments Housing and Feeding. Acclimation/Conditioning: Not less than three days. Housing: Mice were housed on a 12 hr light/dark cycle (lights on 6:00 AM) No more than 4 mice per cage. Ventilated cage rack system. Diet: Standard rodent chow and water ad libitum.

Design Parameters. Route(s) of administration: PO. Dose Volume: PO: 5 mL/kg. Formulation(s): formulated by Melior according to directions from BioElectron. Vehicle—sesame oil (Spectrum Chemical, NF Catalog #SE130, CAS #8008-74-0). Dose Levels: 300 mg/kg. Dose Frequency: QD starting Day −2 (MPTP=Day 0) and until Day 7. Study duration: 11 days. Pretreatment time (up to 2 hrs): For Day 0 (MPTP Day): 30 min, Pretreatment time for Open Field Assay/Locomotor Activity (OFA/LMA) assay: 1 hr. Number of Groups: 3. Number of animals per group: 10. Total number of animals: 30 (in the study), 42 animals total (To ensure a proper power analysis of at least 10 animals/group, for all groups receiving MPTP, 4 additional animals were added to mitigate study impacts if there were MPTP-induced fatalities).

MPTP Treatment. MPTP was formulated in phosphate buffered saline and administered to mice three times at a dose of 20 mg/kg (1 mg/mL delivered at 20 mL/kg) at two-hour intervals (final dose of MPTP=60 mg/kg).

Locomotor activity. One day prior (baseline) and on Day 7 after MPTP administration (Day (−1) and Day 7), mice were monitored for various aspects of locomotor function using a fully automated open-field apparatus (Med-Associates, Inc). The apparatus consisted of a 10.75"×10.75" arena enclosed in a sound-attenuated box, equipped with the fan and house light. The arena is equipped with three 16-beam IR arrays located on X and Y axes for positional tracking and Z axis for rearing detection.

All mice were dosed with final dose of C9 or vehicle-sesame oil 1 hr prior to the Open Field Assay according to dosing schedule. Key locomotor parameters that are associated with dopaminergic deficiencies included rearing behavior (number of rears/15-minute session) and total distance traveled (per 15 minutes).

Data analysis. Data were averaged and are expressed as the average ±SEM. Data were analyzed by one-way ANOVA followed by a post-hoc tests. p-values of less than 0.05 were considered to be statistically significant from control.

Results

Effect of treatments on open field locomotor assay (vertical counts). Activity in the open field apparatus (vertical counts) in animals treated with Saline+Vehicle, MPTP+Vehicle, or MPTP+C9 was measured. Animals received treatments as indicated above. As shown in FIG. 4A, compared to Saline+Vehicle treated animals, the vertical counts were decreased in MPTP+Vehicle treated animals (p=0.06). C9 treatment of MPTP-challenged animals restored vertical counts to those observed in Saline+Vehicle control animals (MPTP+Vehicle vs. MPTP+C9, p<0.01; Saline+Vehicle vs. MPTP+C9, p=0.312). Data are presented as mean+SEM, n=12-14 in each group. Statistical analysis: one-way ANOVA with post hoc Tukey's test for multiple comparisons; **p<0.01; ns, not statistically significant (p>0.05).

Effect of treatments on open field locomotor assay (vertical time). Activity in the open field apparatus (vertical time) in animals treated with Saline+Vehicle, MPTP+Vehicle, or MPTP+C9 was measured. Animals received treatments as indicated above. As shown in FIG. 4B, compared to Saline+Vehicle treated animals, the vertical time was decreased in MPTP+Vehicle treated animals (p<0.05). C9 treatment of MPTP-challenged animals restored vertical time to those observed in Saline+Vehicle control animals (MPTP+Vehicle vs. MPTP+C9, p<0.001; Saline+Vehicle vs. MPTP+C9, p=0.315). Data are presented as mean+SEM, n=12-14 in each group. Statistical analysis: one-way ANOVA with post hoc Tukey's test for multiple comparisons; *, p<0.05; ***, p<0.001; ns, not statistically significant (p>0.05).

C9 dosing in the MPTP mouse model of PD demonstrated a significant improvement in locomotor activity as measured by vertical counts and time, two behavioral metrics reflective of dopaminergic function in the striatum (Meredith and Rademacher, J Parkinsons Dis. 1(1):19-33 (2012) and references therein).

Example 12. PK Profiles of C9 after Acute Oral Administration to Male C57 Mice A 300 mg/kg dose of C9 was administered as a sesame oil solution via oral gavage to four C57BL/6 mice. Eight hours after compound administration, plasma and brain exposure were measured (Table 10).

TABLE 10

Brain and Plasma Exposure of C9 in Mice after Oral Dosing

| Dose (mg/kg) | Route | Time (h) | C9 [Plasma] (ng/mL) | C9 [Brain] (ng/g) | Brain:Plasma Ratio |
|---|---|---|---|---|---|
| 300 | PO | 8 | 3830 | 27925 | 7 |

Non-limiting embodiments of the invention include the following:

Embodiment 1. A method of treating or suppressing a disorder selected from the group consisting of Alzheimer's Disease, Parkinson's Disease, traumatic brain injury, and ischemic-reperfusion related injury, comprising administering to a subject in need thereof a therapeutically effective amount of a compound of the formula:

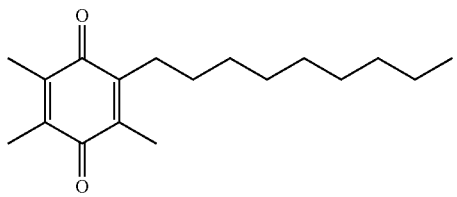 [SMILES: CCCCCCCCCC1=C(C)C(=O)C(C)=C(C)C1=O]

or the hydroquinone form thereof; or a solvate or hydrate thereof.

Embodiment 2. The method of Embodiment 1, wherein the compound is not a solvate or hydrate.

Embodiment 3. The method of Embodiment 1 or 2, wherein the compound is in the quinone form.

Embodiment 4. The method of Embodiment 1 or 2, wherein the compound is in the hydroquinone form.

Embodiment 5. The method of any one of Embodiments 1-4, wherein the method is for treating or suppressing Alzheimer's Disease.

Embodiment 6. The method of any one of Embodiments 1-4, wherein the method is for treating or suppressing Parkinson's Disease.

Embodiment 7. The method of any one of Embodiments 1-4, wherein the method is for treating or suppressing traumatic brain injury.

Embodiment 8. The method of any one of Embodiments 1-4, wherein the method is for treating or suppressing ischemic-reperfusion related injury.

Embodiment 9. The method of any one of Embodiments 1-4, wherein the method is for treating or suppressing stroke.

Embodiment 10. The method of any one of Embodiments 1-9, wherein the method is for treating the disorder.

Embodiment 11. The method of any one of Embodiments 1-9, wherein the method is for suppressing the disorder.

Embodiment 12. The method of any one of Embodiments 1-11, wherein the compound is administered orally.

Embodiment 13. The method of any one of Embodiments 1-11, wherein the compound is administered intravenously.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method of recrystallizing 2,3,5-trimethyl-6-nonylcyclohexa-2,5-diene-1,4-dione from a composition, comprising:
   a) contacting the composition with IPA and water such that the resulting ratio of IPA to water is 75-87% isopropanol (IPA)/25-13% water (v:v), at a temperature in the range of 40±5%-45±5% °C.;
   b) cooling the mixture to 32±5% °C.; and
   c) filtering the 2,3,5-trimethyl-6-nonylcyclohexa-2,5-diene-1,4-dione from the mixture.

2. The method of claim 1, wherein step (a) comprises:
   a1) contacting the composition with IPA;
   a2) warming the mixture to 40±5%-45±5% °C.; and
   a3) adding water to the mixture such that the ratio of IPA to water is 75-85% IPA:25-15% water (v:v).

3. The method of claim 1, wherein step (a) comprises stirring to dissolve the composition.

4. The method of claim 1, wherein the ratio of IPA:water is 80-85% IPA:20-15% water (v:v).

5. The method of claim 1, wherein the ratio of IPA:water is 85%±5% IPA:15% water (v:v).

6. The method of claim 2, wherein step (a3) comprises returning the temperature of the mixture to 40±5%-45±5% °C.

7. The method of claim 1, comprising polish filtering the mixture after step (a).

8. The method of claim 1, wherein step (b) comprises cooling to 32° C.±5% over 2±5%-10±5% hours.

9. The method of claim 1, wherein step (b) comprises cooling to 32° C.±5% over 6±5% hours.

10. The method of claim 1, wherein the method comprises a step (b1) after step (b), comprising holding the mixture at 32° C.±5% for 2±5%-24±5% hours.

11. The method of claim 1, wherein the method comprises a step (b1) after step (b), comprising holding the mixture at 32° C.±5% for 6±5% hours.

12. The method of claim 1, comprising a step (b2) after step (b) or (b1), when present, comprising cooling the mixture to 0° C.±5%.

13. The method of claim 1, wherein step (b2) comprises cooling the mixture to 0° C.±5% over 3±5%-24±5% hours.

14. The method of claim 1, wherein step (b2) further comprises holding the mixture at 0° C.±5% for 1±5% hour.

15. The method of claim 1, further comprising a step after step c): converting the 2,3,5-trimethyl-6-nonylcyclohexa-2,5-diene-1,4-dione, to a liquid or emulsion form.

16. A pharmaceutical composition comprising 2,3,5-trimethyl-6-nonylcyclohexa-2,5-diene-1,4-dione as made according to claim 1 wherein the pharmaceutical composition is a capsule or liquid dosage form for oral administration.

17. The pharmaceutical composition of claim 16, wherein the pharmaceutical composition is a liquid dosage form and the liquid dosage form is a solution or suspension.

18. The pharmaceutical composition of claim 16, wherein the pharmaceutical composition is a capsule and the capsule is a liquid-filled capsule.

19. A pharmaceutical composition comprising the liquid or emulsion form of claim 15, wherein the pharmaceutical composition is an oral solution, a liquid-filled capsule, or an injectable solution.

* * * * *